(12) United States Patent
Henary et al.

(10) Patent No.: US 11,572,475 B2
(45) Date of Patent: Feb. 7, 2023

(54) CARBOCYANINES FOR G-QUADRUPLEX DNA STABILIZATION AND TELOMERASE INHIBITION

(75) Inventors: Maged Henary, Lawrenceville, GA (US); W. David Wilson, Atlanta, GA (US)

(73) Assignee: GEORGIA STATE UNIVERSITY RESEARCH FOUNDATION, INC., Atlanta, GA (US)

(*) Notice: Subject to any disclaimer, the term of this patent is extended or adjusted under 35 U.S.C. 154(b) by 0 days.

(21) Appl. No.: 14/233,044

(22) PCT Filed: Jul. 18, 2012

(86) PCT No.: PCT/US2012/047118
§ 371 (c)(1),
(2), (4) Date: Jan. 15, 2014

(87) PCT Pub. No.: WO2013/012886
PCT Pub. Date: Jan. 24, 2013

(65) Prior Publication Data
US 2014/0142147 A1    May 22, 2014

Related U.S. Application Data

(60) Provisional application No. 61/508,837, filed on Jul. 18, 2011.

(51) Int. Cl.
| | |
|---|---|
| C09B 23/06 | (2006.01) |
| C07D 209/14 | (2006.01) |
| C07D 403/06 | (2006.01) |
| C07D 213/73 | (2006.01) |
| C07D 209/49 | (2006.01) |
| C07D 403/12 | (2006.01) |
| C07D 407/12 | (2006.01) |
| C07D 249/10 | (2006.01) |
| C07D 231/14 | (2006.01) |
| C07D 413/14 | (2006.01) |
| C07D 239/34 | (2006.01) |
| C07D 231/20 | (2006.01) |
| C07D 401/14 | (2006.01) |
| C07D 401/04 | (2006.01) |
| C07D 403/10 | (2006.01) |
| C07D 209/18 | (2006.01) |
| C07D 235/24 | (2006.01) |
| C07D 417/12 | (2006.01) |
| C07D 213/64 | (2006.01) |

(52) U.S. Cl.
CPC .......... *C09B 23/06* (2013.01); *C07D 209/14* (2013.01); *C07D 209/18* (2013.01); *C07D 209/49* (2013.01); *C07D 213/64* (2013.01); *C07D 213/73* (2013.01); *C07D 231/14* (2013.01); *C07D 231/20* (2013.01); *C07D 235/24* (2013.01); *C07D 239/34* (2013.01); *C07D 249/10* (2013.01); *C07D 401/04* (2013.01); *C07D 401/14* (2013.01); *C07D 403/06* (2013.01); *C07D 403/10* (2013.01); *C07D 403/12* (2013.01); *C07D 407/12* (2013.01); *C07D 413/14* (2013.01); *C07D 417/12* (2013.01)

(58) Field of Classification Search
None
See application file for complete search history.

(56) References Cited

U.S. PATENT DOCUMENTS

| | | |
|---|---|---|
| 5,163,898 A | 11/1992 | Morcos |
| 2004/0054178 A1 | 3/2004 | Madaule |
| 2005/0245734 A1 | 11/2005 | Caputo |
| 2010/0249175 A1 | 9/2010 | Wilson |
| 2010/0267008 A1 | 10/2010 | Mujumdar |

FOREIGN PATENT DOCUMENTS

| | | |
|---|---|---|
| CH | 143287 | 10/1930 |
| EP | 1221465 | 7/2002 |
| EP | 1652892 | 5/2006 |
| WO | 2006020947 | 2/2006 |

(Continued)

OTHER PUBLICATIONS

Chemical Abstract Registry No. 869939-060, indexed in the Registry File on STN CAS Online Dec. 14, 2005.*
Ito et al., A medium-term rat liver bioassay for rapid in vivo detection of carcinogenic potential of chemicals. Cancer Science, 2003, 94, 3-8.*
Chemical Abstract Registry No. 329039-84-1, indexed in the Registry File on STN CAS Online Mar. 27, 2001.*
Chemical Abstract Registry No. 741224-65-7, indexed in the Registry File on STN CAS Online Sep. 8, 2004.*

(Continued)

*Primary Examiner* — Po-Chih Chen
(74) *Attorney, Agent, or Firm* — PABST Patent Group LLP

(57) ABSTRACT

Cyanines which selectively bind to G-quadruplex DNA complexes, particularly quadruplexes expressed in cancer cells, and methods of making and using thereof are described herein. The cyanine can be a symmetrical or unsymmetrical streptocyanine, hemicyanine, closed chain cyanine, or combinations thereof. The cyanine is preferably substituted with one or more groups that minimize or prevent aggregation of the cyanine and/or inhibit binding of the cyanine to duplex DNA. One or more of the cyanines can be formulated with one or more pharmaceutical excipients and/or carrier to prepare pharmaceutical compositions suitable for administration to a patient, particular a human patient. The compounds and compositions described herein can be used to treat diseases or disorders characterized by the expression of G-quadruplex DNA, such as cancer.

32 Claims, 22 Drawing Sheets
Specification includes a Sequence Listing.

(56) References Cited

FOREIGN PATENT DOCUMENTS

| WO | 2007061768 | 5/2007 |
|---|---|---|
| WO | 2011151287 | 12/2011 |

OTHER PUBLICATIONS

Chemical Abstract Registry No. 162920-62-9, indexed in the Registry File on STN CAS Online May 12, 1995.*
Chemical Abstract Registry No. 162920-59-4, indexed in the Registry File on STN CAS Online May 12, 1995.*
Chemical Abstract Registry No. 802902-15-4, indexed in the Registry File on STN CAS Online Dec. 27, 2004.*
Chemical Abstract Registry No. 794490-02-1, indexed in the Registry File on STN CAS Online Dec. 8, 2004.*
Chemical Abstract Registry No. 780737-50-0, indexed in the Registry File on STN CAS Online Nov. 15, 2004.*
Chemical Abstract Registry No. 1113100-82-5, indexed in the Registry File on STN CAS Online Mar. 1, 2004.*
Chemical Abstract Registry No. 911100-04-4, indexed in the Registry File on STN CAS Online Oct. 23, 2006.*
Chemical Abstract Registry No. 117124-25-1, indexed in the Registry File on STN CAS Online Oct. 29, 1988.*
Chemical Abstract Registry No. 790658-02-5, indexed in the Registry File on STN CAS Online Nov. 30, 2004.*
Chemical Abstract Registry No. 754960-97-9, indexed in the Registry File on STN CAS Online Oct. 1, 2004.*
Federal Register (published on 2011, vol. 76, No. 27, p. 7166).*
Chemical Abstract Registry No. 904959-24-6, indexed in the Registry File on STN CAS Online Aug. 28, 2006.*
Chemical Abstract Registry No. 774169-84-5, indexed in the Registry File on STN CAS Online Nov. 3, 2004.*
Armitage, B. A., Cyanine Dye-DNA Interactions: Intercalation, Groove Binding, and Aggregation. Topics in Current Chemistry, 2005, 253, 55-76.*
Chemical Abstract Registry No. 393540-84-6, indexed in the Registry File on STN CAS Online Feb. 19, 2002.*
Pronkin et al., Spectral and Kinetic Investigation of INteraction of 3,3'-Diethyl-9-chlorothiacarbocyanine Perchlorate with DNA. High Energy Chemistry, 2007, 41, 97-102.*
Liu et al., Interactions of an amphiphilic thiacarbocyanine dye with polypeptides and DNA at the air/water interface. Colloids and Surfaces A: Phyicochemical and Engineering Aspects, 2000, 175, 153-159.*
Chemical Abstract Registry No. 758672-98-9, indexed in the Registry File on STN CAS Online Oct. 8, 2004.*
Chemical Abstract Registry No. 398458-98-5, indexed in the Registry File on STN CAS Online Mar. 6, 2002.*
Allmann, et al., "Synthesen mit substituierten malonaldehyden, XXIII. [gamma]-cycloalkyl-pentamethincyanin-farbstoffe", Chemische Berichte, 109(9):3005-16 (1976) (Eng. Abstract Only).
Friedman, et al., "Thiazolobenzo-1, 2, 3-thiacliazoles and derived cyanine dyes", Chem Heterocyclic Compounds, 1(5):481-7 (1966).
Friedman, et al., "1, 2-dimethy limidaz obenz o-1; 2\,3\-thiadia zoies and derived cyanine dyes", Chem Heterocyclic Compounds, 3(3):399-402 (1967).
Garmaise, et al., "Anthelmintic quaternary salts. Thiacyanines and hemithiacyanines", J Med Chem., 10(5):897-9 (1967).
Kiciak, "Luminescence of sensitizing dyes. I. Influence of the dye structure on its luminescence", Roczniki Chemi Annales Societatis Chimicae Polonorum, 37:225-47 (1963)(Eng. Abstract Only).
Neidle, et al., "Chemical approaches to the discovery and development of cancer therapies", Nat Rev Cancer, 5(4):285-96 (2005).
Reichardt, et al., "Synthesen mit substituierrten malondialdehyden, X [gamma]-cycloalkyl-pentamethincyanin-farbstpffe", Chemische Berichte, 104(3):822-9 (1971)(Eng. Abstract Only).

Zubarovskii, et al.,"Synthesis of thiazole derivatives XXIII, 2-Methylbenzimiciazoles with thiazole, benzolhiazole and quinoHne groups as substituents", Chem of Heteocyclic Compounds, 3(4):152-7 (1967).
Zubarovskii, et al., "Synthesis of brnzimidazole derivatives", Chem Heterocyclic Compounds, 11(2):218-21 (1975).
Extended European Search Report and Written Opinion for EP 12815580 dated Nov. 18, 2014.
Brooks, et al., "Making sense of G-quadrupfex and I-motif functions in oncogene promoters", FEBS J., 277(17), 3459-69 (2010).
Meguellati, et al., "DNA-templated synthesis of trimethine cyanine dyes: a versatile fluorogenic reaction for sensing G-quadruplex formation" , Angwe Cem Int, 49(15):2738-42 (2010).
Pubchem CID 12462172, created Feb. 8, 2007, retrieved from internet http://pubchem.ncbi.nlm.nih.gov/summary/summary.cgi?cid=1 2462172&loc=ec rcs>, retrieved Oct. 10, 2012.
Yang, et al., "Verification of specific G-quadruplex structure by using a novel cyanine dye supramolecular assembly: I. recognizing mixed G-quadruplex in human telomeres", Chem Commun, 7(9): 1103-5 (2009).
Yang, et al., "Verification of specific G-quadruplex structure by using a novel cyanine dye supramolecular assembly: II. The binding characterization with specific Intramolecular G-quadruplex and the recognizing mechanism", Nucleic Acids Res., 38(3):1022-33 (2010).
Beattie, et al., "35 Dicarbocyanines. A new series of cyanine dyes", J Chem. Soc., 260-8 (1932).
Chibisov, et al., "Effects of substituents in the polymethine chain on the photoprocesses in indodicarbocyanine dyes", J Chem. Soc., 92(24):4917-25 (1996).
Dramanyan, et al., "Laser photolysis of dicarbocyanine dyes", Bull Academcy Sci of USSR, Div Chem Sci., 27:506-10 (1978).
Fu, et al., "Synthesis an special properties of novel water-soluble indocyanine dyes as fluorescent dyes for proteins detection", Chinese J Chem., 29(3):493-8 (2011).
Hilderbrand, et al., "Optimized pH-responsive cyanine fluorochromes for detection of acidic environments", Chem Comm., 26:2747-9 (2007).
Klotz, et al., "Homo and hetero-[3]rotaxanes with two[pi]-systems clasped in a single macrocycle contents—Supporting Information", J Am Chem Soc., 128(48):S1-S13 (2006).
Murphy, et al., "Cyanine borate salts that form penetrated ion pairs in benzene solution: Synthesis properties and structure", J Org Chern., 60:2411-22 (1995).
Pandey, et al., "Photo-rechargeable battery effect in first generation cationic-cyanine dendrimers", Adv Materials, 22(35):3954-8 (2010).
Peng, et al., "Synthesis and physical performance of ;indole and benzimidazole cyanine dyes", J Materials Chem., 6(4):559-65 (1996).
Tolmachev, et al., "Cyanine dyes with phosphorus-containing substituents in the heterocyclic nuclei", J Gen Chem. USSR, 59(4):827-31 (1989).
Zhifei, et al., "Phyotophysics of indocarbocyanine dyes in organic solvents", J Chinese Chem Soc., 45(2):237-40 (1998).
Office Action for European Application 12815580.1 dated Nov. 13, 2015.
Konig, "Uber Indolenino-cyanine (indocyanine)" Chemische Berichte, 54(4):685-92 9 (1924), (European office action for EP12815580.1 only).
Lifshits, et al., Zhurnal obshchei khimii 38(0):2025-30 (1968), (European office action for EP12815580.1 only).
Moreau, et al., "Synthesis d\indomonocarbocyanines a elimination biliaire selective. Etude experimentale chezl\animal", Chimie Therapeutique, 9(3):274-80 (1974), (European office action for EP12815580.1 only).
Mereux, et al., "synthese et etude de colorants polymethiniques contenant un ou deux chromoohores conjugues, derives de bonzobithiazoles isomers", Compte rendus des séances de l\academie des sciences, serie c: Sciences Chimques. 275:749-52 (1972) (No English Translation Available), (European search report for EP12815580.1 only).

\* cited by examiner

SEQUENCE LISTING

<160> NUMBER OF SEQ ID NOS: 3

<210> SEQ ID NO 1
<211> LENGTH: 22
<212> TYPE: DNA
<213> ORGANISM: Homo sapiens

<400> SEQUENCE: 1
agggttaggg ttagggttag gg             22

<210> SEQ ID NO 2
<211> LENGTH: 19
<212> TYPE: DNA
<213> ORGANISM: Homo sapiens

<400> SEQUENCE: 2
agggtgggga gggtgggga                           19

<210> SEQ ID NO 3
<211> LENGTH: 24
<212> TYPE: DNA
<213> ORGANISM: Artificial Sequence
<220> FEATURE:
<223> OTHER INFORMATION: Synthetic duplex sequence

<400> SEQUENCE: 3
cggaattcgc ttttgcgaat tcgc                     24

CARBOCYANINES FOR G-QUADRUPLEX DNA STABILIZATION AND TELOMERASE INHIBITION

CROSS REFERENCE TO RELATED APPLICATIONS

This application is a 371 application of the International Application No. PCT/US2012/047118 entitled "Carbocyanines for G-Quadruplex DNA Stabilization and Telomerase Inhibition", filed in the United States Receiving Office for the PCT on Jul. 18, 2012, which claims the benefit of and priority to U.S. Provisional Application No. 61/508,837, filed Jul. 18, 2011.

REFERENCE TO SEQUENCE LISTING

The Sequence Listing submitted Dec. 27, 2013 as a text file named "GSURF_2011_10_ST25.txt," created on Jan. 15, 2014, and having a size of 896 bytes is hereby incorporated by reference pursuant to 37 C.F.R. § 1.52(e)(5).

FIELD OF THE INVENTION

This invention is in the field of cyanine dyes that preferentially bind quadruplex DNA and methods of making and using thereof.

BACKGROUND OF THE INVENTION

In addition to the typical right-handed double helix, DNA can adopt other biologically relevant conformations that are important in regulating function. Four-stranded G-quadruplexes, for example, are non-canonical DNA structures that are found at the ends of human chromosomes as well as in promoter regions of a number of oncogenes. The quadruplexes are formed by a series of stacked guanine tetrads held together in a coplanar cyclic array that require a coordinated monovalent cation, typically potassium ion ($K^+$). Quadruplex DNA can assume multiple conformations depending on many factors, including sequence length and the nature of the monovalent cation.

In the early 1990's, a correlation between G-quadruplex formation and cancer cells was established. The telomere and several oncogene promoter regions were identified as sequences that could form the quadruplex motif in vitro. Confirmation of these structures in vivo is described in Brooks et al., *FEBS J.*, September 277(17), 3459-69 (2010).

Current DNA targeting drugs on the market include Pentamidine, Berenil, and Trabectadin. These drugs, however, target double stranded DNA by blocking in the minor groove in *T. Brucei* parasites, intercalating between base pairs of *T. Brucei* kinetoplast DNA, and alkylating in the minor groove of cancer DNA, respectively. Many other DNA targeting drugs have been investigated. However, most of these drugs are designed to bind in the minor groove, by intercalating or bis-intercalating, or interact with the phosphate backbone. Unfortunately, most of these drugs have been rejected due to poor solubility or selectivity, unacceptable toxicity, and/or the development of resistance.

There exists a need for compounds which preferentially bind to quadruplex DNA complexes and have little or no binding affinity for duplex DNA complexes and methods of making and using thereof. The compounds preferably have sufficient solubility or can be formulated to achieve sufficient solubility for administration in vivo and exhibit minimal toxicity and/or resistance.

Therefore, it is an object of the invention to provide compounds which preferentially bind to quadruplex DNA complexes and have little or no binding affinity for duplex DNA and methods of making and using thereof.

SUMMARY OF THE INVENTION

Cyanines which selectively bind to G-quadruplex DNA complexes, particularly quadruplexes expressed in cancer cells, and methods of making and using thereof are described herein. The cyanine can be a streptocyanine or open-chain cyanine (e.g., end groups are acyclic), hemicyanine (e.g., one end group is cyclic and the other end group is acyclic) and closed chain cyanine (e.g., both end groups are cyclic). Streptocyanines and closed chain cyanines can be symmetrical (e.g., same donor and acceptor termini) or unsymmetrical (e.g., different donor and acceptor termini). The unsymmetrical cyanines can have different heterocyclic groups or different substituent patterns on the heterocyclic groups.

The cyanine is preferably substituted with one or more groups that minimize or prevent aggregation of the cyanine and/or inhibit binding of the cyanine to duplex DNA. In some embodiments, the cyanines selectively bind quadruplex DNA complexes that are expressed in cancer cells. In other embodiments, the cyanines can be taken up in the nucleus of the cell.

In one embodiment, the cyanine has the structure:

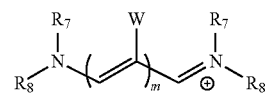

wherein:
m=0, 1, 2, or 3;
each occurrence of $R_7$ and $R_8$ is independently hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, and r is an integer from 1 to 6; and each occurrence of W on the bridge is independently hydrogen; halogen (e.g., F, Cl, Br, or I); cyano; trifluoromethyl; substituted or unsubstituted aryl, such as benzoic acid; substituted or unsubstituted alkyl, alkenyl, alkynyl, cycloalkyl, or cycloalkenyl; a group containing one or more cationic atoms or moieties or atoms or moieties that are cationic under physiological conditions, such as nitrogen-containing aromatic groups (e.g., pyridine), cyclic amines, amidines, $C_{1-20}$ alkyl amino or quaternized amino, preferably $C_{1-10}$ alkyl amino or quaternized amino, more preferably $C_{1-6}$ alkyl amino or quaternized amino.

W is preferably a group that minimizes or prevents aggregation and/or inhibits binding to duplex DNA compared to a cyanine not containing W.

In another embodiment, the cyanine has the structure:

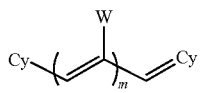

wherein,

Cy is a substituted or unsubstituted heteroaromatic moiety; and m and W are as defined above.

In some embodiments, Cy contains a first nitrogen substituted with a group containing one or more cationic groups. In preferred embodiments, this nitrogen is typically conjugated to the bridge of the cyanine.

In some embodiments, W is a group containing one or more cationic atoms or groups.

In other embodiments, the heteroaromatic ring and/or the bridge is substituted with one or more substituents which reduces the tendency of the cyanine to aggregate or prevents the cyanine from aggregating. The one or more substituents can prevent aggregation via steric effects (e.g., size of the substituent(s) decreases or prevents aggregation) and/or electronic effects (e.g., the electronic structure of the substituent(s) prevents aggregation). In some embodiments, the substituent(s) which reduces or prevents aggregation is a halogen, such as F, Br, Cl, or I, or alkoxy, such as methoxy.

In other embodiments, the heteroaromatic ring and/or the bridge is substituted with one or more groups that inhibit binding to duplex DNA complexes. These groups can be the same as the groups that prevent or minimize aggregation or different groups. In particular embodiments, the heteroaromatic ring contains an atom substituted with one more sterically bulky substituents. The sterically bulky substituents may prevent aggregation and/or prevent binding to duplex DNA. Non-limiting examples of such substituted atoms include a second heteroatom, such as —NR, where R is a substituted or unsubstituted sterically bulky alkyl group, such as methyl, ethyl, isopropyl, isobutyl, sec-butyl, t-butyl, pentyl and isomers thereof, hexyl and isomers thereof, substituted or unsubstituted cyclohexyl groups; substituted or unsubstituted aryl groups; etc, or —CR$_{10}$R$_{11}$, wherein R$_{10}$ and R$_{11}$ are defined the same as R. In a preferred embodiment, R$_{10}$ and R$_{11}$ are methyl groups.

In other embodiments, the cyanine has the formula above, wherein Cy is substituted with one or more groups which prevent aggregation and/or inhibit binding to duplex DNA, such as halogen (e.g., F, Cl, Br, or Cl) or alkoxy; Cy contains a first nitrogen atom, conjugated to the bridge, which is substituted with a group containing one or more cationic groups, and Cy contains a second atom, also adjacent to the point of connection to the bridge, substituted with one or more sterically bulky groups as discussed above.

In still other embodiments, the heteroaromatic ring is substituted with one or more substituents which reduce the tendency of the cyanine to aggregate or prevent the cyanine from aggregating and/or inhibit binding to duplex DNA, the nitrogen heteroatom conjugated to the bridge is substituted with a group containing one or more cationic moieties or one or more moieties that can be made cationic, such as under physiological conditions, and at least one occurrence of W is a halogen, such as F, Cl, Br, or I or a group containing one or more cationic atoms or groups.

In another embodiment, the cyanine has the formula:

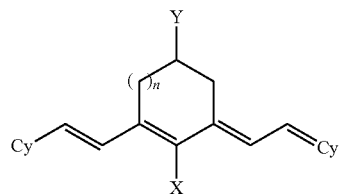

wherein Cy is as defined above, X and Y are as defined above for W, and n=0 (cyclopentyl ring) or 1 (cyclohexyl ring). In preferred embodiments, X and/or Y are groups that prevent or minimize aggregation and/or inhibit binding to duplex DNA.

In particular embodiments, the cyanine has the formula shown above, wherein each occurrence of Cy is selected from:

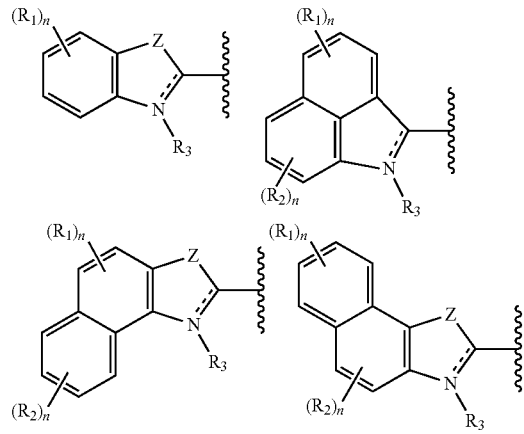

wherein n, as valence allows, is an integer from 0-4;

each occurrence of R$_1$ and R$_2$ is independently absent or selected from hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(=O)R", —C(=O)R', —C(=O)OR', —OC(=O) R', —O(CR'R")$_r$C(=O)R', —O(CR'R")$_r$NR"C(=O)R', —O(CR'R")$_r$NR"SO$_2$R', —OC(=O)NR'R", —NR'C(=O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, and r is an integer from 1 to 6;

each of R$_3$ is independently hydrogen, a group having no charge, such as C$_{1-20}$ alkyl, preferably C$_{1-10}$ alkyl, more preferably C$_{1-6}$ alkyl; a positively charged or group that can be made positively charged, such as C$_{1-20}$ alkyl amino or quaternized amino, preferably C$_{1-10}$ alkyl amino or quaternized amino, more preferably C$_{1-6}$ alkyl amino or quaternized amino;

Z is O, S, NR$_4$ or CR$_5$R$_6$; wherein R$_4$-R$_6$ are selected from hydrogen; F, (e.g., Cl, Br, and I); hydroxy, —OR'; —SR'; —NR'R"; nitro; cyano; carbonyl (e.g., aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, and r is an integer from 1 to 6.

The double bonds are represented as dotted line (i.e., optional) depending on whether the Cy has a double bond within the ring (i.e., double bond to nitrogen resulting in four bonds to nitrogen and the nitrogen is positively charged) or the double bond is exocyclic (i.e., nitrogen has three bonds and is neutral). Other heteroaromatic groups known in the art can be used to prepare the cyanines described herein.

In particular embodiments, the cyanine has the structure:

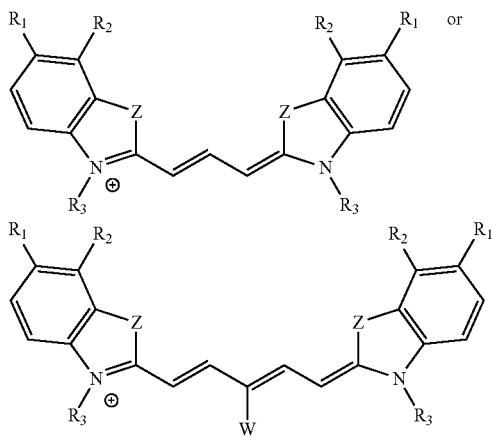

wherein R$_1$-R$_3$, Z, and W are as defined above.

One or more of the cyanines described herein can be formulated with one or more pharmaceutical excipients and/or carriers to prepare pharmaceutical compositions suitable for administration to a patient, particular a human patient. However, the pharmaceutical composition can be administered to animals other than humans. The compositions can be administered enterally, parenterally, topically, or via the pulmonary route. In particular embodiments, the compositions are administered enterally or parenterally.

The compounds and compositions described herein can be used to treat diseases or disorders characterized by the expression of G-quadruplex DNA. In certain embodiments, the disease or disorder is a proliferative disorder, such as cancer. The compositions provided an effective amount of the one or more cyanines to selectively bind to G-quadruplex DNA and interrupt DNA replication resulting in the selective death of cancer cells.

DETAILED DESCRIPTION OF THE INVENTION

I. Definitions

Figure 1A:
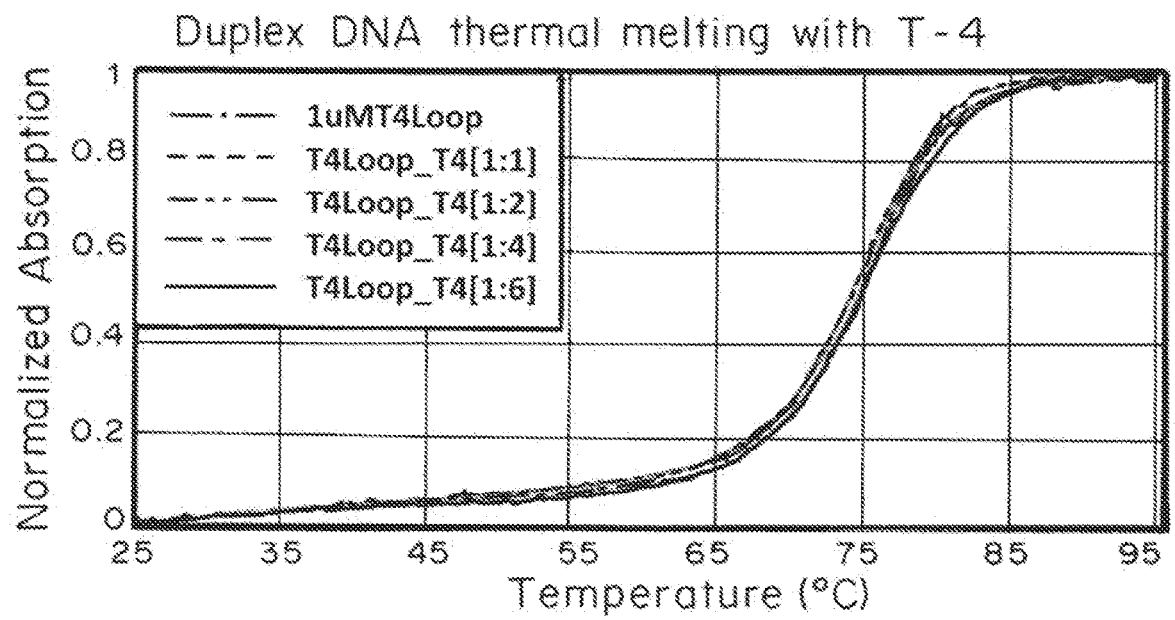
FIGS. 1A and 1B are graphs showing absorption as a function of temperature (° C.) for complexes formed between compound T-4 and duplex DNA (FIG. 1A) and quadruplex DNA (FIG. 1B). The lowest temperature plot is for free DNA and the highest temperature plot is for the highest ratio of compound to DNA.

"Cyanine", as used herein, are characterized as possessing two heterocyclic moieties, acting as both electron donors and acceptors, and are joined by a single or odd number of methine groups in which (n+1) bi-electrons are distributed over n atoms producing a delocalized cation across the methine chain. This unique characteristic gives cyanine dyes a wider absorption spectra than other known classes of dyes. Synthetic cyanines are known to absorb between the visible and infrared regions of the electromagnetic spectrum. In addition, cyanines possess narrow absorption bands and high extinction coefficients.

Non-limiting examples of cyanines include streptocyanines or open-chain cyanine, hemicyanines, and closed chain cyanines. Streptocyanines and closed chain cyanines can be symmetrical-similar heterocyclic moieties—(donor and acceptor groups) or unsymmetrical-different heterocyclic moieties (donor and acceptor groups).

"Bridge", as used herein, refers to the moiety that couples the two heterocyclic moieties. The bridge is typically a polyene segment having an odd number of carbons. The bridge can be substituted or unsubstituted. If the bridge is substituted, it can have one or more substituents. The substituents can be the same or different.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls, heteroaryls, and/or heterocycles. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, more preferably 10 or fewer, most preferably 6 or fewer. If the alkyl is unsaturated, the alkyl chain generally has from 2-30 carbons in the chain, preferably from 2-20 carbons in the chain, more preferably from 2-10 carbons in the chain. Likewise, preferred cycloalkyls have from 3-20 carbon atoms in their ring structure, preferably from 3-10 carbons atoms in their ring structure, most preferably 5, 6 or 7 carbons in the ring structure.

The terms "alkenyl" and "alkynyl" refer to unsaturated aliphatic groups analogous in length and possible substitution to the alkyls described above, but that contain at least one double or triple bond respectively.

The term "alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$ wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —CF3; —CN; —$NCOCOCH_2CH_2$; —NCOCOCHCH; —NCS; and combinations thereof.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

"Alkoxy", "alkylamino", and "alkylthio" are used herein in their conventional sense, and refer to those alkyl groups attached to the remainder of the molecule via an oxygen atom, an amino group, or a sulfur atom, respectively.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$)alkyl, phenyl or benzyl, and optionally containing 1-3 double bonds and optionally substituted with one or more substituents. One of the rings can be aromatic. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents as defined above for alkyl and aryl.

"Halogen", as used herein, refers to fluorine, chlorine, bromine, or iodine.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The compounds described herein may exist in unsolvated forms as well as solvated forms, including hydrated forms. In general, the solvated forms are equivalent to unsolvated forms and are within the scope of the compounds described herein. The compounds described herein may exist in multiple crystalline or amorphous forms. In general, all physical forms are equivalent for the uses described herein and are intended to be within the scope of the compounds described herein.

The compounds described herein may possess asymmetric carbon atoms (chiral centers) or double bonds; the racemates, diastereomers, geometric isomers and individual isomers are within the scope of the compounds described herein. The compounds described herein may be prepared as a single isomer or as a mixture of isomers. In some embodiments, the compounds are prepared as a single isomer, substantially separated from other isomers. Methods of preparing substantially isomerically pure compounds are known in the art.

The "effective amount", e.g., of the cyanines described herein, refers to an amount of the cyanine in a composition or formulation which, when applied as part of a desired dosage regimen brings about, e.g., a change in the rate of cell proliferation and/or the state of differentiation of a cell and/or rate of survival of a cell according to clinically acceptable standards for the disorder to be treated.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "patient" or "subject" to be treated refers to either a human or non-human animal.

"Half maximal inhibitory concentration, $IC_{50}$", as used herein, refers to a measure of the effectiveness of a compound in inhibiting biological or biochemical function. This quantitative measure indicates how much of a particular drug or other substance (inhibitor) is needed to inhibit a given biological process (or component of a process, i.e. an enzyme, cell, cell receptor or microorganism) by half. According to the FDA, $IC_{50}$ represents the concentration of a drug that is required for 50% inhibition in vitro. The $IC_{50}$ can be determined using a variety of assays known in the art.

"Selective for quadruplex DNA", as used herein, means that the cyanine selectively binds quadruplex DNA structures at least 2, 4, 6, 8, 10, 15, 20, 25, 30, 35, 40, 45, 50, 75, 100, 150, 200, 250, 500, 750, or 1000 times higher than duplex DNA. The range includes all values between 2 and 1000. In some embodiments, the cyanine does not bind duplex DNA to an extent that can be measured by thermal analysis and/or surface plasmon resonance ("SPR") spectroscopy.

"Prevents or minimizes aggregation", as used herein, means that the cyanines do not aggregate or if aggregation does occurs, it does not substantially affect the therapeutic efficacy of the cyanines. Cyanines are known to aggregate through van der Waals interactions, hydrogen bond and/or hydrophobic interactions. Two types of aggregates have been described: J-aggregates, characterized by red-shifted absorption spectrum (compared with the monomer band) and sharp absorption band and enhanced fluorescence and H-aggregates (hypsochromic shift), characterized by blue-shifted absorption spectrum (compared with the monomer band) and broad absorption band with negligible or low fluorescence. Aggregation is dependent on environmental changes, such as solvent polarity, pH, and temperature. The degree of aggregation can be evaluated using NMR, HRMS, and/or fluorescence spectroscopy.

Dye dimerization affinity can be determined spectroscopically either by varying solvent hydrophobicity with fixed dye concentration or varying dye concentration with fixed solvent hydrophobicity. For absorption measurements, maximum absorptivity of the dye monomeric or aggregate peak (whichever is greater) would be around 0.3-0.35 AU to achieve noise reduction and decrease possible solubility problems. For fluorescence measurements, this value is typically fixed at or below 0.1 AU to avoid inner filter effect problems. Monomeric and dimeric concentrations can be determined from absorption and fluorescence spectra using Beer's law or fluorescence measured at the monomeric fluorescence peak.

II. Carbocyanines

Cyanines which selectively bind to G-quadruplex DNA complexes, particularly quadruplexes expressed in cancer cells, and methods of making and using thereof are described herein. The cyanine can be a streptocyanine or open-chain cyanine (e.g., end groups are acyclic), hemicyanine (e.g., one end group is cyclic and the other end group is acyclic) and closed chain cyanine (e.g., both end groups are cyclic). Streptocyanines and closed chain cyanines can be symmetrical (e.g., same donor and acceptor termini) or unsymmetrical (e.g., different donor and acceptor termini). The unsymmetrical cyanines can have different heterocyclic groups or different substituent patterns on the same heterocyclic groups.

The cyanine is preferably substituted with one or more groups that minimize or prevent aggregation of the cyanine and/or inhibit binding of the cyanine to duplex DNA. In more preferred embodiments, the cyanines selectively bind quadruplex DNA complexes that are expressed in cancer cells. In even more preferred embodiments, the cyanines can be taken up in the nucleus of the cell.

In one embodiment, the cyanine has the structure:

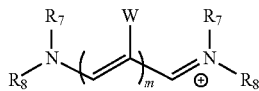

wherein:

m=0, 1, 2, or 3;

each occurrence of $R_7$ and $R_8$ is independently hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR')); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, and r is an integer from 1 to 6; and each occurrence of W on the bridge is independently hydrogen; halogen (e.g., F, Cl, Br, or I); cyano; trifluoromethyl; benzoic acid; substituted or unsubstituted alkyl, alkenyl, alkynyl, cycloalkyl, or cycloalkenyl; a group containing one or more cationic atoms or moieties or atoms or moieties that are cationic under physiological conditions, such as nitrogen-containing aromatic groups (e.g., pyridine), cyclic amines, amidines, $C_{1-20}$ alkyl amino or quaternized amino, preferably $C_{1-10}$ alkyl amino or quaternized amino, more preferably $C_{1-6}$ alkyl amino or quaternized amino.

W is preferably a group that minimizes or prevents aggregation and/or inhibits binding to duplex DNA compared to a cyanine not containing W.

In another embodiment, the cyanine has the structure:

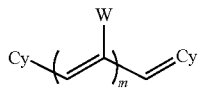

wherein,

Cy is a substituted or unsubstituted heteroaromatic moiety; and m and W are as defined above.

In some embodiments, Cy contains a first nitrogen substituted with a group containing one or more cationic groups. In preferred embodiments, this nitrogen is typically conjugated to the bridge.

In some embodiments, W is a group containing one or more cationic atoms or groups.

In other embodiments, the heteroaromatic ring and/or the bridge is substituted with one or more substituents which reduces the tendency of the cyanine to aggregate or prevents the cyanine from aggregating. The one or more substituents can prevent aggregation via steric effects (e.g., size of the substituent(s) decreases or prevents aggregation) and/or electronic effects (e.g., the electronic structure of the substituent(s) prevents aggregation). In some embodiments, the substituent(s) which reduces or prevents aggregation is a halogen, such as F, Br, Cl, or I or alkoxy, such as methoxy, ethoxy, propoxy, etc.

In other embodiments, the heteroaromatic ring contains an atom substituted with one more sterically bulky substituents. The sterically bulky substituents may prevent aggregation and/or prevent binding to duplex DNA. Non-limiting examples of such substituted atoms include a second heteroatoms, such as —NR, where R is a substituted or unsubstituted sterically bulk alkyl group, such as methyl, ethyl, isopropyl, isobutyl, sec-butyl, t-butyl, pentyl and isomers thereof, hexyl and isomers thereof, substituted or unsubstituted cyclohexyl groups; substituted or unsubstituted aryl groups; etc, or —CR$_{10}$R$_{11}$, wherein $R_{10}$ and $R_{11}$ are defined the same as R. In preferred embodiments, $R_{10}$ and $R_{11}$ are methyl groups.

In other embodiments, the cyanine has the formula above, wherein Cy is substituted with one or more groups which prevent aggregation and/or inhibit binding to duplex DNA, such as halogen, such as F, Cl, Br, or I; Cy contains a first nitrogen atom, conjugated to the bridge, which is substituted with a group containing one or more cationic groups, and Cy contains a group substituted with one or more sterically bulk groups as discussed above.

In still other embodiments, the heteroaromatic ring is substituted with one or more substituents which reduce the tendency of the cyanine to aggregate or prevent the cyanine from aggregating and/or inhibit binding to duplex DNA, the nitrogen heteroatom conjugated to the bridge is substituted with a group containing one or more cationic moieties, and at least one occurrence of W is a halogen, such as F, Cl, Br, or I or a group containing one or more cationic atoms or groups.

In another embodiment, the cyanine has the formula:

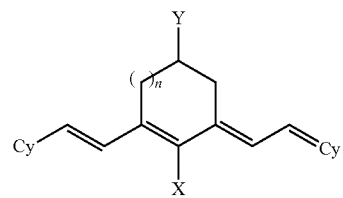

wherein Cy is as defined above, X and Y are as defined above for W, and n=0 (cyclopentyl ring) or 1 (cyclohexyl ring). In preferred embodiments, X and/or Y are groups that prevent or minimize aggregation and/or inhibit binding to duplex DNA. In some embodiments, the cyanine has the formula above, wherein if n=0 and Cy is a benzimidazole containing a second heteroatom, the second heteroatoms is not sulfur and/or X is not chlorine.

In some embodiment, the cyanines contain no functional groups which are negatively charged or which become negatively charged under physiological conditions. In other embodiments, the cyanines can contain one or more negatively charged groups and or groups that are negatively charged under physiological conditions provided the cyanine selectively binds quadruplex DNA as defined above.

In particular embodiments, the cyanine has the formula shown above, wherein each occurrence of Cy is selected from:

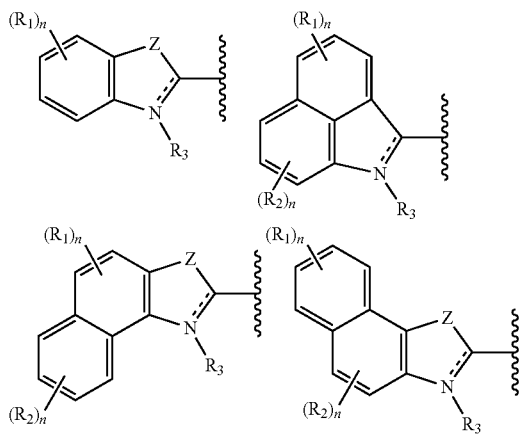

wherein n, as valence allows, is an integer from 0-4;

each occurrence of $R_1$ and $R_2$ is independently absent or selected from hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(═O)R", —C(═O)R', —C(═O)OR', —OC(═O)R', —O(CR'R")$_r$C(═O)R', —O(CR'R")$_r$NR"C(═O)R', —O(CR'R")$_r$NR"SO$_2$R', —OC(═O)NR'R", NR'C(═O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, r is an integer from 1 to 6;

each of $R_3$ is independently hydrogen, a group having no charge, such as $C_{1-20}$ alkyl, preferably $C_{1-10}$ alkyl, more preferably $C_{1-6}$ alkyl; a positively charged or group that can be made positively charged, such as $C_{1-20}$ alkyl amino or quaternized amino, preferably $C_{1-10}$ alkyl amino or quaternized amino, more preferably $C_{1-6}$ alkyl amino or quaternized amino;

Z is O, S, NR$_4$ or CR$_5$R$_6$; wherein R$_4$-R$_6$ are selected from hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(═O)R", —C(═O)R', —C(═O)OR', —OC(═O)R', —O(CR'R")$_r$C(═O)R', —O(CR'R")$_r$NR"C(═O)R', —O(CR'R")$_r$NR"SO$_2$R', —OC(═O)NR'R", —NR'C(═O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, and r is an integer from 1 to 6.

The double bonds are represented as dotted line (i.e., optional) depending on whether the Cy has a double bond within the ring (i.e., double bond to nitrogen resulting in four bonds to nitrogen and the nitrogen is positively charged) or the double bond is exocyclic (i.e., nitrogen has three bonds and is neutral).

In some embodiments, the cyanine has the formula:

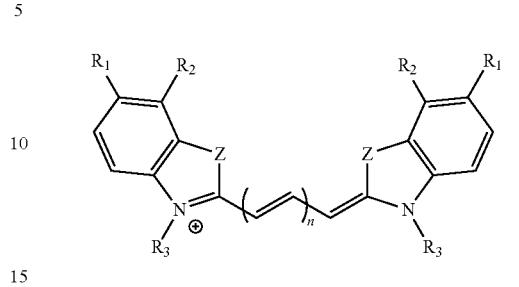

wherein $R_1$-$R_3$ and Z are as defined above and n is an integer from 0-4, preferably from 1-4, more preferably 1, 2, or 3. In some embodiments, Z is not sulfur. In some embodiments, $R_1$ is not carboxylic acid or —SO$_3$H.

In particular embodiments, the cyanine has the following structure:

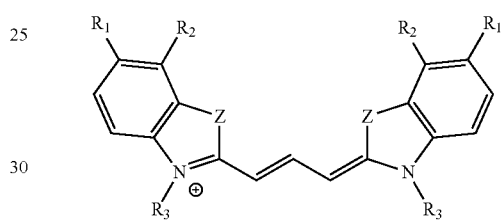

wherein $R_1$-$R_3$ and Z are as defined above. Specific compounds include:

26: $R_1$=H, $R_2$=H, $R_3$=CH$_2$CH$_2$CH$_2$N$^+$(CH$_3$)$_3$, Z=C(CH$_3$)$_2$;

27. $R_1$=C$_1$, $R_2$=H, $R_3$=CH$_2$CH$_2$CH$_2$N$^+$(CH$_3$)$_3$, Z=C(CH$_3$)$_2$;

28. $R_1$=Br, $R_2$=H, $R_3$=CH$_2$CH$_2$CH$_2$N$^+$(CH$_3$)$_3$, Z=C(CH$_3$)$_2$;

29. $R_1$=I, $R_2$=H, $R_3$=CH$_2$CH$_2$CH$_2$N$^+$(CH$_3$)$_3$, Z=C(CH$_3$)$_2$;

32. $R_1$, $R_2$=—(CH═CH)$_2$—, $R_3$=CH$_2$CH$_2$CH$_2$SO$_3^-$, Z=C(CH$_3$)$_2$;

33. $R_1$, $R_2$=—(CH═CH)$_2$—, $R_3$=CH$_2$CH$_2$CH$_2$CH$_2$SO$_3^-$, Z=C(CH$_3$)$_2$;

34. $R_1$=H, $R_2$=H, $R_3$=CH$_2$CH$_2$CH$_2$N$^+$(CH$_3$)$_3$, Z=O; or

35. $R_1$=H, $R_2$=H, $R_3$=CH$_2$CH$_2$CH$_2$N$^+$(CH$_3$)$_3$, Z=S;

The numbering system above corresponds to the synthetic scheme shown in Scheme 1.

In other embodiments, the compound has the formula:

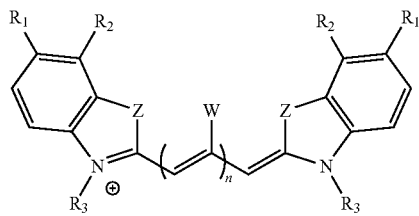

wherein $R_1$-$R_3$, Z, and W are as defined above and n is an integer from 0-4, preferably from 1-4, more preferably 1, 2, or 3. In some embodiments, R$_1$ is not —SO$_3$H. In some embodiments, W is not a carboxylic acid containing moiety.

In particular embodiments, the cyanine has the structure:

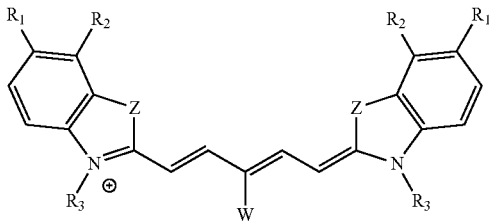

wherein R$_1$-R$_3$, Z, and W are as defined above. Specific compounds include:

42: R$_1$=H, R$_2$=H, R$_3$=CH$_2$CH$_2$CH$_2$N$^+$(CH$_3$)$_3$, Z=C(CH$_3$)$_2$; W=Cl;
43: R$_1$=H, R$_2$=H, R$_3$=CH$_2$CH$_2$CH$_2$N$^+$(CH$_3$)$_3$, Z=C(CH$_3$)$_2$; W=Br;
44: R$_1$=Br, R$_2$=H, R$_3$=CH$_2$CH$_2$CH$_2$N$^+$(CH$_3$)$_3$, Z=C(CH$_3$)$_2$; W=CH$_2$CH$_2$COOH;
45: R$_1$=Cl, R$_2$=H, R$_3$=CH$_2$CH$_2$CH$_2$N$^+$(CH$_3$)$_3$, Z=C(CH$_3$)$_2$; W=Cl;
46: R$_1$=C$_1$, R$_2$=H, R$_3$=CH$_2$CH$_2$CH$_2$N$^+$(CH$_3$)$_3$, Z=C(CH$_3$)$_2$; W=Br;
47: R$_1$=Br, R$_2$=H, R$_3$=CH$_2$CH$_2$CH$_2$N$^+$(CH$_3$)$_3$, Z=C(CH$_3$)$_2$; W=Cl;
48: R$_1$=Br, R$_2$=H, R$_3$=CH$_2$CH$_2$CH$_2$N$^+$(CH$_3$)$_3$, Z=C(CH$_3$)$_2$; W=Br;
49: R$_1$=I, R$_2$=H, R$_3$=CH$_2$CH$_2$CH$_2$N$^+$(CH$_3$)$_3$, Z=C(CH$_3$)$_2$; W=Cl;
50: R$_1$=I, R$_2$=H, R$_3$=CH$_2$CH$_2$CH$_2$N$^+$(CH$_3$)$_3$, Z=C(CH$_3$)$_2$; W=Br;
54: R$_1$=H, R$_2$=H, R$_3$=CH$_2$CH$_2$CH$_2$N$^+$(CH$_3$)$_3$, Z=O; W=Cl;
55: R$_1$=H, R$_2$=H, R$_3$=CH$_2$CH$_2$CH$_2$N$^+$(CH$_3$)$_3$, Z=O; W=Br;
56: R$_1$=H, R$_2$=H, R$_3$=CH$_2$CH$_2$CH$_2$N$^+$(CH$_3$)$_3$, Z=S; W=Cl; or
57: R$_1$=H, R$_2$=H, R$_3$=CH$_2$CH$_2$CH$_2$N$^+$(CH$_3$)$_3$, Z=S; W=Br;
58: R$_1$=F, R$_2$=H, R$_3$=CH$_2$CH$_2$CH$_2$N$^+$(CH$_3$)$_3$, Z=C(CH$_3$)$_2$, W=Cl;
59: R$_1$=F, R$_2$=H, R$_3$=CH$_2$CH$_2$CH$_2$N$^-$(CH$_3$)$_3$, Z=C(CH$_3$)$_2$, W=Br;
60. R$_1$=F, R$_2$=H, R$_3$=CH$_2$CH$_2$CH$_2$N$^-$(CH$_3$)$_3$, Z=C(CH$_3$)$_2$, W=CN;
SP-2-36. R$_1$=H, R$_2$=H, R$_3$=CH$_2$CH$_2$CH$_2$N$^+$(CH$_3$)$_3$, Z=C(CH$_3$)$_2$, W=4-pyridinyl;

The numbering system above corresponds to the synthetic scheme shown in Scheme 2.

In still other embodiments, the cyanine is an unsymmetrical cyanine. In some embodiments, if the cyanine is unsymmetrical, one of Cy is not isoquinoline. In particular embodiments, the unsymmetrical cyanine has the formula:

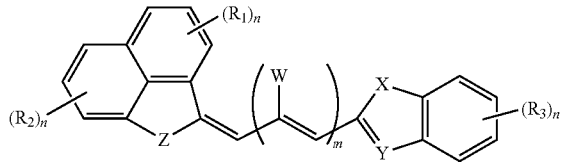

wherein, each occurrence of R$_1$, R$_2$, and R$_3$ is independently absent or selected from hydrogen; halogen (e.g., F, Cl, Br, and I); hydroxy, —OR'; —SR'; —NR'R"; nitro; cyano; carbonyl (e.g., aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR")); sulfonyl (including sulfate, sulfonamido, sulfamoyl and sulfonate); phosphoryl (including phosphonate and phosphinate); and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein R' and R" are individually hydrogen, alkyl, cycloalkyl, heterocyclyl, aryl, or arylalkyl, r is an integer from 1 to 6;

each occurrence of W on the bridge is independently hydrogen; halogen, such as F, Cl, Br, or I; cyano; trifluoromethyl; benzoic acid; substituted or unsubstituted alkyl, alkenyl, alkynyl, cycloalkyl, or cycloalkenyl; a group containing one or more cationic atoms or moieties or atoms or moieties that are cationic under physiological conditions, such as nitrogen-containing aromatic groups (e.g., pyridine), cyclic amines, amidines, C$_{1-20}$ alkyl amino or quaternized amino, preferably C$_{1-10}$ alkyl amino or quaternized amino, more preferably C$_{1-6}$ alkyl amino or quaternized amino; and X, Y, and Z are independently S, NR$_4$, or CR$_5$R$_6$, wherein each occurrence of R$_4$-R$_6$ is the same or different and is selected from hydrogen, a group having no charge, such as C$_{1-20}$ alkyl, preferably C$_{1-10}$ alkyl, more preferably C$_{1-6}$ alkyl; a positively charged group or group that can be made positively charged, such as C$_{1-20}$ alkyl amino or quaternized amino, preferably C$_{1-10}$ alkyl amino or quaternized amino, more preferably C$_{1-6}$ alkyl amino or quaternized amino.

In some embodiments, all occurrences of R$_1$-R$_3$ are hydrogen, X is C(CH$_3$)$_2$, Y is NR$_4$, wherein R$_4$ is a C$_{1-20}$, preferably C$_{1-10}$, more preferably C$_{1-6}$, more preferably C$_{1-4}$ alkyl quaternized amino, and Z is NR$_4$, wherein R$_4$ is C$_{1-20}$, preferably C$_{1-10}$, more preferably C$_{1-6}$, more preferably C$_{1-4}$ alkyl.

In a particular embodiment, the compound has the formula:

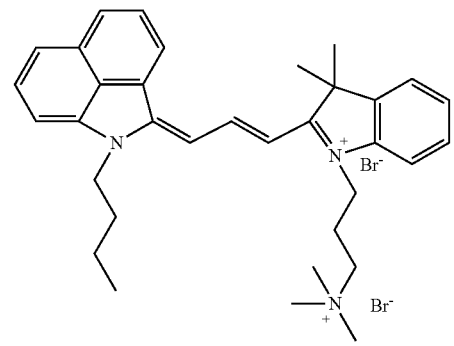

ZK-14

III. Pharmaceutical Compositions Containing the Cyanines

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof i. Nano- and Microparticles For parenteral administration, the one or more cyanines, and optional one or more additional active agents, can be incorporated into microparticles, nanoparticles, or combinations thereof that provide controlled release of the cyanines and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the cyanines and/or one or more additional active agents can be incorporated into polymeric microparticles which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives thereof, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more cyanines to a patient in need thereof. For intravenous or intraarterial routes, this can be accomplished using drip systems, such as by intravenous administration. For topical applications, repeated application can be done or a patch can be used to provide continuous administration of the cyanines over an extended period of time.

2. Injectable/Implantable Solid Implants

The cyanines described herein can be incorporated into injectable/implantable solid or semi-solid implants, such as polymeric implants.

In one embodiment, the cyanines are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the cyanines can be incorporated into a polymer matrix and molded, compressed, or extruded into a device that is a solid at room temperature. For example, the cyanines can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more cyanines from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the cyanines from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Formulations

Oral dosage forms, such as capsules, tablets, solutions, and suspensions, can for formulated for controlled release. For example, the one or more cyanines and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more cyanines and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more cyanines and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the cyanines and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit®RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit®L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof 1. Topical Formulations "Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents.

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more cyanines to a patient in need thereof. For topical applications, repeated application can be done or a patch can be used to provide continuous administration of the cyanines over an extended period of time.

D. Pulmonary Formulations

In one embodiment, the cyanines are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids.

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. The deep lung, or alveoli, are the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solutions is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the cyanines. An appropriate solvent should be used that dissolves the cyanines or forms a suspension of the cyanines. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the cyanines in the lungs and that the excipients that are present are present in amount that do not adversely affect uptake of cyanines in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

E. Other Active Agents

The cyanines described herein can be co-administered with one or more additional active agents, such as diagnostic agents, therapeutic agents, and/or prophylactic agents. Suitable classes of active agents include, but are not limited to:

Alkylating agents, such as nitrogen mustards (e.g., mechloroethamine, cyclophosphamide, Ifosfamide, melphalan, and chlorambucil), ethylenimines and methylmelamines (e.g., heaxmethylmelamine), alkyl sulfonates (e.g., thiotepa and busulfan) nitrosoureas (e.g., carmustine, lomustine, semustine, and streptozocin), and triazines (e.g., dacarbazine);

Antimetabolites, such as folic acid and analogs thereof (e.g., methotrexate), pyrimidine analogs (e.g., fluoracil, floxuridine, and cytarabine), purine analogs and related inhibitors (e.g., mercaptopurine, thioguanine, and pentostatin), Cytotoxic anticancer agents, such as paclitaxel;

Cytostatic and/or cytotoxic agents such as anti-angiogenic agents such as endostatin, angiostatin, thalidomide;

Analgesics, such as opioid and non-opioid analgesics; and

Vaccines containing cancer antigens or immunomodulators such as cytokines to enhance the anti-cancer activity;

Natural products, such as vinca alkaloids (e.g., vinblastine and vincristine), epipodophyllotoxins (e.g., etoposide and tertiposide), antibiotics (e.g., dactinomycin, daunorubicin, doxorubicin, bleomycin, plicamycin, and mitomycin), enzymes (e.g., L-asparaginase), and biological response modifiers (e.g., interferon alpha);

Proteasome inhibitors, such as lactacystin, MG-132, and PS-341;

Tyrosine kinase inhibitors, such as Gleevec®, ZD 1839 (Iressa®), SH268, genistein, CEP2563, SU6668, SU1 1248, and EMD121974;

Retinoids and synthetic retinoids, such as bexarotene, tretinoin, 13-cis-retinoic acid, 9-cis-retinoic acid, .alpha.-difluoromethylornithine, ILX23-7553, fenretinide, and N-4-carboxyphenyl retinamide;

Cyclin-dependent kinase inhibitors, such as flavopiridol, UCN-01, roscovitine and olomoucine;

COX-2 inhibitors include, such as celecoxib, valecoxib, and rofecoxib;

Prenylprotein transferase inhibitors, such as R1 15777, SCH66336, L-778,123, BAL9611 and TAN-1813;

Hormones and antagonists, such as adrenocorticosteroids (e.g., prednisone), progestins (e.g, hydroxyprogesterone caproate, medroxyprogesterone acetate, and megestrol acetate), estrogens (e.g., diethylstilbestrol and ethinyl estradiol), antiestrogen (e.g., tamoxifen), androgens (e.g., testosterone propionate, fluoxtnesterone, antiandrogen), and gonadotropin-releasing hormone analogs;

Sigma-2 receptor agonists, such as CB-64D, CB-184 and haloperidol;

HMG-CoA reductase inhibitors, such as lovastatin, simvastatin, pravastatin, fluvastatin, atorvastatin and cerivastatin;

HIV protease inhibitors, such as amprenavir, abacavir, CGP-73547, CGP-61755, DMP-450, indinavir, nelfinavir, tipranavir, ritonavir, saquinavir, ABT-378, AG 1776, and BMS-232,632;

Proteins, such as insulin, and

Miscellaneous compounds, such as platinum coordination complexes (e.g., cisplatin and carboplatin), anthracenedione (e.g., mitoxantrone), substituted urea (hydroxyurea), methyl hydrazines (e.g., procarbazine), and adrenocortical suppressants (e.g., mitotane and aminogluethimide).

The one or more cyanines and the one or more additional active agents can be formulated in the same dosage form or separate dosage forms. Alternatively, the one or more additional active agents can be administered simultaneously or almost simultaneously in different dosage forms. If in separate dosage units, the one or more cyanines and the one or more additional active agents can be administered by the same route of administration or by different routes of administration. For example, the one or more cyanines and the one or more additional active agents can both be administered parenterally, or one can be administered parenterally and one orally.

If the one or more cyanines and the one or more active agents are administered sequentially, the second agent to be administered is administered typically less than 6 hours following administration of the first agent, preferably less than 4 hours after the first agent, more preferably less than 2 hours after the first agent, more preferably less than 1 hour after the first agent, most preferably less than 30 minutes after administration of the first agent, and most preferably immediately after administration of the first agent "Immediately", as used here, means less than 10 minutes, preferably less than 5 minutes, more preferably less than 2 minutes, most preferably less than one minute.

The cyanines and the one or more additional active agents can be formulated for controlled release, for example, immediate release, delayed release, extended release, pulsatile release, and combinations thereof. In one embodiment, the one or more cyanines are formulated for immediate release and the one or more additional agents are formulated for delayed, extended, or pulsatile release. In another embodiment, the one or more cyanines are formulated for delayed, extended, or pulsatile release and the one or more additional active agents are formulated for immediate release. In still another embodiment, the one or more cyanines and the one or more additional active agents are independently formulated for delayed, extended, or pulsatile release.

IV. Methods of Making the Cyanine Compounds

The cyanine compounds can be synthesized using techniques known in the art. In some embodiments, the cyanine compounds were prepared via synthetic scheme 1.

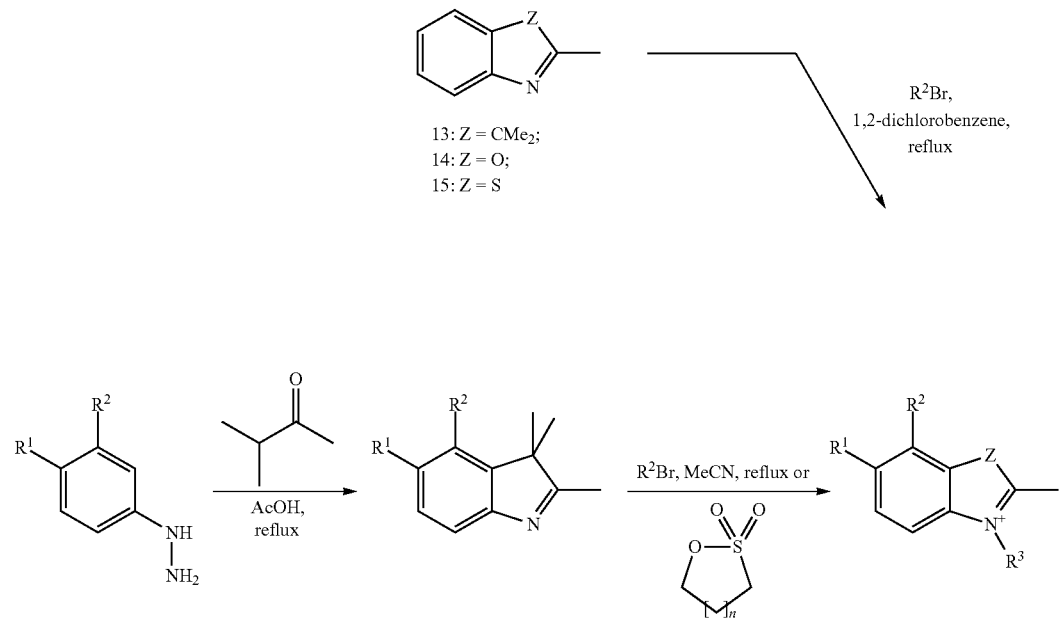

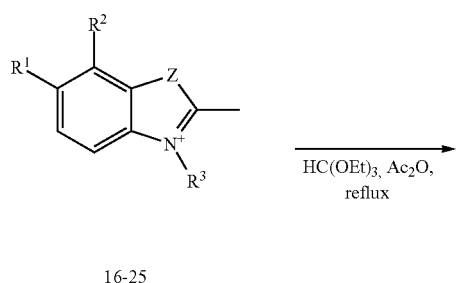
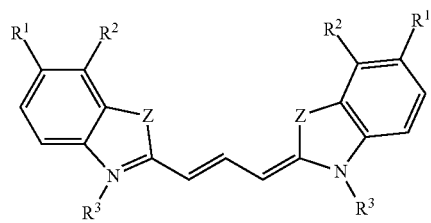

26: $R^1$ = H, $R^2$ = H, $R^3$ = $CH_2CH_2CH_2N^+Me_3$, Z = $CMe_2$;
27: $R^1$ = Cl, $R^2$ = H, $R^3$ = $CH_2CH_2CH_2N^+Me_3$, Z = $CMe_2$;
28: $R^1$ = Br, $R^2$ = H, $R^3$ = $CH_2CH_2CH_2N^+Me_3$, Z = $CMe_2$;
29: $R^1$ = I, $R^2$ = H, $R^3$ = $CH_2CH_2CH_2N^+Me_3$, Z = $CMe_2$;
30: $R^1$ = COOH, $R^2$ = H, $R^3$ = $CH_2CH_2CH_2N^+Me_3$, Z = $CMe_2$;
31: $R^1$ = $SO_3H$, $R^2$ = H, $R^3$ = $CH_2CH_2CH_2N^+Me_3$, Z = $CMe_2$;
32: $R^1$, $R^2$ = —(CH=CH)$_2$—, $R^3$ = $CH_2CH_2CH_2SO_3$-, Z = $CMe_2$;
33: $R^1$, $R^2$ = —(CH=CH)$_2$—, $R^3$ = $CH_2CH_2CH_2CH_2SO_3$-, Z = $CMe_2$;
34: $R^1$ = H, $R^2$ = H, R = $CH_2CH_2CH_2N^+Me_3$, Z = O;
35: $R^1$ = H, $R^2$ = H, $R^3$ = $CH_2CH_2CH_2N^+Me_3$, Z = S

An alternative scheme for preparing the cyanine compounds is shown in Scheme 2.

Scheme 2: Alternate synthetic route for preparing cyanine compounds

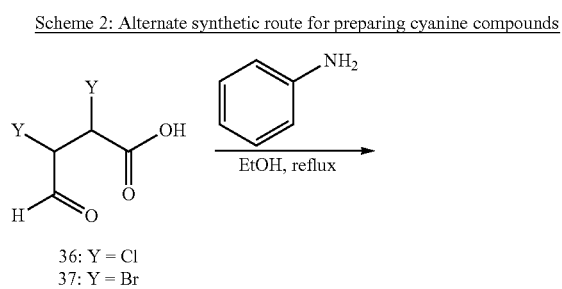

36: Y = Cl
37: Y = Br

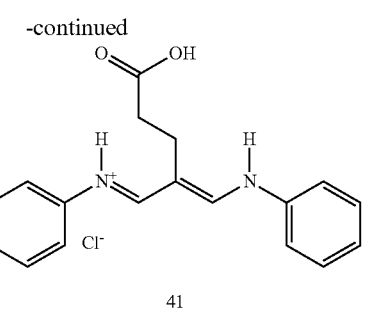

41

-continued

38: Y = Cl
39: Y = Br

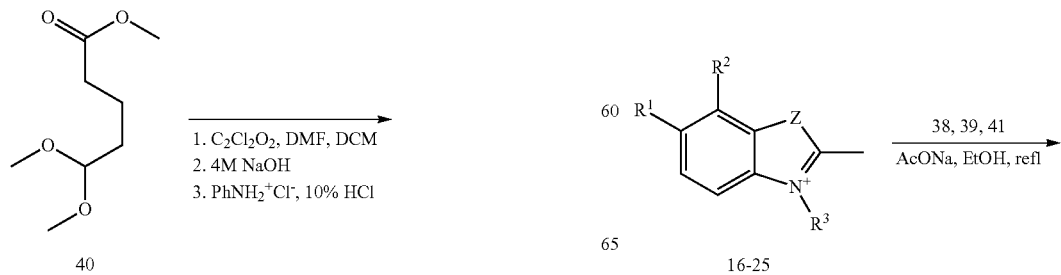

16-25

37

-continued

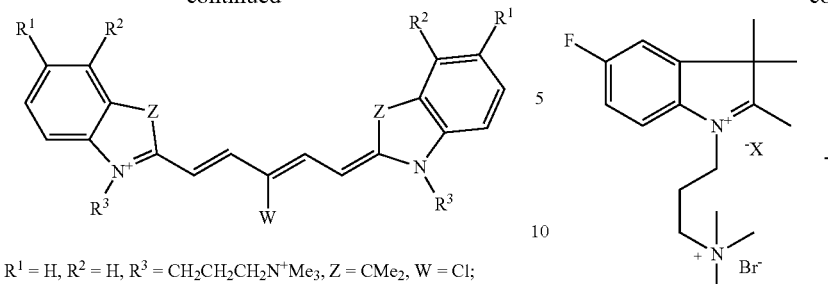

42: $R^1 = H$, $R^2 = H$, $R^3 = CH_2CH_2CH_2N^+Me_3$, $Z = CMe_2$, $W = Cl$;
43: $R^1 = H$, $R^2 = H$, $R^3 = CH_2CH_2CH_2N^+Me_3$, $Z = CMe_2$, $W = Br$;
44: $R^1 = H$, $R^2 = H$, $R^3 = CH_2CH_2CH_2N^+Me_3$, $Z = CMe_2$, $W = CH_2CH_2COOH$;
45: $R^1 = Cl$, $R^2 = H$, $R^3 = CH_2CH_2CH_2N^+Me_3$, $Z = CMe_2$, $W = Cl$;
46: $R^1 = Cl$, $R^2 = H$, $R^3 = CH_2CH_2CH_2N^+Me_3$, $Z = CMe_2$, $W = Br$;
47: $R^1 = Br$, $R^2 = H$, $R^3 = CH_2CH_2CH_2N^+Me_3$, $Z = CMe_2$, $W = Cl$;
48: $R^1 = Br$, $R^2 = H$, $R^3 = CH_2CH_2CH_2N^+Me_3$, $Z = CMe_2$, $W = Br$;
49: $R^1 = I$, $R^2 = H$, $R^3 = CH_2CH_2CH_2N^+Me_3$, $Z = CMe_2$, $W = Cl$;
50: $R^1 = I$, $R^2 = H$, $R^3 = CH_2CH_2CH_2N^+Me_3$, $Z = CMe_2$, $W = Br$;
51: $R^1 = SO_3H$, $R^2 = H$, $R^3 = CH_2CH_2CH_2N^+Me_3$, $Z = CMe_2$, $W = Cl$;
52: $R^1 = SO_3H$, $R^2 = H$, $R^3 = CH_2CH_2CH_2N^+Me_3$, $Z = CMe_2$, $W = Br$;
53: $R^1 = SO_3H$, $R^2 = H$, $R^3 = CH_2CH_2CH_2N^+Me_3$, $Z = CMe_2$, $W = CH_2CH_2COOH$;
54: $R^1 = H$, $R^2 = H$, $R^3 = CH_2CH_2CH_2N^+Me_3$, $Z = O$, $W = Cl$;
55: $R^1 = H$, $R^2 = H$, $R^3 = CH_2CH_2CH_2N^+Me_3$, $Z = O$, $W = Br$;
56: $R^1 = H$, $R^2 = H$, $R^3 = CH_2CH_2CH_2N^+Me_3$, $Z = S$, $W = Cl$;
57: $R^1 = H$, $R^2 = H$, $R^3 = CH_2CH_2CH_2N^+Me_3$, $Z = S$, $W = Br$

Additional compounds include those listed above, except W=H.

Scheme 3.

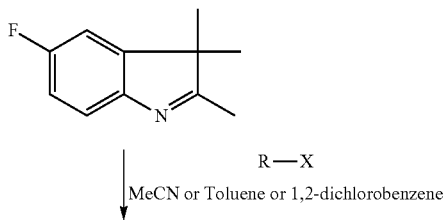

38

-continued

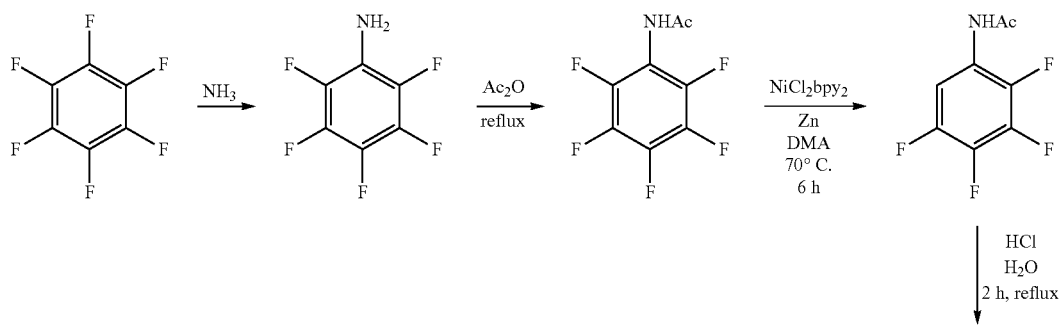

$X = Cl, Br, CN$
T4: $n = 2$, $X = Cl$
T5: $n = 2$, $X = Br$

Scheme 4.

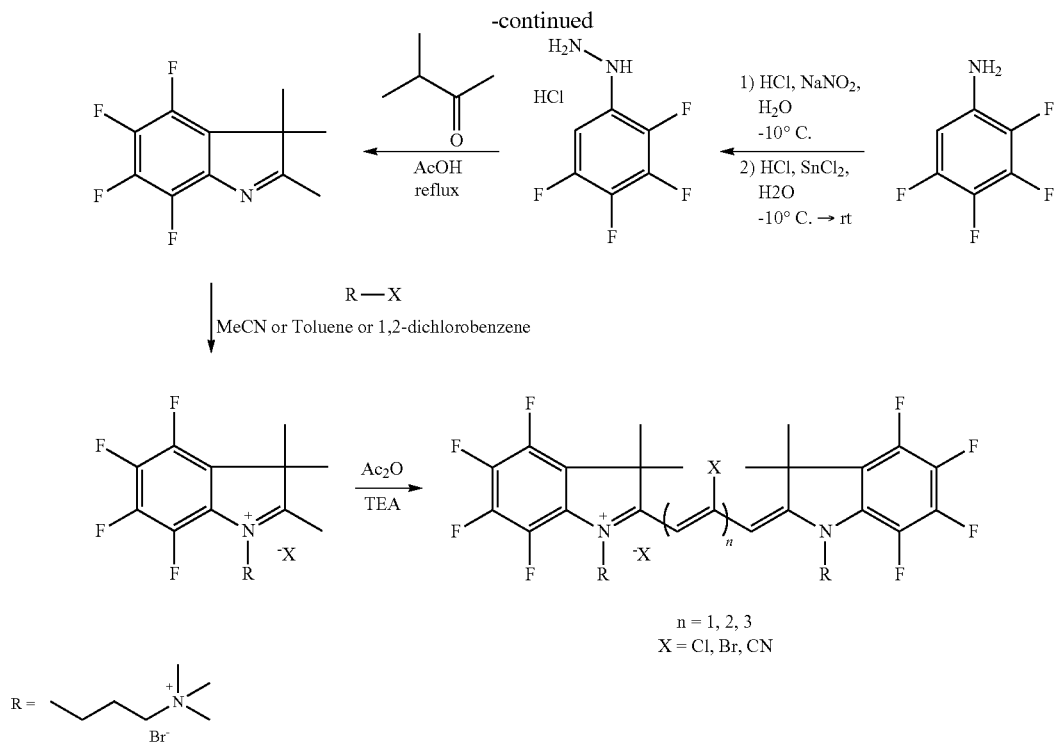

n = 1, 2, 3
X = Cl, Br, CN

V. Methods of Using the Cyanine Compounds

DNA Binding

Small molecules and proteins can be chemically tailored to bind to the minor and major grooves of DNA. If a sufficiently strong interaction is formed, it may be possible to block access to the hydrogen-bonds, electrostatic interactions, van der waals interactions, and/or shape complementarity required to prevent a particular protein from binding. In some cases, it may be possible to induce topological or conformational shifts so large that the groove width or even the bending of the strand will not conform to normal cellular activity. For these reasons, DNA has been an attractive drug target.

Current DNA targeting drugs on the market include Pentamidine, Berenil, and Trabectadin. These drugs target double stranded DNA by blocking in the minor groove in *T. Brucei* parasites, intercalating between base pairs of *T. Brucei* kinetoplast DNA, and alkylating in the minor groove of cancer DNA, respectively. Other DNA targeting drugs have been investigated. Most of these drugs are designed to bind in the minor groove, by intercalating or bis-intercalating, or interact with the phosphate backbone. Unfortunately most of these drugs have been rejected due to poor solubility or selectivity, unacceptable toxicity, and/or the development of resistance.

G-Quadruplex Complexes

The G-quadruplex forms by interstrand or intrastrand guanines hydrogen bonding with each other around a cation in two or more stacked guanine tetrads. DNA sequences commonly investigated when considering quadruplex structures include Human Telomere (HT), c-Myc, c-kit, bcl2, and kras. Quadruplex structures will form readily in G-rich single stranded DNA sequences when cations such as $K^+$ and $Na^+$ are available, so the high salt environment in the nucleolus enables guanine-rich sequences to form the quadruplex structure. Each of these sequences may form specific structures dependent on the direction of the phosphate backbone: parallel, antiparallel, or hybrid structures of parallel and antiparallel. The guanines are oriented in only the anti conformation in the parallel motif, and a combination of syn and anti conformations in hybrid and antiparallel motifs. Each of the structures have loops with varying numbers of base pairs and relative position along the tetrads.

Using the differences between each quadruplex structure as well as the unique available interactions that separates quadruplex DNA from double stranded DNA, compounds can target the quadruplex by loop binding, end stacking, groove binding, and/or intercalation. Loop binding involves indirect associations both polar and nonpolar. This typically involves stabilizing the loops, but results in no significant change on the overall DNA conformation. Loop binding is typically a weak enough interaction that it is only observed as a secondary binding mode at high concentration of ligand.

End stacking utilizes primarily non-polar $\pi$-$\pi$ stacking on the top or bottom tetrad. End stacking may shift the conformation; however, the shift, if any, is generally not significant. Groove binding occurs when the compounds slide between the phosphate backbone, and can significantly alter the conformation by pushing the Hoogsteen bonds out of place. Finally, a compound may intercalate a quadruplex if it slides between the tetrads, greatly altering the structure, and forming $\pi$-$\pi$ interactions with the guanines. This is likely too energetically expensive to occur as the core cation must be displaced and the strands and loops get in the way in many quadruplex motifs.

Most compounds that bind to quadruplex DNA such as TmPyP4, RHPS4, and Braco19 are shown to end stack. They primarily contain conjugated ring systems intended to $\pi$-$\pi$ stack with the tetrads, as shown below.

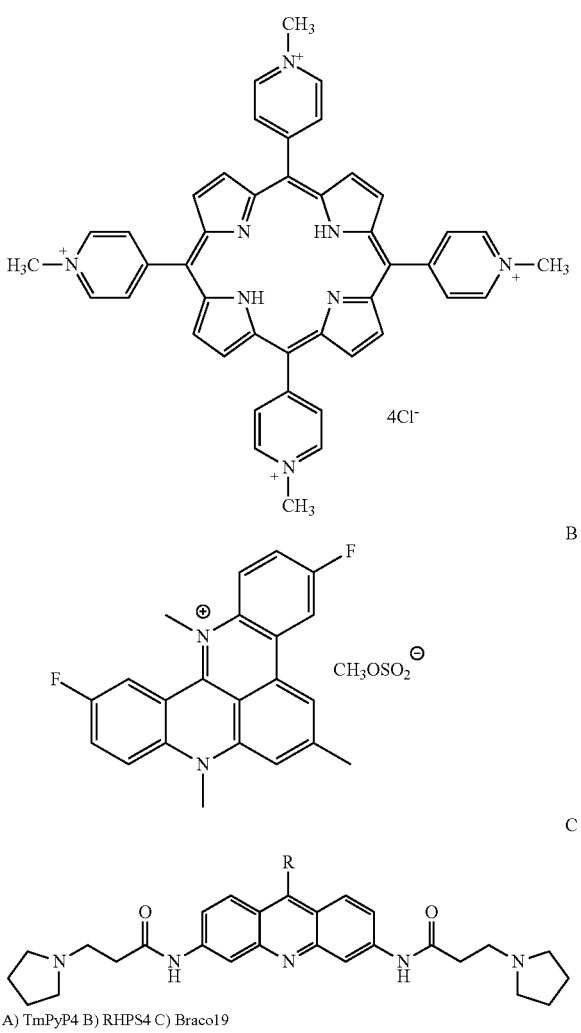

A) TmPyP4 B) RHPS4 C) Braco19

Although most quadruplex binding compounds whose binding method has been established are believed to end stack, groove binding compounds are expected to be more specific in living cells due to more nucleic acid recognition by hydrogen bonding.

Quadruplex-specific binding compounds have been the focus of many studies, and have had some success. Several drugs have been developed to target G-quadruplex DNA in cancer cells and have entered clinical studies. However, it has been determined that their mechanism of action involves binding with proteins in the nucleolus, not DNA.

G-Quadruplex as a Target for Treating Cancer

In the early 1990's, a correlation between G-quadruplex formation and cancer cells was established. Upon further investigation the telomere and several oncogene promoter regions were identified as sequences that could form the quadruplex motif in vitro. Cancer cells are termed such because they over-transcribe their DNA, causing over-replication of those cells and certain proteins within them. Additionally, the normal apoptosis command is either blocked or cannot be followed (depending on the type of cancer). Quadruplex-binding drugs may inhibit cancer cell growth in various ways. However, current evidence suggest that they induce the apoptosis command in cell lines by forcing the command to be followed by different cues such as starving the cells of necessary proteins. When transcription is halted, the DNA cannot copy itself nor can it form mRNA to create proteins necessary for cell functions.

In cancer cells, the nuclear protein telomerase is overexpressed, leading to a lengthened G-rich single stranded tail to each chromosome. Telomerase is present but inactive in normal cells. Under normal conditions of cell senesence or apoptosis, the amount of telomerase present would decrease until the cell cannot copy the DNA anymore, and the cell would die. Due to over-production of the protein, the apoptosis command never occurs because there is always a long enough telomere to copy DNA. The ends of the telomere are single stranded, so it must assume a conformation that stabilizes the hydrophobic nucleic acids. In normal cells, the telomere is short and does not need to alter it's conformation, but in cancer cells the conformation is the hybrid quadruplex motif seen in vitro. If the quadruplex structure can be stabilized in the telomere, then it would cost too much energy for the cell to unwind it in order to add more telomere. Thus the cancer cells could die selectively, as normal cells' telomeres do not form quadruplex structures.

C-myc and c-kit are oncogenes and their promoter regions contain G-rich sequences. They exist in all cells, but are overexpressed in cancer cells. Normally, they are read only when necessary to produce MYC and KIT proteins respectively, or to regulate gene expression. However, in cancer cells, these sequences are separated from normal Watson and Crick hydrogen bonds more often to be transcribed regularly. Though these regions are double stranded, they have been found to form quadruplex structures in order to stabilize the constant replication. If the separate strands can be stabilized such that they cannot be read by transcription proteins, not only would overexpression cease but expression would entirely cease, starving the cells of MYC and KIT proteins. The cancer cells would selectively die as normal c-myc and c-kit do not form quadruplex structures.

Quadruplex Specificity of Cyanines

The compounds described herein exhibit increased specificity for quadruplex DNA compared to duplex DNA. This selectivity can be evaluated using a variety of analytical techniques, such as thermal melting, surface plasma resonance (SPR) spectroscopy, circular dichroism, fluorescence, and/or mass spectrometry. "Selective for quadruplex DNA", as used herein, means that the cyanine selectively binds quadruplex DNA structures at least 2, 4, 6, 8, 10, 15, 20, 25, 30, 35, 40, 45, 50, 75, 100, 150, 200, 250, 500, 750, or 1000 times higher than duplex DNA. The range includes all values between 2 and 1000. In some embodiments, the cyanine does not bind duplex DNA to an extent that can be measured by thermal analysis (e.g., thermal melting), surface plasma resonance ("SPR") spectroscopy, circular dichroism, fluorescence, and/or mass spectrometry.

The results described in the example show the particular trends of chemical properties that assist in optimizing the process of developing cyanines to bind selectively to quadruplex DNA compared to duplex DNA. Compounds with negative charges (or overall charge of less than +3) exhibited weak binding and little or no selectively for quadruplex DNA.

Based on the benzothiozole cyanine dye results, the two methyl groups on the indole appear to inhibit duplex binding. The benzothiozole rings lay in the minor groove of duplex DNA as sulfur interacts with the nucleotide bases and the positive ring nitrogen interacts with the phosphate backbone. The methyl groups prohibit interactions in the groove, but maintain the conjugation required to bind to the quadruplex DNA. In both benzothiozole and indole cyanine dye complexes, binding affinity and stabilization is dependent on length and the ability for the compound to fit the shape of the quadruplex. Hydrophobic substituents replacing positively charged groups weakens binding due to their hydrophobicity and lessened polar interactions.

Trimethine dihalogenated cyanines exhibited a trend in binding affinity and stabilization: the larger the halogen on the ring systems, the stronger the binding. No specific trends were observed for the two pentamethine monohalogenated compounds, but the pentamethine trihalogenated compounds indicate a trend based on the central methine-linked halogen: binding is preferred with a smaller halogen on the linker. The compounds synthesized thus far only contain bromine and chlorine on the linker, but bromine-containing linkers seem to stabilize quadruplex DNA better than those with chlorine. When comparing pentamethine dyes with varying numbers of halogens, there is a clear increase in stabilization of hTelo with additional bromines.

In general, circular dichroism (CD) titrations show minimal change in the DNA region, indicating loop binding or end stacking. The induced CD seen in the compound region of the trimethine dihalogenated dyes is unique to that family of compounds. The trimethine nonsubstituted (MH-4) and the pentamethine disubstituted (E-48) cyanine dyes both show no induced CD in the compound regions. Additionally, the compound-only CD titration show no induced CD, so it is likely that these cyanines stack on the quadruplex in a unique way.

UV-Vis, thermal melting, fluorescence, SPR, and ITC experimental methods support binding specifically to c-myc parallel quadruplex over human telomere hybrid quadruplex, and to both quadruplex sequences over duplex DNA as shown in the Examples below. This sequence specificity is rarely seen in other compounds.

Use of Cyanines for Selectively Binding Quadruplex DNA Complexes to Treat Cancer The compounds described herein are cyanines which selectively bind quadruplex DNA complexes. In some embodiments, the cyanines typically have either three, five, or seven carbon linkers or bridges, and the ring systems, e.g., indoles and benzothiozoles, and ring nitrogens are substituted in attempt to prevent or minimize duplex binding. In some embodiments, the cyanines described herein are halogen-substituted cyanines which bind strongly to human telomere and/or c-Myc and have a low binding affinity for, or do not bind to, duplex DNA.

Cyanine dyes are known to aggregate which can adversely affect their efficacy as anti-cancer agents. In some embodiments, the cyanines described herein contain one or more substituents which reduce or prevent aggregation of the cyanines. In one embodiments, the one or more substituents are halogens, such as F, Cl, Br, and/or I. Generally, the greater the number of halogen substituents, the less likely the cyanine is to aggregate. In particular embodiments, the halogen is substituted on the Cy moiety (e.g., $R_1$ and/or $R_2$ is halogen) or on the bridge (i.e., W is halogen). In other embodiments, $R_1$ and/or $R_2$ and W are halogen. In still other embodiments, $R_1$, $R_2$, and W are halogens.

In still other embodiments, one or more of $R_1$, $R_2$, and W are halogens and Z is $—CR_5R_6$, wherein $R_5$ and $R_6$ are lower alkyl, particularly methyl.

In still other embodiments, one or more of $R_1$, $R_2$, and W are halogens, Z is $—CR_5R_6$, wherein $R_5$ and $R_6$ are lower alkyl, particularly methyl, and $R_3$ is a group containing one or more cationic groups, such as trimethyl ammonium moieties.

In still other embodiments, the cyanine are functionalized to increase the number of positive charges. As the number of cationic groups increases, the selectivity for quadruplex DNA increases. Uptake in vivo can also improve as the number of positive charges increases. For example, in some embodiments, $R_3$ is a functional group containing one or more cationic moieties, such as trimethylammonium groups and the bridge contains one or more groups containing one or more cationic moieties (e.g., W is a substituent containing one or more cationic groups). The number of carbons in the chain containing the one or more cationic moieties can vary but is typically from 1-10, preferably from 1-6, more preferably from 1-4, most preferably from 1-3 carbons.

The compounds describe herein can be used to treat a variety of cancers, including, but not limited to, cancers of the brain, lung, liver, ovaries, testicles, cervix, prostate, blood, pancreas, stomach, epithelial cells, connective tissue, embryonic tissue, and combinations thereof. The cyanines can also be used to treat cancers that have metastasized to or from the organs above.

The dose of the compounds to be administered is dependent on a number of factors including the age and weight of the patients, the particular type of cancer to be treated, and/or the dosage form used to administer the compound and can readily be determined by the attending physician. Exemplary dosages include 0.001 mg/kg/day to 500 mg/kg/day, 0.001 mg/kg/day to 250 mg/kg/day, 0.001 mg/kg/day to 100 mg/kg/day, 0.01 mg/kg/day to 100 mg/kg/day, and 0.01 mg/kg/day to 50 mg/kg/day. In some embodiments, the cyanines are present in amount effective to interrupt DNA replication in cells that express G-quadruplex DNA and cause cancer cell death. The cyanines can be used to effectively treat or prevent diseases characterized by the expression or overexpression of quadruplex DNA complexes.

In some embodiments, the cyanines are able to accumulate in the nucleus where they selectively bind quadruplex DNA and interrupt cell replication and cause cell death. Protocols for evaluating accumulation in the nucleus are known in the art and can be modified as needed to assay the cyanines described herein. Suitable protocols include, but are not limited to, biodistribution assays, which can determine localization site, metabolic pathway, and excretion method of the cyanines.

Other Applications

The cyanines described herein can also be used as diagnostic agents. The cyanines described herein may fluoresce above 600 nm and thus can be used as probes to monitor DNA activity in vivo. Near-infrared wavelengths are less harmful to living cells and can penetrate cells walls without detecting residual fluorescence coming from the cell. The cyanines described herein can be used as fluorphores to monitor dimer binding in the duplex minor groove. The cyanines can also be used to in clinical studies for cancer and tumor detection as the cyanines may be retained by tumor cells for days to weeks but are readily excreted from healthy cells since the compounds selectively bind quadruplex DNA complexes.

EXAMPLES

Materials

Three DNA sequences were used: Human Telomere (HTelo), c-myc, and Duplex (Integrated DNA Technologies, San Diego, Calif.). The sequences are shown below:

HTelo G4 (22 mers):

(SEQ ID NO: 1)
5'-AGG GTT AGG GTT AGG GTT AGG G-3' c-myc (19 mers):

(SEQ ID NO: 2)
5'-AGG GTG GGG AGG GTG GGG A-3'

Duplex:

(SEQ ID NO: 3)
5'-CGG AAT TCG CTT TTG CGA ATT CGC-3'

The concentration of each DNA sample mixed with MilliQ water was determined by UV-Vis at 260 nm using their extinction coefficients. Quadruplexes from Human Telomere (Tel22) and c-myc were prepared by heating the corresponding oligonucleotides at 90° C. for 5 minutes in a 10 mM Tris/50 mM KCl buffer at pH 7.5 and then cooling to room temperature (to favor the intramolecular folding).

All of the cyanine compounds were synthesized and purified at Georgia State University, Atlanta, Ga. (USA) (see Schemes 1, 2 and Equation 1). Stock solutions of the compounds were prepared in MilliQ water. They were diluted to the appropriate concentration in the working buffer prior to use.

The buffer used was 10 mM Tris base (Fischer Scientific, Fairlawn, N.J.), 50 mM Potassium Chloride (Fischer Scientific, Fairlawn, N.J.), with the pH adjusted to 7.5 with Hydrochloric Acid (Fischer Scientific, Fairlawn, N.J.).

Methods

Thermal Melting UV-Vis Absorbance Analysis

DNA folding and unfolding (melting) can be measured using absorbance at a constant wavelength of 260 nm for duplex DNA and 295 nm for quadruplex DNA while the temperature is increased, for example from 25° C. to 95° C. At these wavelengths, the resulting curves decrease in absorbance for quadruplex and increase for duplex DNA. Buffer solution and presence of DNA-binding compounds alter the $T_m$ melting temperature, or midpoint between fully folded and unfolded. An increase in melting temperature in the presence of DNA-binding compounds indicates a stabilizing effect of the compound on the DNA structure. Though a large increase in $T_m$ does not necessarily imply strong binding affinity, a correlation has been established, and assessing $\Delta T_m$ (change in melting temperature) values can be used as a screening tool.

Fluorescence Analysis

Atoms absorb energy and can emit it as heat (vibrational relaxation), fast light emission (fluorescence), or slow light emission (phosphorescence). Most of the cyanines described herein fluoresce in response to near-infrared wavelengths of light absorption. As the cyanines bind to DNA, π-π stacking and hydrogen bonding is altered leading to a change in fluorescence emission. This change can be measured in direct correlation to DNA binding. In some cases an approximate binding constant can be determined from measuring fluorescence enhancement as DNA is titrated into a solution of fluorescent compound. Fluorescent enhancement, or the maximum emission divided by the minimum emission of the titration (compound saturated with DNA divided by free compound) at a fixed wavelength is useful to compare DNA affinity between a family of compounds.

Circular Dichroism Analysis of DNA and Compound Regions

Chiral atoms rotate circularly polarized light in either dextrorototory or levorototory directions. DNA consists of chiral atoms in the nucleotide bases, so different DNA structures rotate light in different patterns. That is to say, A form, B form, Z form, triplex, and quadruplex DNA can be differentiated using circular dichroism (CD), and by studying spectral patterns, favorable DNA binding structures can be determined by observing conformational shifts as a cyanine is titrated into a solution of DNA. DNA rotates light generally below 300 nm, but the cyanines described herein can also rotate light if their hydrogen bonds are altered enough into a chiral complex conformation. These rotational shifts can be observed in the compound region, near its maximum absorbance wavelength.

Surface Plasmon Resonance Spectroscopy

An SPR chip contains DNA, immobilized on a thin gold film by biotin or other linkages. A laser shines on the reverse side of the film, measuring the refractive index at a particular laser angle of only the gold film and anything attached to it. That is, when a buffer solution flows over the film, the laser records a constant refractive index. When a compound or protein is flowed with this buffer, it may bind to the linked DNA, causing a shift in refractive index and laser angle required to measure the film. By this method, the exact binding can be recorded by the SPR sensogram by comparing the change of refractive index due to the change of contents bound to the chip.

Binding Stoichiometry Analysis by Mass Spectrometry

Mass spectrometry is a variable technique in which ionized gas molecules are analyzed based on their masses and charges to attain precise molecular weights. In the experiments described below, electrospray ionization (ESI) is utilized. This method pushes a liquid solution through a tube surrounded by a current: a taylor cone is formed, ionizing then pushing the liquid solution into smaller and smaller gasseous particles. The particles fly through a quadrupole and time-of-flight sorter so that the detector will retrieve the particles at different times based on their mass to charge ratio (m/z). ESI is a gentle enough technique that compounds will remain bound to the DNA through their flight, and the resulting spectra can be analyzed to find exact binding stoichiometries of those ligands.

Isothermal Calorimetry

DNA binding is dependent on enthalpy and entropy, components of the Gibbs free energy. Isothermal calorimetry measures the heat absorbed (endothermic binding) or released (exothermic binding) in binding at the μcalorie level. By examining the thermodynamics of different compounds, compounds can be analyzed to determine what factors favor quadruplex over duplex DNA binding. Enthalpy and binding constants are determined from measuring the heat change when compound is injected into a DNA solution, and the equations $$\Delta G = \Delta H - T\Delta S$$

$$\Delta G = -RT \ln K$$

are used to calculate entropy and Gibbs free energy.

Example 1

Synthesis of Fischer Bases 7-12

A mixture of 4-substituted phenylhydrazine hydrochloride 1-6 (4.47 mmol) and 3-methyl-2-butanone (0.6 mL, 5.61 mmol) was dissolved in glacial acetic acid (15 mL), and then heated under reflux for 8 h under nitrogen. The solvent was evaporated in vacuo. The residue was dissolved in methylene chloride ($CH_2Cl_2$) (30 mL) and washed with 10% aqueous $Na_2CO_3$ (2×30 mL), dried over $Na_2SO_4$, and the solvent was evaporated to afford 7-12 as an oil. The product was used in the next reaction without further purification.

5-Bromo-2,3,3-trimethylindolenine (8): Yield 90%, 1H NMR (400 MHz, CDCl3): δ, ppm: 7.38 (m, 3H), 2.25 (s, 3H), 1.28 (s, 6H).

Example 2

Synthesis of Salts 22 and 23

Toluene (50 mL), indolenine 12 (0.0623 mol), and 1,3-propanesultone (1,4-butane sultone) (0.0935 mol) were heated under reflux for 18 h. The reaction mixture was allowed to cool to room temperature. The resulting pink crystals were filtered and washed with acetone (3×10 mL). The filtered product was crystallized from a solution of methanol (MeOH) and diethyl ether ($Et_2O$). The crystals were collected and dried in vacuo.

Example 3

Synthesis of Salts 16-20

A mixture of 7-10, 13 (31.4 mmol) and 3-bromopropiltrimetilammonium bromide (9.0 g, 34.5 mmol) was refluxed in acetonitrile (100 mL) for 72 hrs under nitrogen atmosphere. The reaction was cooled to room temperature, stayed overnight and then obtained precipitate was collect by filtration, washed with acetone and diethyl ether.

Compound 18: Yield 10.7 g, 25.4 mmol, 81%. M.p. 225-227° C. $^1$HNMR (400 MHz, DMSO-$d_6$), δ: 1.57 (s, 6H), 2.27 (s, 9H), 3.02 (s, 3H), 3.83 (t, J=8.0 Hz, 2H), 4.57 (t, J=8.0 Hz, 2H), 7.61 (m, 2H), 7.88 (t, J=5.6 Hz, 1H). $^{13}$CNMR (100 MHz, DMSO-$d_6$): δ 15.2, 22.0, 25.5, 30.6, 52.3, 54.3, 63.9, 115.6, 123.5, 128.8, 129.3, 140.9, 141.7, 197.7.

Example 4

Synthesis of Salts 21, 24, and 25

Base 11, 14, 15 (16.7 mmol) was added to (3-bromopropyl)-trimethylammonium bromide (4.36 g, 16.7 mmol) and refluxed in toluene (100 mL) for 72 hrs under nitrogen atmosphere. The liquid was decanted leaving a red residue. The residue was suspended in acetone and filtered. The product was crystallized from isopropanol. Additional amounts of product were isolated by adding acetone to the isopropanol solution.

The product 21 was obtained as white crystals: 7.6 g, 91%, m.p. 248-250° C.; $^1$HNMR (400 MHz, $D_2O$): δ 1.64 (s, 6H), 2.56 (t, J=4.8 Hz, 2H), 3.28 (s, 9H), 3.33 (s, 3H), 3.77-3.85 (m, 2H), 4.62 (t, J=8.4 Hz, 2H), 7.67 (d, J=8.4 Hz, 1H), 8.01-8.13 (m, 2H).

Example 5

Synthesis of Tricarbocyanine Dues 26-35

A mixture of salt 16-25 (50 mmol), triethylorthophormate (150 mmol) were refluxed for 45 minute in acetic anhydride under nitrogen atmosphere and then cooled to room temperature. The mixture was keep overnight; obtained precipitate was filter off, washed ethanol, and diethyl ether and dried.

The product 31 was obtained with 92% yield. M.p. 295-297° C.; $^1$HNMR (400 MHz, $D_2O$), δ: 1.66 (s, 12H), 2.26 (t, J=6.0 Hz, 4H), 3.09 (s, 18H), 3.44-3.54 (m, 4H), 4.14 (t, J=7.2 Hz, 4H), 6.44 (d, J=13.2 Hz, 2H), 7.28 (d, J=8.4 Hz, 2H), 7.74 (d, J=8.4 Hz, 2H), 7.83 (s, 2H), 8.50 (t, J=13.2 Hz, 1H). $^{13}$CNMR (100 MHz, $D_2O$), δ: 20.9, 21.2, 30.2, 40.8, 49.5, 53.2, 63.1, 103.7, 111.1, 120.0, 126.7, 139.9, 141.5, 143.6, 153.0, and 176.4.

Example 6

Synthesis of Compounds 38 and 39

Mucochloric acid 36 (mucobromic acid 37) (0.059 mol) was dissolved by heating in 40 mL ethanol, then solution of aniline (11 g, 0.118 mol) in 40 mL ethanol rapidly added. Mixture heated under stirring until evolution of carbon dioxide ceased. Solution became golden. Golden yellow crystals of the product form and collect by filtering the cooled solution. Product crystallized from ethanol.

The product 38 was obtained with 88% yield. $^1$HNMR (400 MHz, DMSO-$d_6$), δ: 7.34 (d, J=7.6 Hz, 2H), 7.51 (t, J=7.6 Hz, 4H), 7.67 (d, J=8.0 Hz, 4H), 9.49 (s, 2H), 11.84 (br. s, 2H).

Example 7

Synthesis of Compound 41

Anhydrous dimethylformamide (1.01 mL, 13 mmol) and oxalyl chloride (1.26 g, 10 mmol) were added sequentially into 30 mL anhydrous dichloromethane (DCM) in an acetone/dry ice bath. The mixture was allowed to warm to room temperature over 15 min. Methyl 5,5-dimethoxyvalerate 40 (881 mg, 5 mmol) was then added dropwise to the reaction solution followed by heating at 70° C. for 2 h, allowing the DCM to evaporate. The resulting yellow oil was dissolved in 5 mL of 4 M NaOH and was heated at 70° C. for 1 h. Before it use, the aniline was converted to his corresponding chloride salts on a 10 mmol scale by dissolving the aniline in acetone and precipitating its salt by addition of excess concentrated aqueous HCl. After removing the solvent under vacuum, the appropriate aniline chloride salt (10 mmol), dissolved in 5 mL water, was added to the basic, crude reaction solution and was allowed to stir at room temperature for 1 or more hours, until the reaction was complete. The final malonaldehyde dianil hydrochloride salt was precipitated as a light yellow solid after the addition of 5 mL of 10% aqueous HCl and was collected by filtration.

The product 41 was above 95% pure and used directly in the dye synthesis without further purification if not mentioned specifically. Yield 50%, m. p. 215-217° C. $^{13}$CNMR (100 MHz, DMSO$_{d6}$), δ: 18.4, 32.8, 111.2, 118.8, 125.8, 129.2, 141.2, 158.0, 174.6.

Example 8

Synthesis of Pentacarbocyanines 42-57

A mixture of salt (2 equivalent), Vilsmeier reagent (1 equivalent), and sodium acetate (3 equivalent) were refluxed for 6 hrs in anhydrous ethanol under nitrogen atmosphere and then cooled to room temperature. The mixture was concentrated dryness under vacuum, dissolve in deionized water and target compound was isolate by column chromatography on reverse phase (methanol:water 1:5).

For example was obtained 48 with 77.6% yield. M.p. 232-234° C.; $^1$HNMR (400 MHz, DMSO$_{d6}$): δ 1.76 (s, 12H), 2.18 (t, J=7.1 Hz, 4H), 3.12 (s, 18H), 3.55-3.65 (m, 4H), 4.24 (t, J=7.0 Hz), 6.34 (d, J=13.2 Hz, 2H), 7.60 (d, J=8.6 Hz, 2H), 7.66 (d, J=8.6 Hz, 2H), 8.06 (s, 2H), 8.60 (d, J=13.2 Hz); $^{13}$CNMR (400 MHz, DMSO$_{d6}$), δ: 20.66, 26.46, 41.37, 49.79, 52.35, 62.25, 102.70, 113.74, 116.99, 118.22, 126.03, 131.24, 140.93, 143.72, 150.42, 174.34.

Example 9

Characterization of Cyanine Dye-DNA Complexes

Thermal Melting

The selectivity of a given cyanine for quadruplex DNA can be evaluated using thermal melting. The data is shown in Table 1. The number in parentheses next to the compound number corresponds to the compound number in Schemes 1 and 2.

Halogens linked to the indole ring system greatly increased stabilization of these compounds. As seen in Table 1, cyanines 26, MH-4, and its chloro-27 (A-138), bromo-28 (MH-5), and iodo-29 (A-134) derivatives show increased quadruplex stabilization (structures shown below) as the size of the halogen increases with little or no binding to duplex DNA. 4:1 ratios were evaluated to due to assumed binding site saturation based on presumed two-site binding.

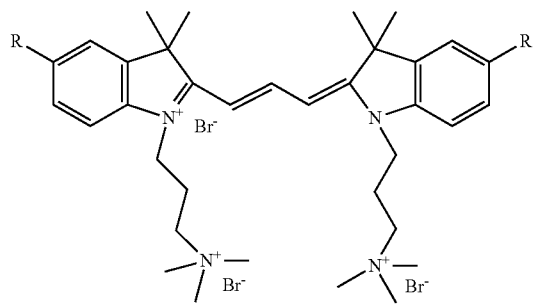

26; MH-4: R=H, 27; A-138: R=Cl, 28; MH-5: R=Br, 29; A-134: R=I

In general, these three-carbon linkers increase the change in T$_m$ as the substituent increases in atomic radius. However, the chloro (27, A-138) and bromo (28, MH-5) substituents stabilize approximately equally. The similar family of compounds with a five-carbon linker and only one halide substituent also has increased the change in thermal melting points.

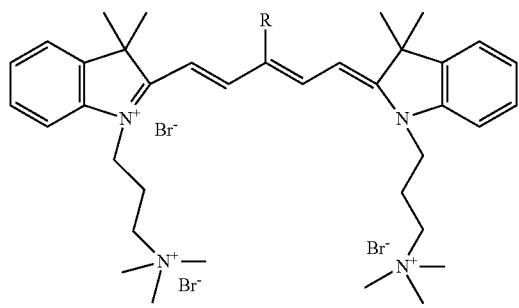

42; A-20: R = Cl, 43; A-C8: R = Br

TABLE 1

Change in Thermal Melting Points

| (R) | Human Telomere (HT) | | | | Duplex | | | |
|---|---|---|---|---|---|---|---|---|
| | 1:1 | 2:1 | 4:1 | 6:1 | 1:1 | 2:1 | 4:1 | 6:1 |
| MH2 (31) | 1.5 | 1.1 | 0.6 | 1.2 | | | | |
| MH4 (26) | 1.6 | 4.1 | 8.7 | 13.7 | 0 | 0.9 | -0.2 | 1.8 |
| MH5 (28) | 1 | 5.2 | 14.2 | 23.7 | -0.1 | -1.0 | -1.0 | -0.1 |
| A-C8 (43) | 2.0 | 4.6 | 11.6 | 15.6 | 0.0 | -1.1 | 0.9 | -0.2 |
| A-20 (42) | 2.6 | 6.0 | 12.2 | 13.2 | 0 | 0.9 | 0.9 | 2.8 |
| A-21 (51) | 0.0 | 0.1 | -0.4 | 0.2 | | | | |
| A-80 (30) | 0.6 | 1.1 | 2.6 | 7.2 | | | | |
| A-100 (44) | 0.1 | 0.2 | 1.2 | 1.2 | | | | |
| A-134 (19) | 2.6 | 6.6 | 17.2 | 20.8 | 1.0 | 1.1 | 1.1 | * |
| A-138 (17) | 3.0 | 7.0 | 14.6 | * | 0.0 | 0.0 | -1.0 | * |
| A-146 (45) | * | 11.0 | 12.0 | 16.1 | -1.0 | 0.1 | -0.8 | 2.3 |
| A-148 (46) | 3.1 | 8.6 | 14.8 | * | | | | |
| A-149 (47) | 2.6 | 4.6 | 10.2 | * | | | | |
| A-150 (48) | 3.0 | 6.7 | 17.7 | 20.2 | 2.0 | 1.2 | 1.2 | 1.2 |
| A-160 (49) | 1.0 | 5.2 | 11.7 | 17.8 | | | | |
| A-161 (50) | 4.1 | 9.2 | 16.2 | 21.7 | | | | |
| E-4 | 1.0 | 1.6 | -3.9 | * | | | | |
| E-6 | 0.6 | 0.1 | 0.2 | * | | | | |
| E-8 | 0.0 | -0.4 | -1.4 | -4.3 | | | | |
| E-46 | 0.0 | -0.4 | -0.4 | -3.8 | -1.0 | -0.9 | 0.0 | -0.8 |
| E-48 | 1.5 | 2.5 | 15.6 | 11.6 | * | 1.1 | -0.7 | 0.0 |

The standard deviation in the experiment is approximately 1.0. Therefore, it is evident for a number of cyanines, such as MH4, MH5, A-C8, A-20, A-134, and A-138, that these compounds selectively bind to quadruplex DNA with little or no binding to duplex DNA.

The data also shows that the presence of a group containing one or more cationic groups on the nitrogen results in significant selectivity for quadruplex DNA. This is further evidenced by compounds E-4, E-6, and E-8, which contain —(CH$_2$)$_3$Ph, —(CH$_2$)$_3$, and —(CH$_2$)$_3$Ph groups, respectively, attached to the nitrogen in the heteroaromatic ring. These groups do not contain a cationic group and show little or no selectivity for quadruplex DNA. In fact, E-4 and E-8 exhibited slightly negative values indicating a minor destabilization of the quadruplex structure.

E-46 and E-48 are pentamethine cyanines, having unsubstituted heteroaromatic rings and unsubstituted bridge (E-46) and bromine substituted heteroaromatic rings and unsubstituted bridge (E-48, dihalogenated cyanine). The data shows that pentamethine monohalogenated cyanines generally exhibit weaker binding than trimethine halogenated cyanines. However, the dihalogenated pentamethine cyanines exhibit comparable quadruplex stabilization compared to the corresponding trimethine cyanine.

Thermal melting studies were also performed on compounds T4 and T5 (Scheme 2) and ZK-14 and SP-2-36. The data is shown in Table 2.

TABLE 2

Thermal Melting (Δ° C.) of compound with Quadruplex vs. Duplex DNA

| | Quadruplex DNA | | | | Duplex DNA | | | |
| --- | --- | --- | --- | --- | --- | --- | --- | --- |
| | 1:1 ratio | 1:2 ratio | 1:4 ratio | 1:6 ratio | 1:1 ratio | 1:2 ratio | 1:4 ratio | 1:6 ratio |
| T4 | 1.6 +/− 0.2 | 3.3 +/− 0.4 | 8.0 +/− 0.7 | 10.7 +/− 0.7 | 0.4 +/− 0.4 | 0.5 +/− 0.4 | 0.9 +/− 0.5 | 1.2 +/− 0.7 |
| T5 | 2.7 +/− 0.3 | 6.2 +/− 0.4 | 13.3 +/− 0.4 | 16.9 +/− 0.6 | 0.1 +/− 0.2 | 0.8 +/− 0.4 | 0.8 +/− 0.4 | 0.9 +/− 0.4 |
| ZK-14 | 1.9 +/− 0.3 | 7.7 +/− 1.1 | 20.4 +/− 1.0 | 26.0 +/− 0.5 | 0.6 +/− 0.1 | 0.8 +/− 0.3 | 2.7 +/− 0.1 | 2.8 +/− 0.3 |
| SP-2-36 | 0.9 +/− 0.1 | 1.4 +/− 0.2 | 3.5 +/− 0.8 | 4.4 +/− 0.5 | 0.2 +/− 0.3 | 0.5 +/− 0.5 | 0.5 +/− 0.3 | 0.6 +/− 0.3 |

Figure 1B:
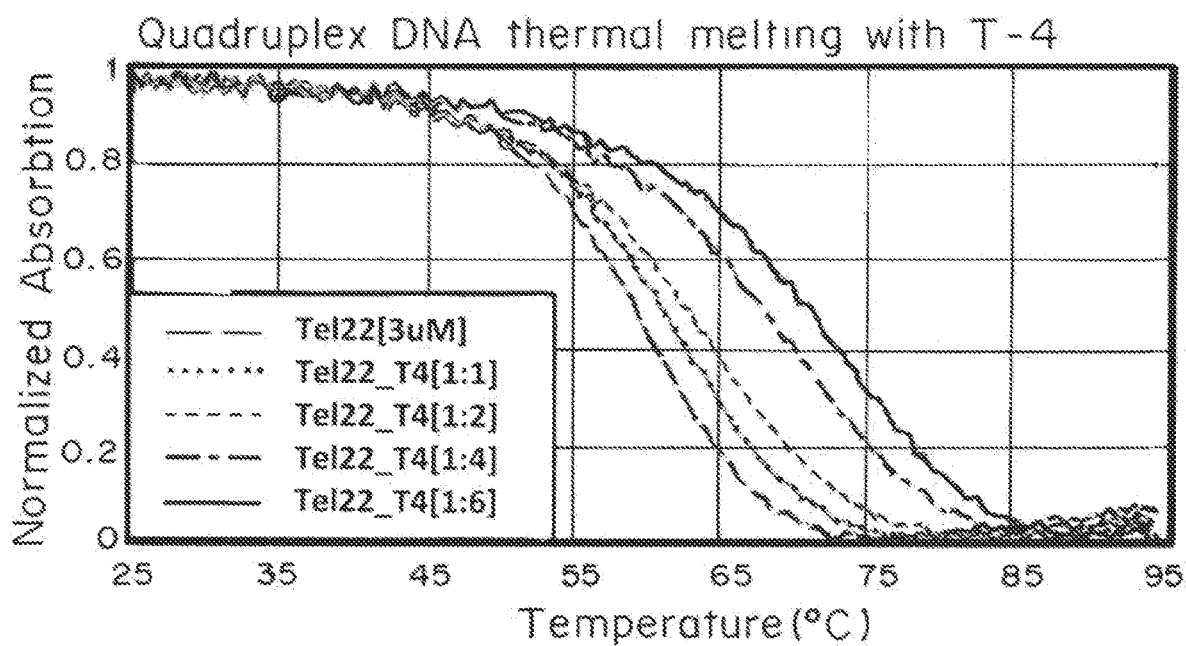
Figure 2A:
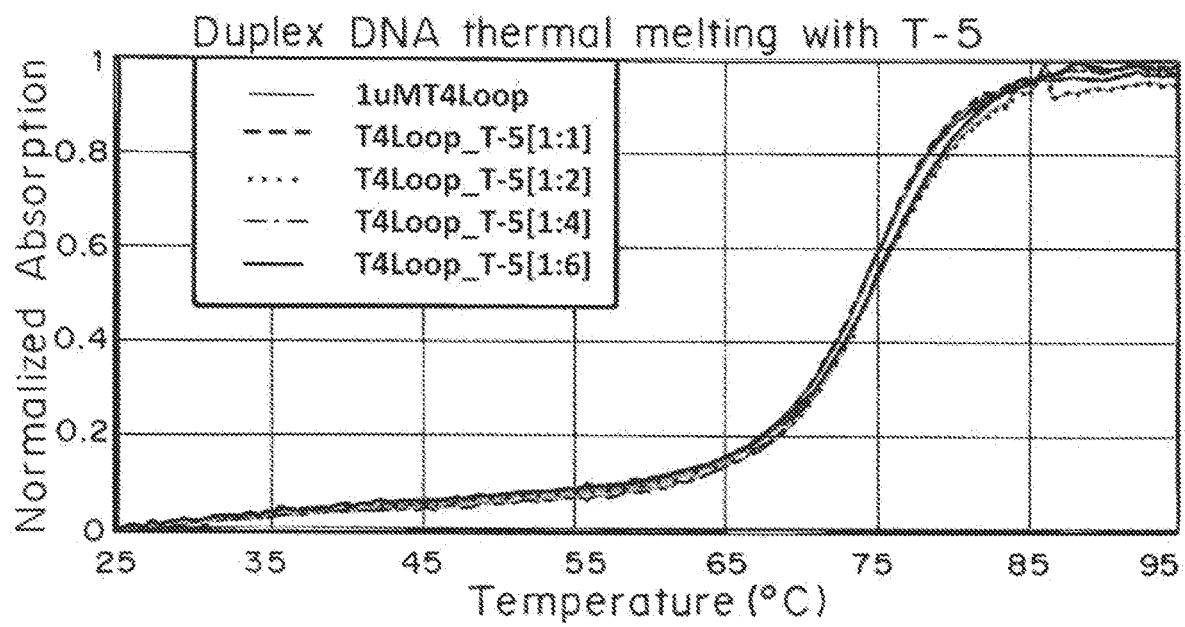
FIGS. 2A and 2B are graphs showing absorption as a function of temperature (° C.) for complexes formed between compound T-5 with duplex DNA (FIG. 2A) and quadruplex DNA (FIG. 2B). The lowest temperature plot is for free DNA and the highest temperature plot is for the highest ratio of compound to DNA.
Figure 2B:
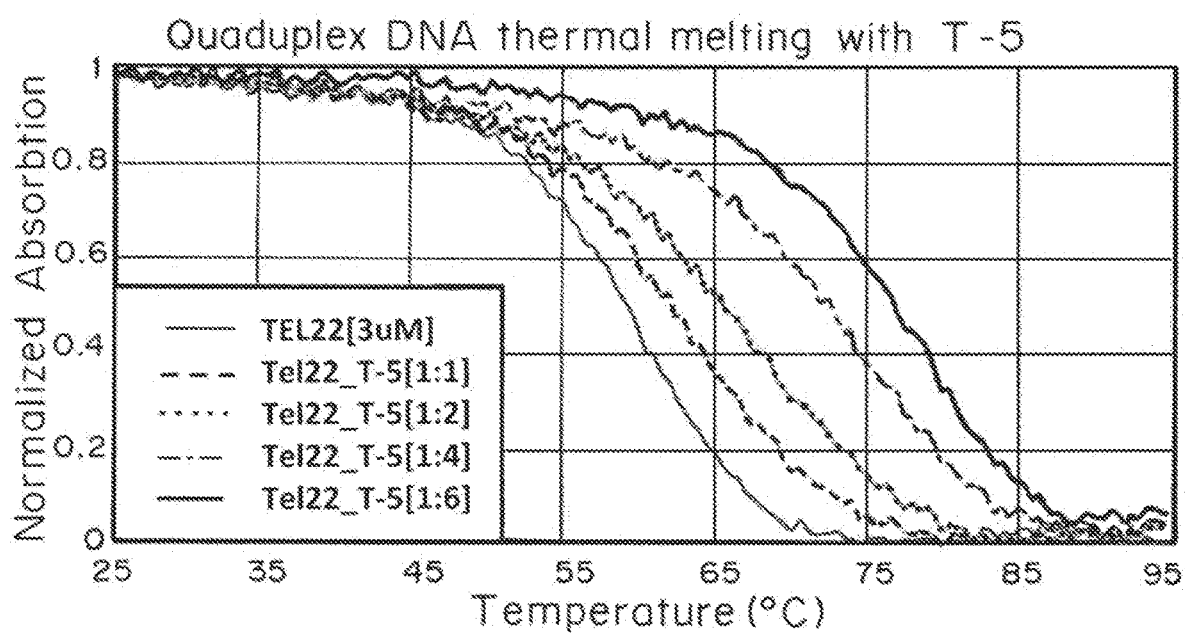
Figure 3A:
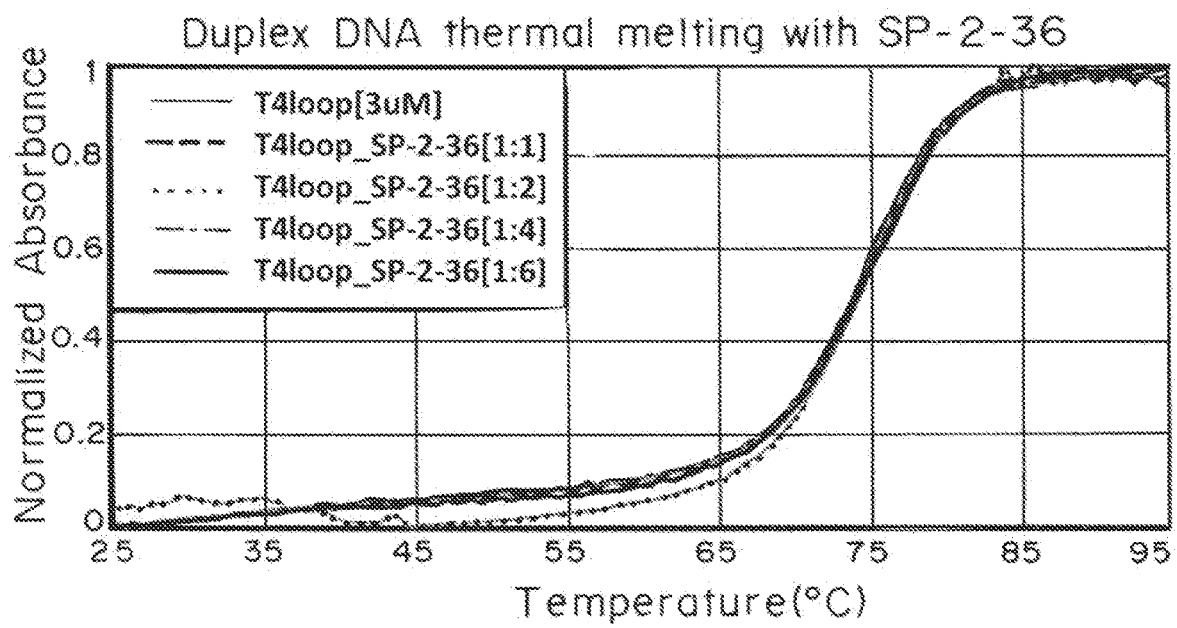
FIGS. 3A and 3B are graphs showing absorption as a function of temperature (° C.) for complexes formed between SP-2-36 with duplex DNA (FIG. 3A) and quadruplex DNA (FIG. 3B). The lowest temperature plot is for free DNA and the highest temperature plot is for the highest ratio of compound to DNA.
Figure 3B:
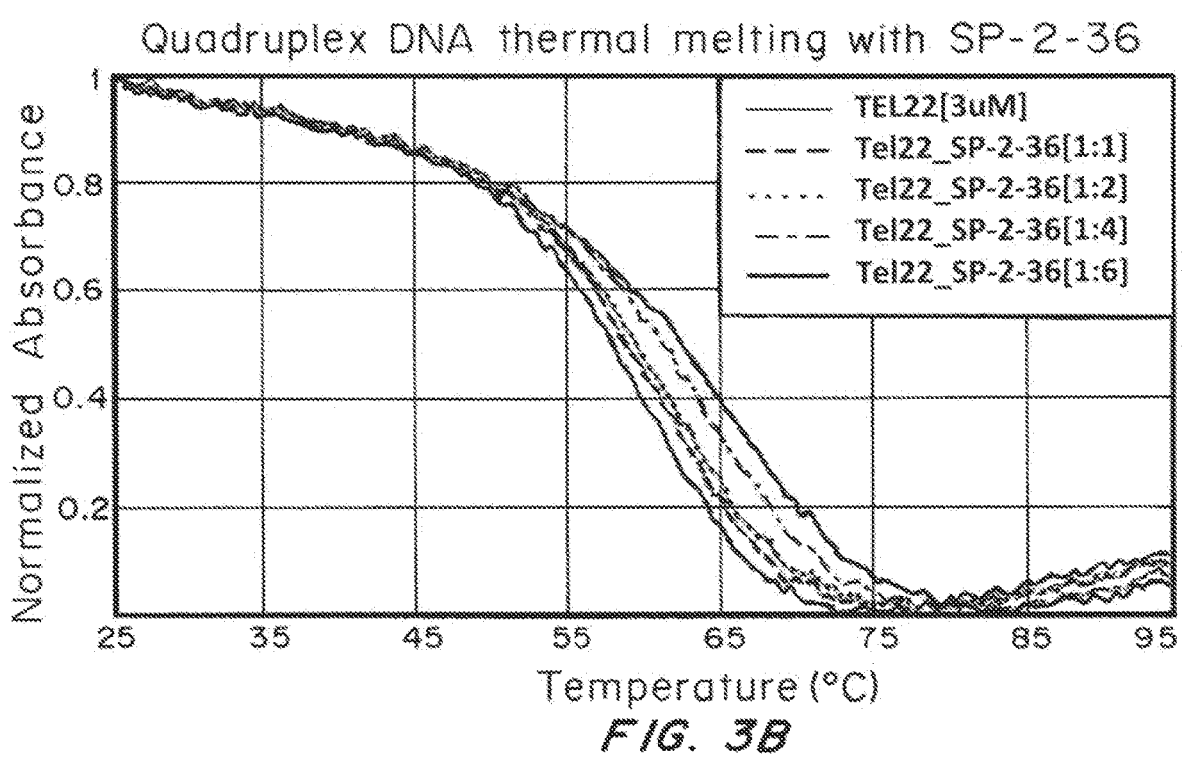
Figure 4A:
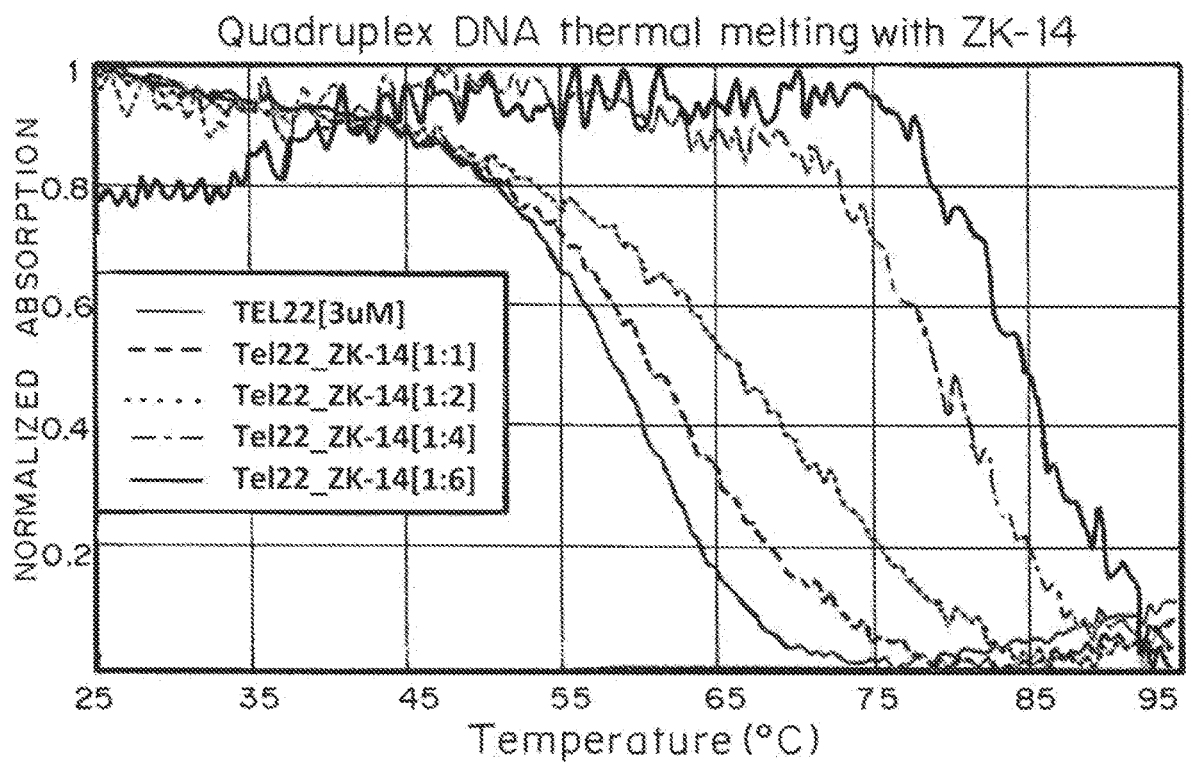
FIGS. 4A and 4B are graphs showing absorption as a function of temperature (° C.) for complexes formed between compound ZK-14 with duplex DNA (FIG. 4A) and quadruplex DNA (FIG. 4B). The lowest temperature plot is for free DNA and the highest temperature plot is for the highest ratio of compound to DNA.
Figure 4B:
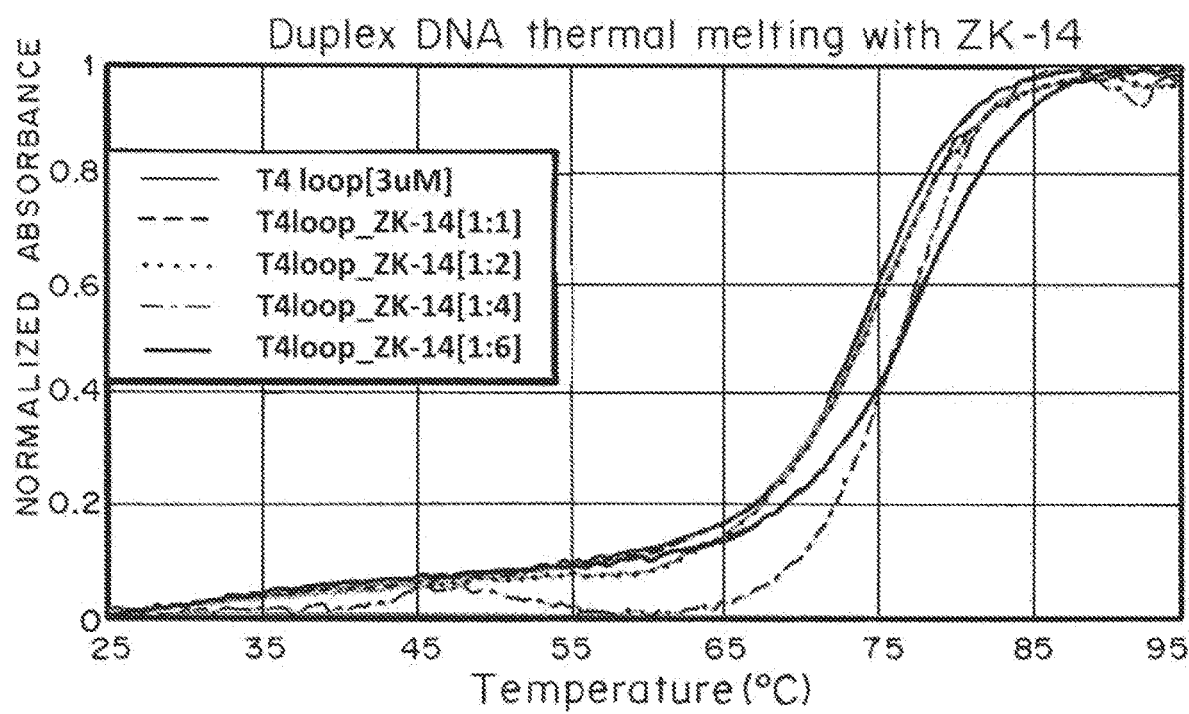
Figure 5A:
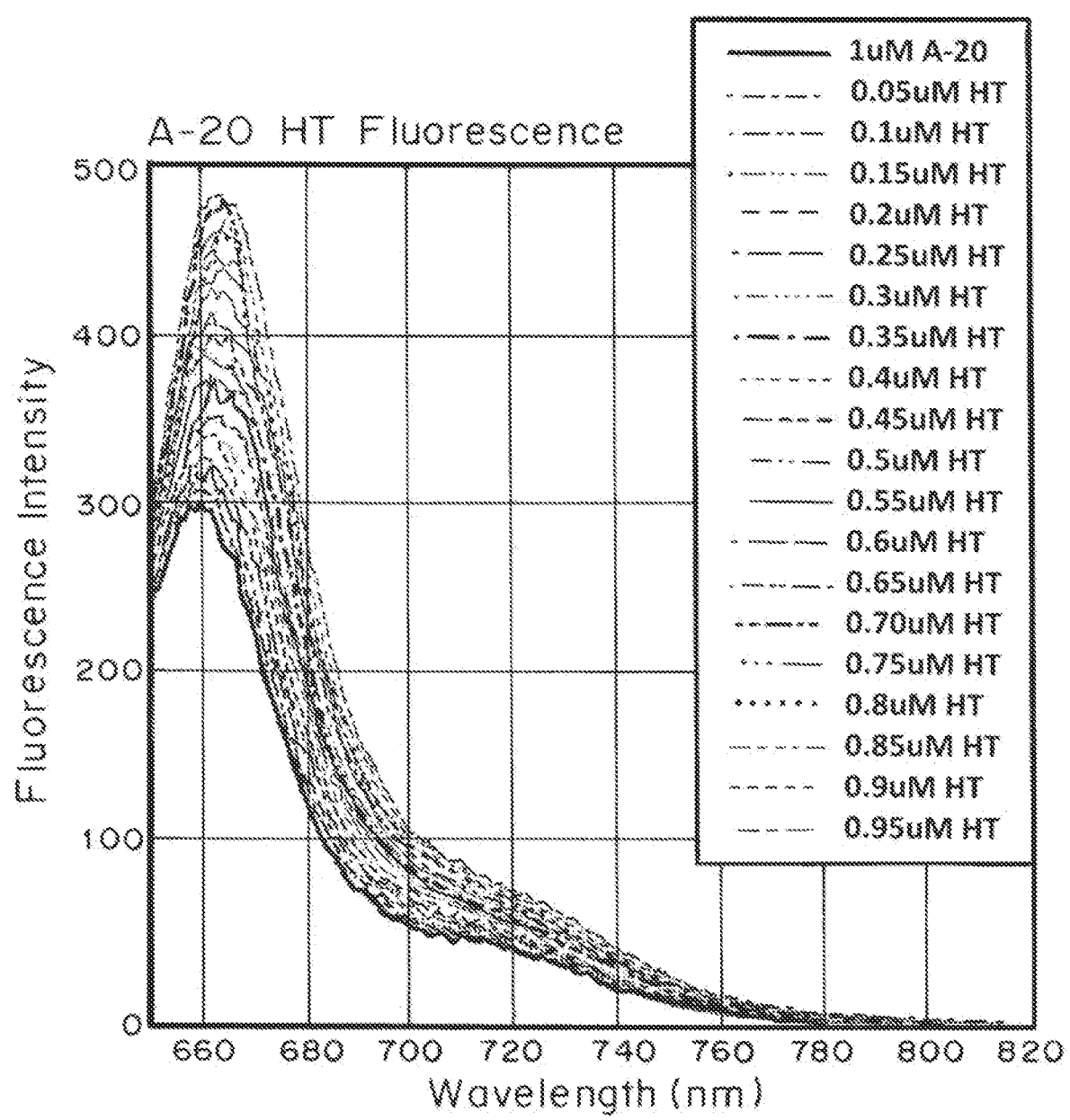
FIGS. 5A-D are fluorescence spectra (fluorescence intensity versus wavelength (nm)) of compounds 42 and 28 and their interaction with human telomere (42-FIG. 5A; 28-FIG. 5C) and c-Myc (42-FIG. 5B; 28-FIG. 5D) quadruplex DNA structures. In all cases the fluorescence of the free compound is the lowest curve and the highest curve is for the highest ratio of DNA to compound.
Figure 5B:
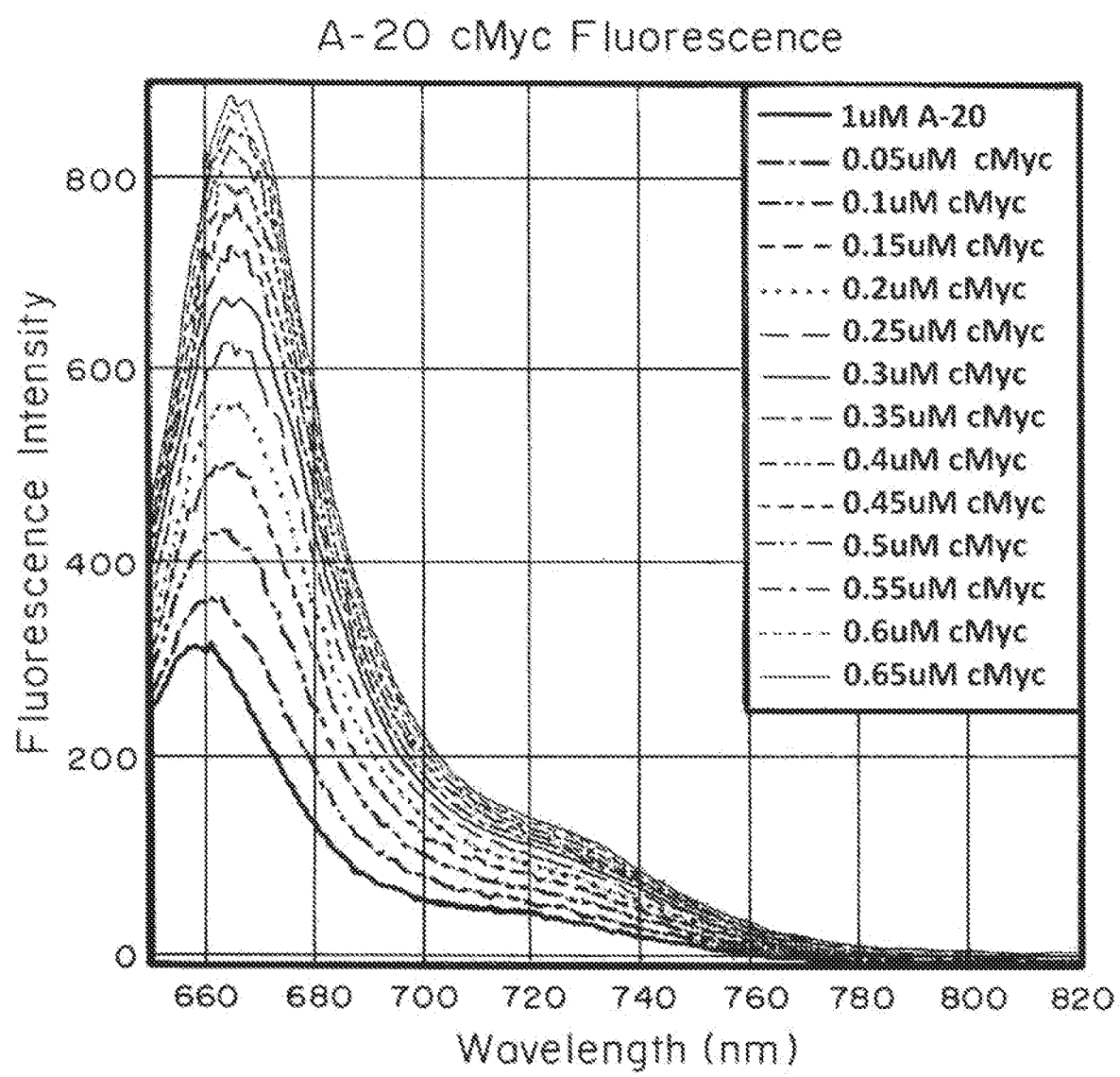
Figure 5C:
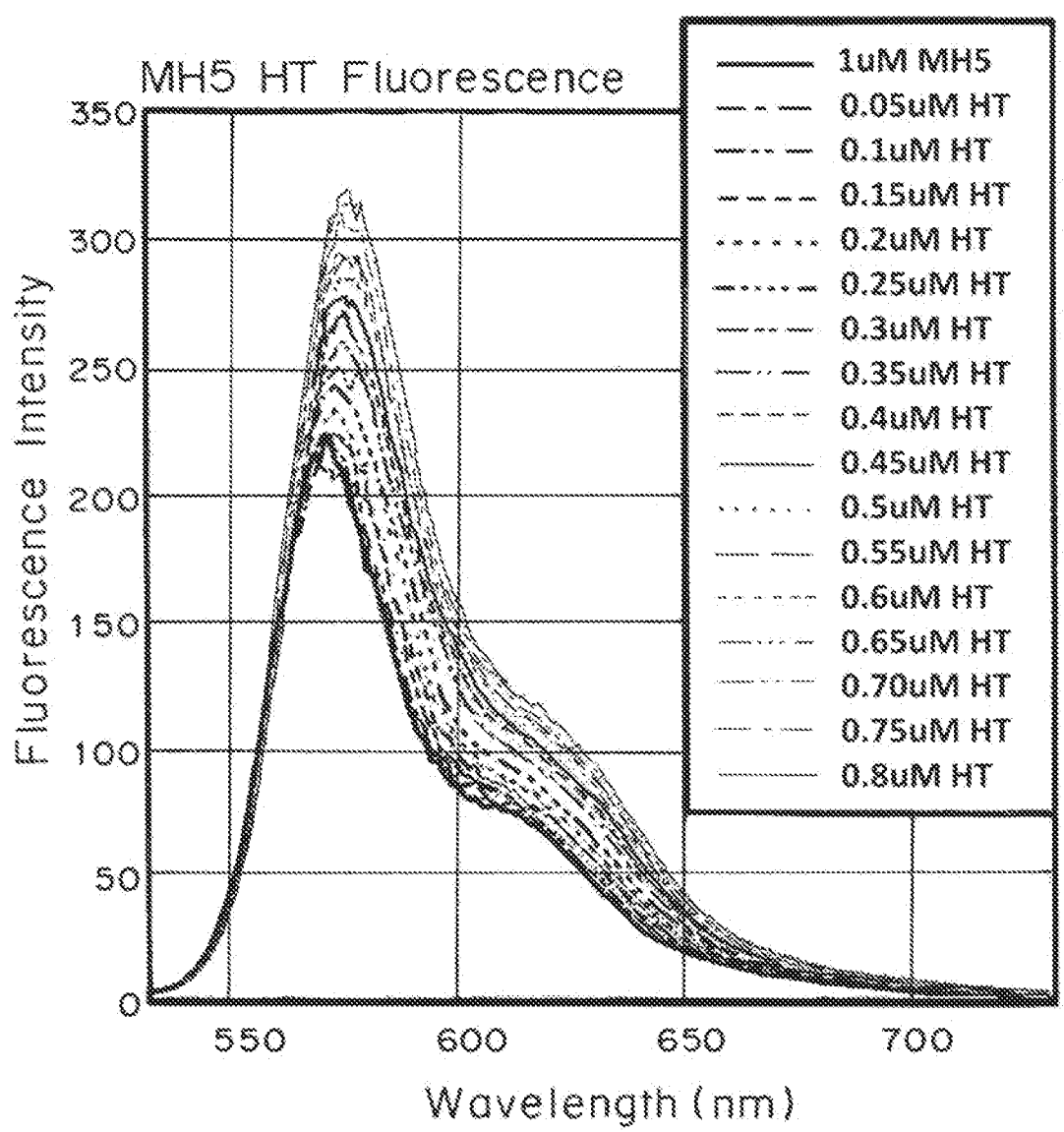
Figure 5D:
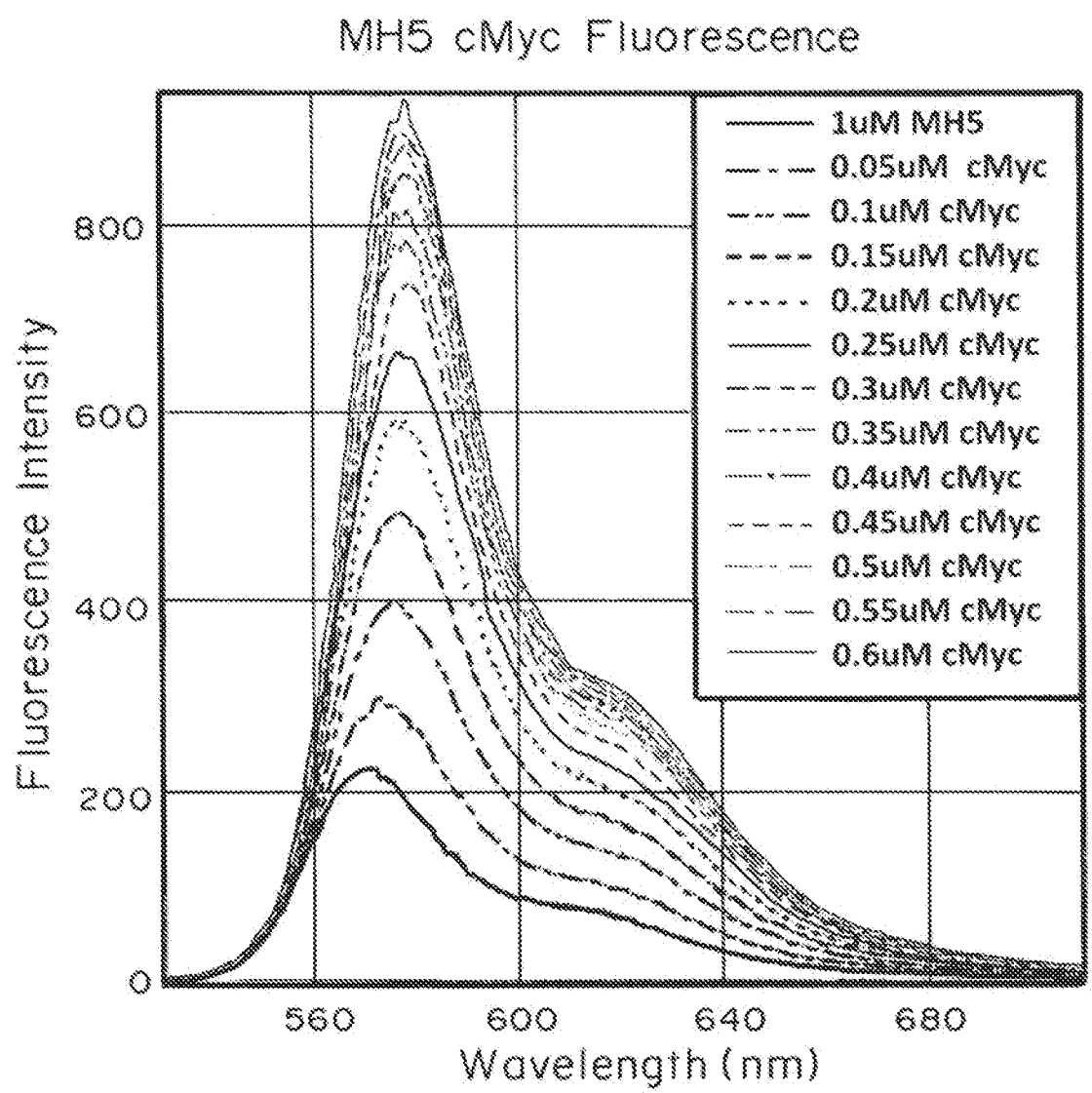

As can be seen in Table 2, ZK-14 and T5 bind quite strongly to the quadruplex with excellent selectivity over a reference DNA duplex model system (as used in previous studies). The thermal melting curves for T-4 and duplex and quadruplex DNA are shown in FIGS. 1a and 1b. The thermal melting curves for T-5 and duplex and quadruplex DNA are shown in FIGS. 2a and 2b. The thermal melting curves for Sp-2-36 and ZK-14 are shown in FIGS. 3 and 4.

Fluorescence

A UV-Vis absorbance scan is first conducted to acquire the excitation wavelength. A 5 μM solution of compound in 1 mL, of Tris/K+ buffer is scanned from 800 nm to 200 nm at a rate of 60 nm/min with a 5 nm slit width. All DNAs are diluted in Tris/K+ buffer. The human telomere and c-Myc DNA are annealed into a quadruplex motif by heating at 95° C. in the presence of potassium ions in a hot water bath for approximately five minutes, then allowing the solution to slowly come to room temperature. In a fluorescence cell, an emission scan of 1 μM of compound in 1 mL of Tris Buffer is taken (Varian Cary Eclipse, Walnut Creek, Calif.) with appropriate parameters based on the excitation wavelength, an excitation slit width of 5 nm, and an emission slit width of 5 nm. Then 0.05 μM of DNA is titrated into the solution and scanned under the same conditions after each addition. The solution is titrated to saturation, at which the change in fluorescence intensity is nearly zero.

Due to the highly stabilized parallel quadruplex structure of c-Myc, thermal melting could not be considered for this sequence. Thus, fluorescence can be used to measure binding affinity towards the two quadruplex structures. Overall, compounds bound with higher affinity toward c-Myc as compared to human telomere, as seen in Table 3. Fluorescence enhancement, or the fluorescence intensity of the bound ligand divided by that of the free ligand, was considered in evaluating binding.

TABLE 3

Fluorescence Enhancement

| | HT | c-Myc |
| --- | --- | --- |
| MH4 (26) | 1.68 | 7.74 |
| MH5 (28) | 1.6 | 4.65 |
| A-138 (17) | 2.7 | 5.4 |
| A-134 (19) | 2.0 | 4.1 |
| A-80 (30) | | 1.39 |
| A-20 (42) | 1.74 | 3.58 |
| A-21 (51) | | 1.02 |
| A-C8 (43) | 1.66 | 3.46 |

Figure 6A:
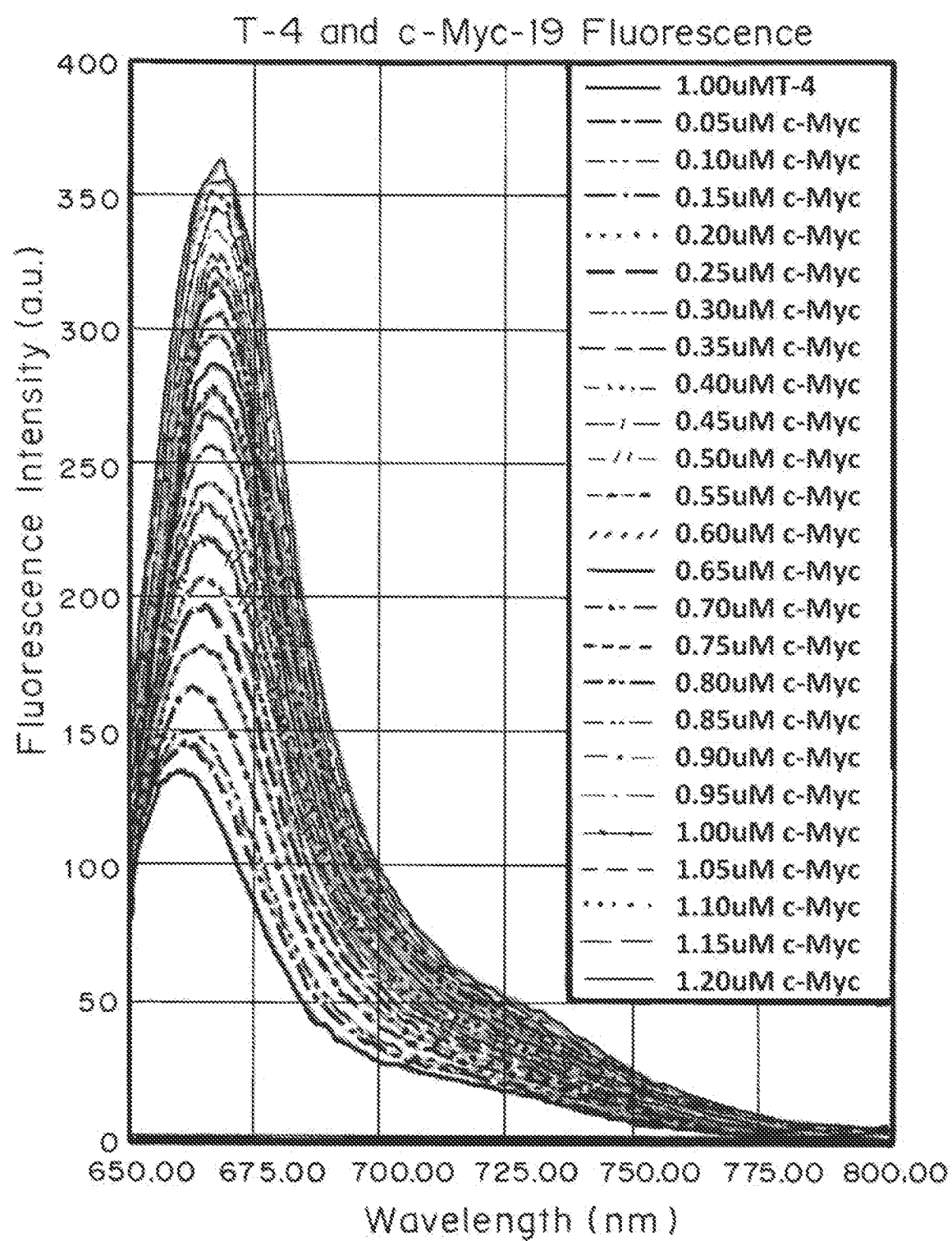
FIGS. 6A and 6B are fluorescence spectra (fluorescence intensity versus wavelength (nm)) of compound T-4 and their interaction with human telomere (6A) and c-Myc (6B) quadruplex DNA structures. In all cases the fluorescence of the free compound is the lowest curve and the highest curve is for the highest ratio of DNA to compound.
Figure 6B:
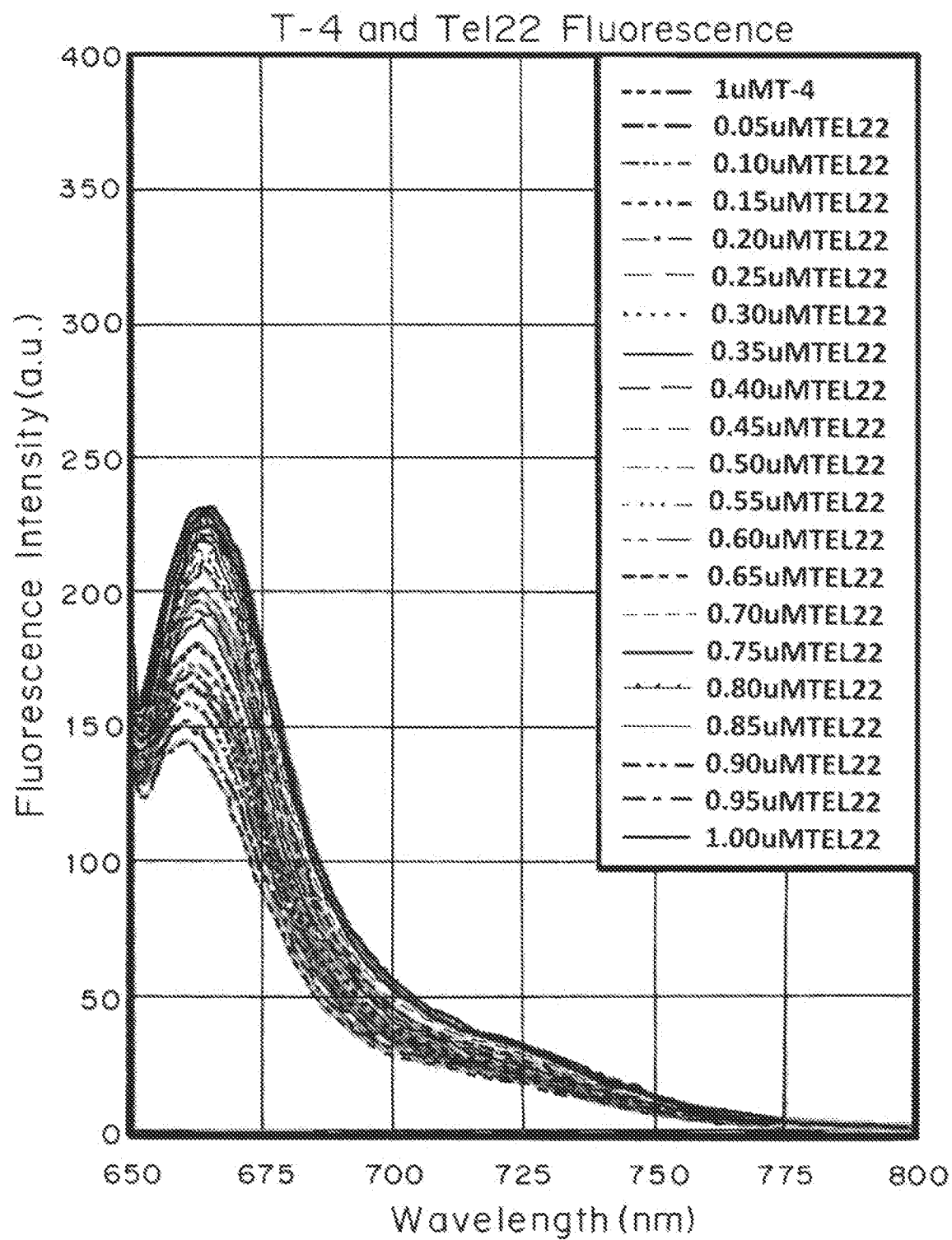
Figure 7A:
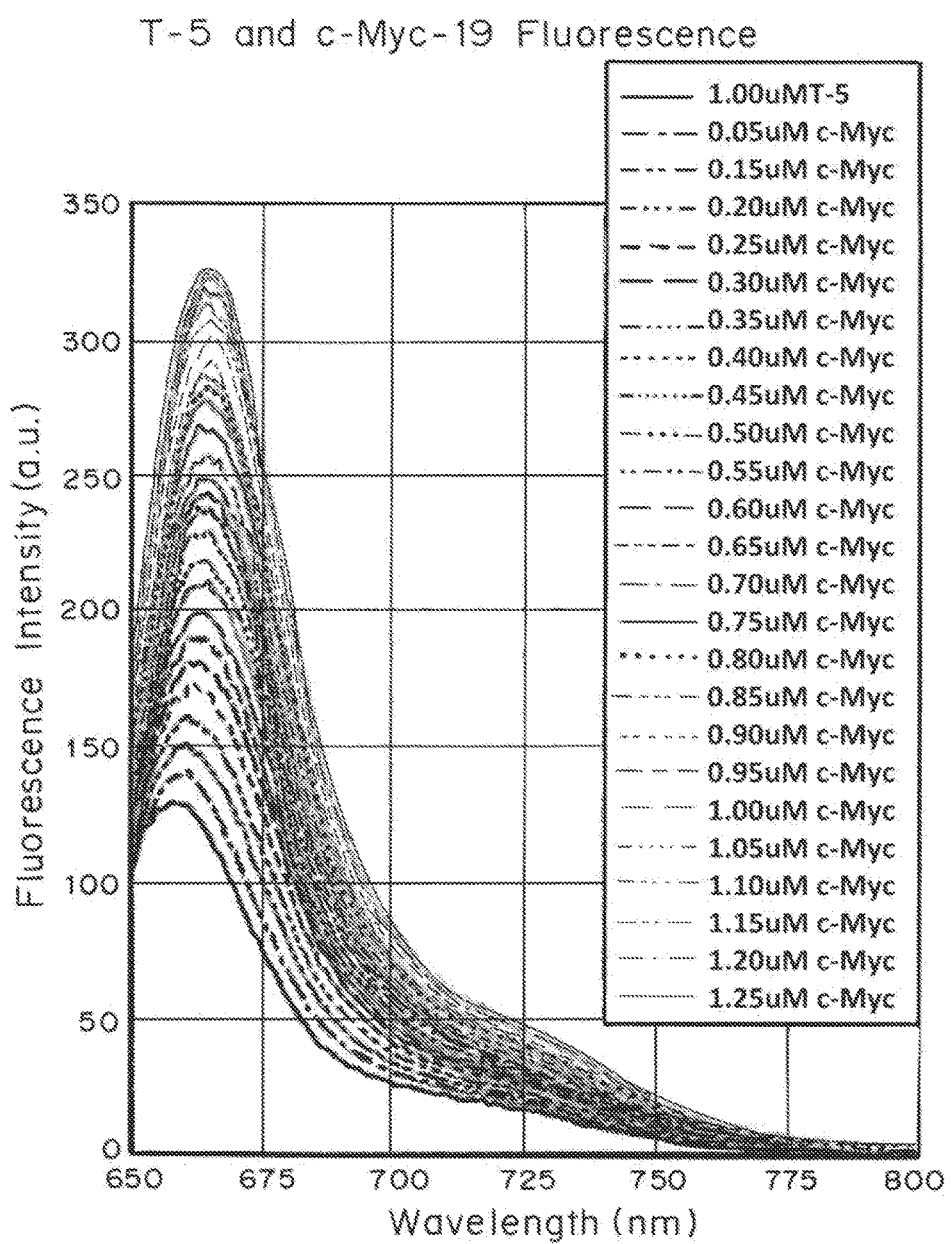
FIGS. 7A and 7B are fluorescence spectra (fluorescence intensity versus wavelength (nm)) of compound T-5 and their interaction with human telomere (7A) and c-Myc (7B) quadruplex DNA structures. In all cases the fluorescence of the free compound is the lowest curve and the highest curve is for the highest ratio of DNA to compound.
Figure 7B:
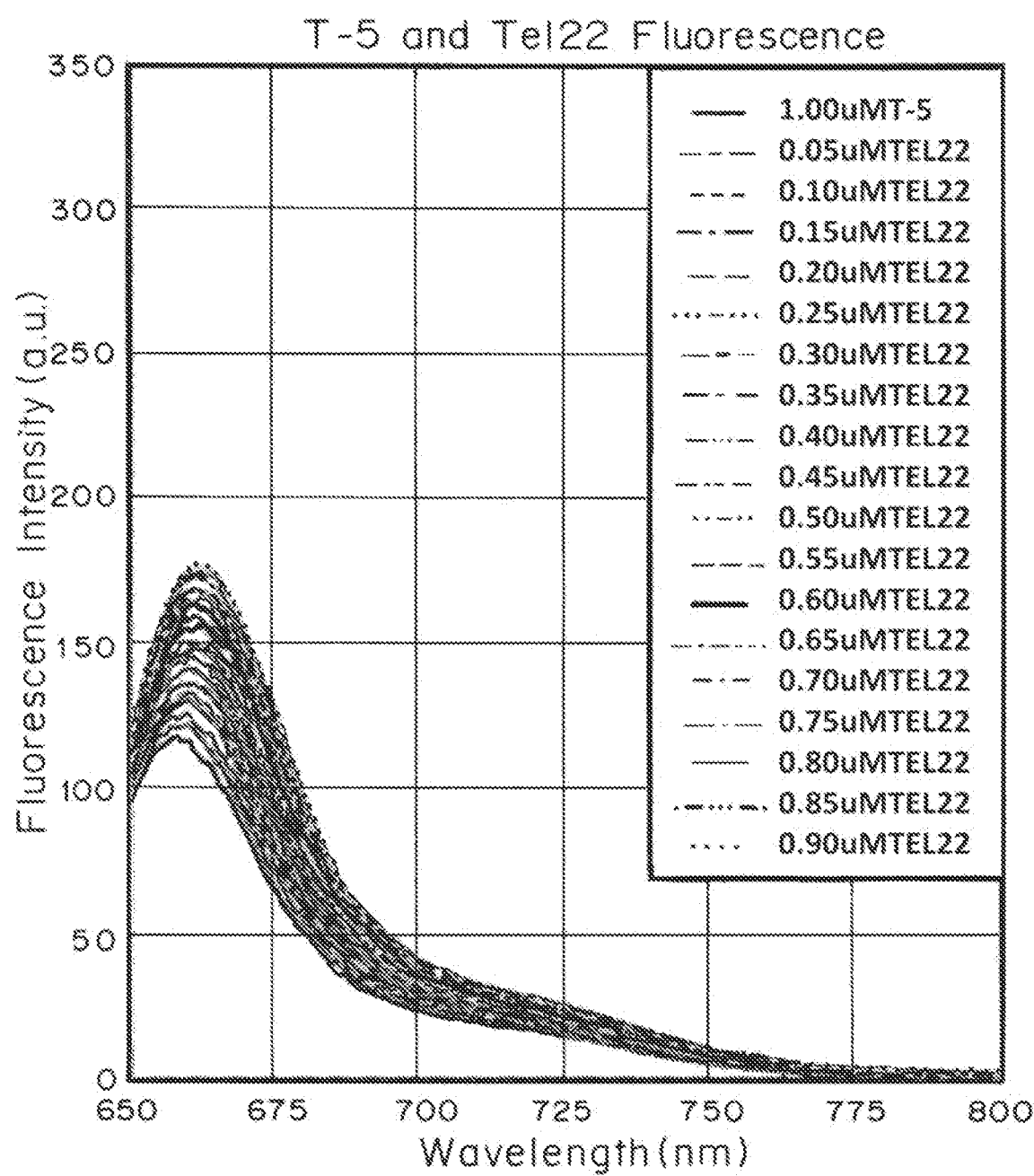

All compounds showed high fluorescence intensity when free in solution, and increased moderately with human telomere or almost to the maximum observed fluorescence that the instrument could detect with c-Myc, as shown in FIGS. 5A-D. This supports the conclusion that compounds that bind did so with a higher affinity towards c-Myc than human telomere. Fluorescence curves for T-4 are shown in FIGS. 6A and 6B. Fluorescence curves for T-5 are shown in FIGS. 7A and 7B. The strong binding cyanines have large fluorescence increases on binding to both quadruplexes but these results clearly show stronger binding of all compounds to the cMYC sequence.

Circular Dichroism

Figure 8A:
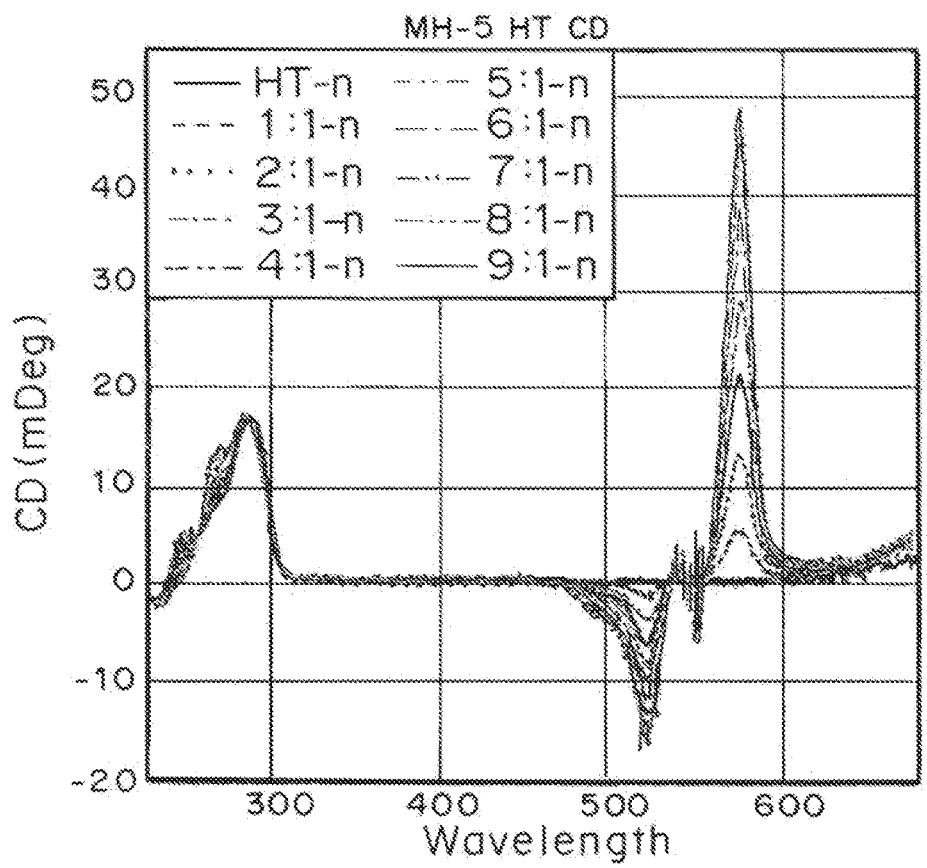
FIGS. 8A-8D are circular dichroism spectra (mDeg versus wavelength (nm)) of compounds 28 and 42 and their interaction with human telomere (28-FIG. 8A; 42-FIG. 8C) and c-Myc (28-FIG. 8B; 42-FIG. 8D).
Figure 8B:
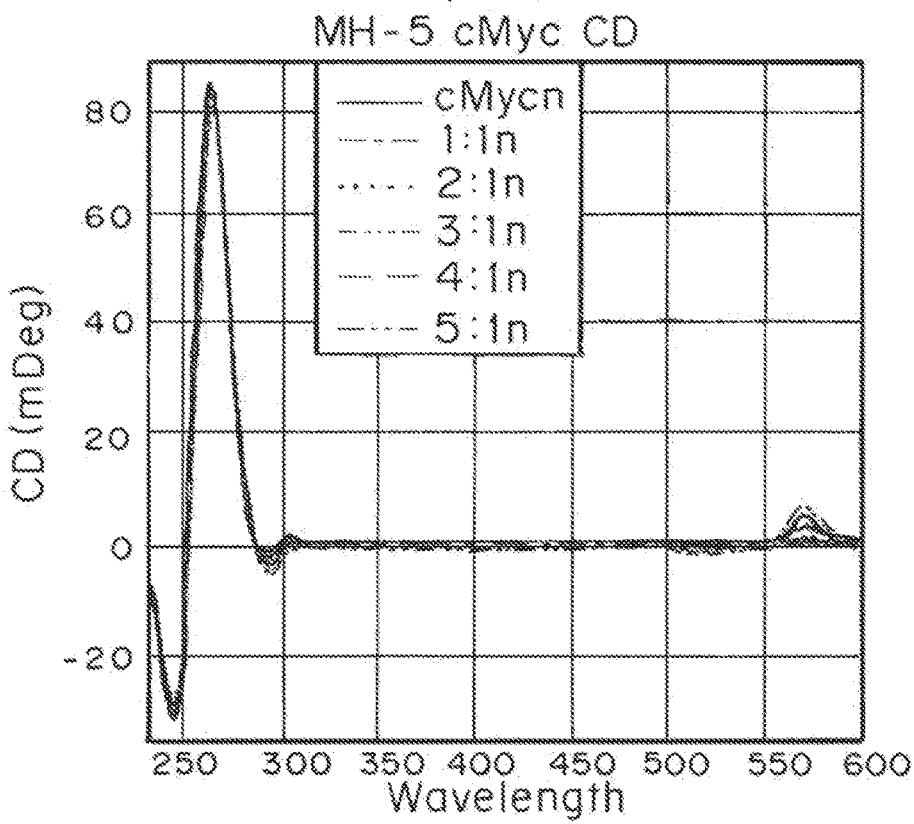
Figure 8C:
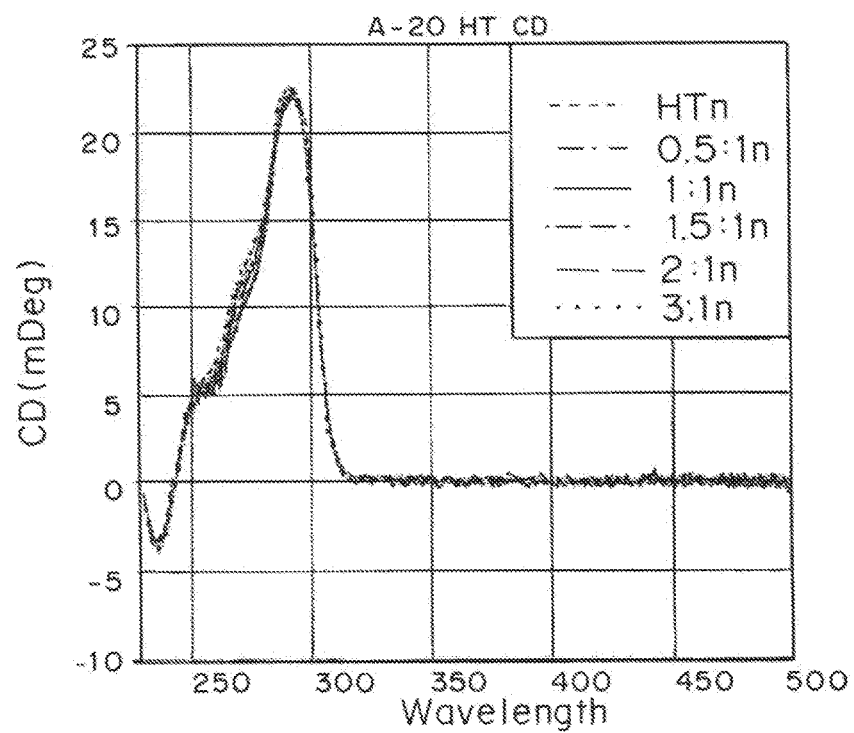
Figure 8D:
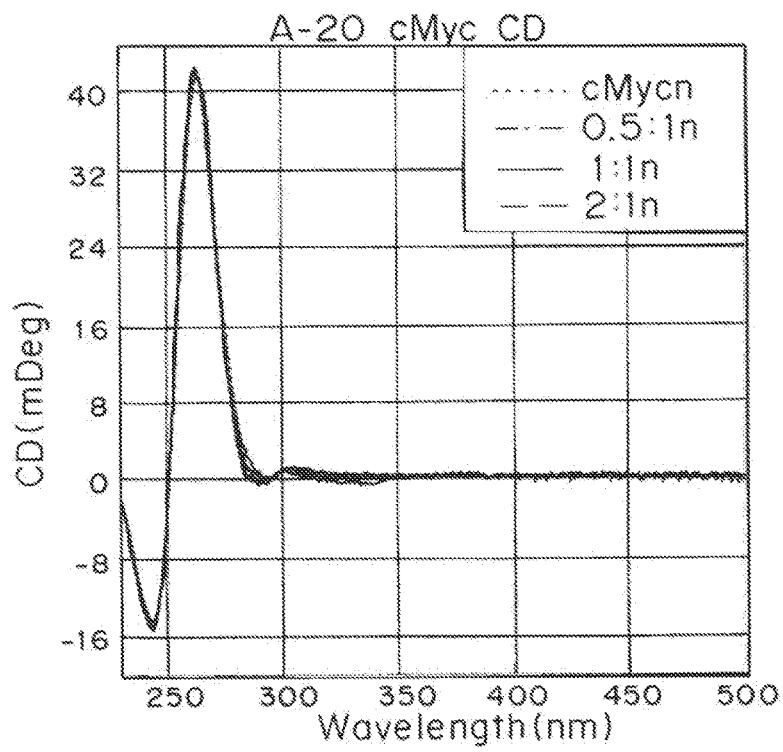
Figure 9A:
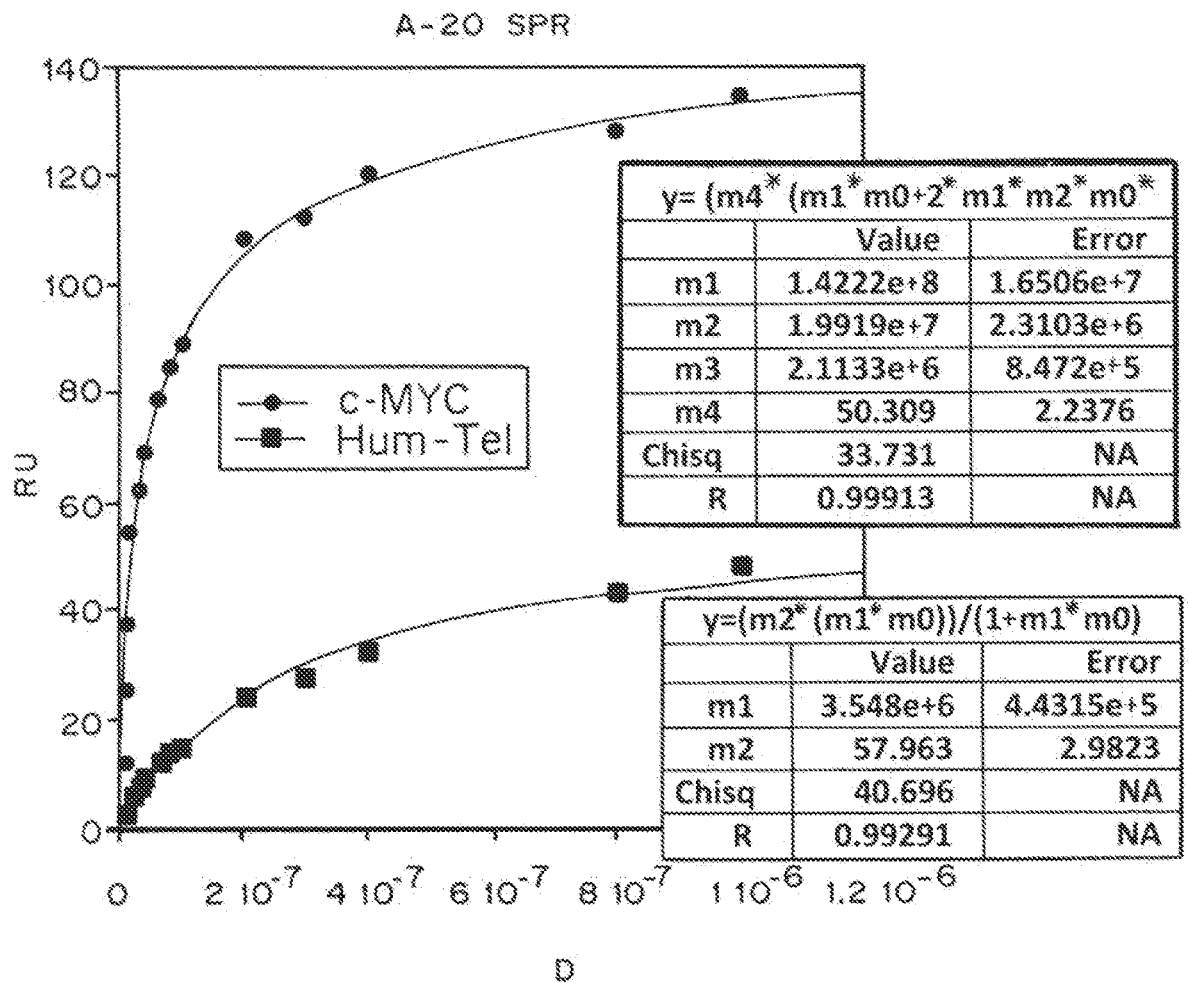
FIGS. 9A-9F are surface plasmon resonance ("SPR") spectra of compounds 42 (FIG. 9A), 28 (FIG. 9B), 26 (FIG. 9C), 17 (FIG. 9D), 19 (FIG. 9E), and 30 (FIG. 9F), and their interaction with c-Myc, human telomere, and duplex DNA.
Figure 9B:
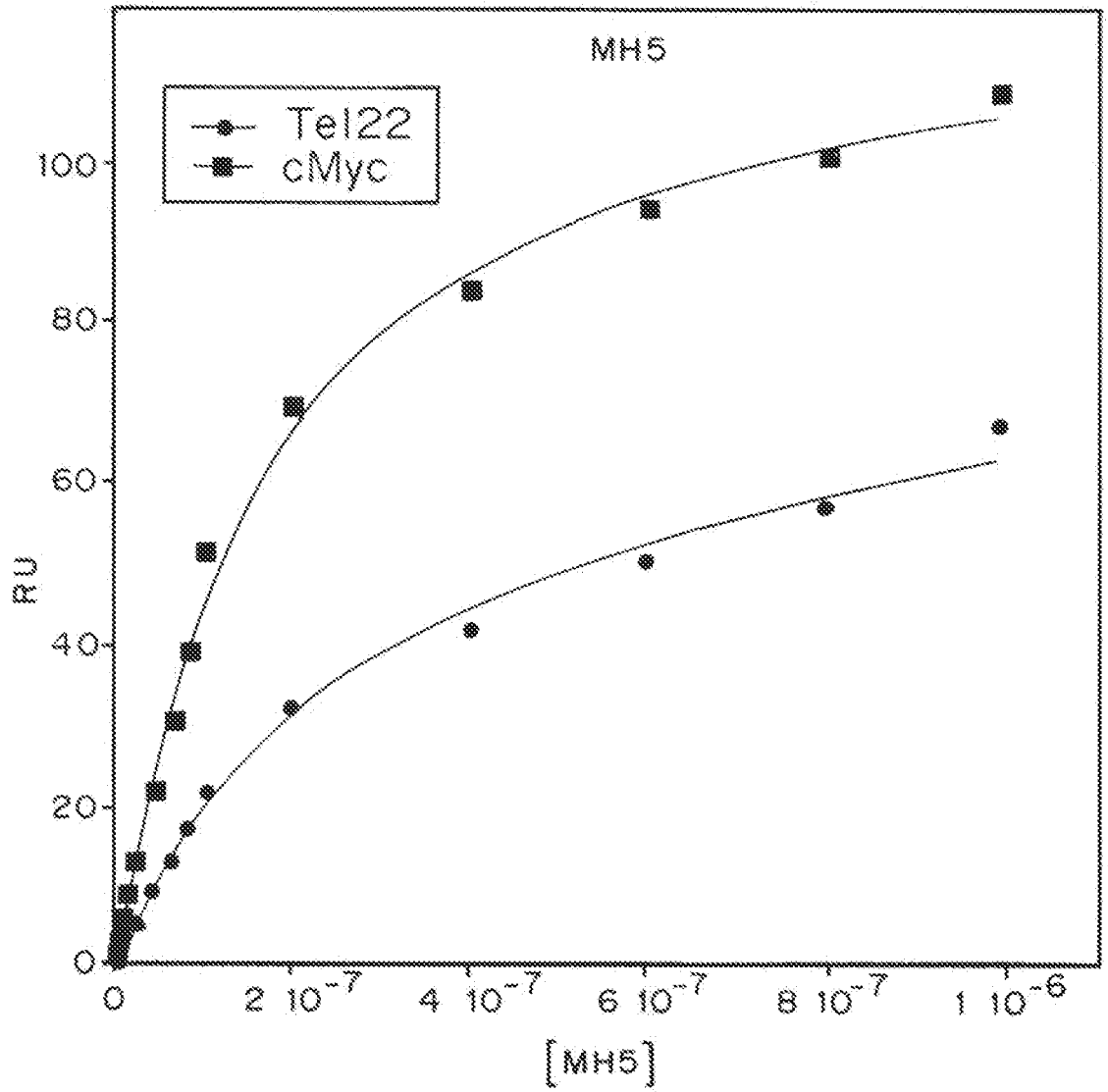
Figure 9C:
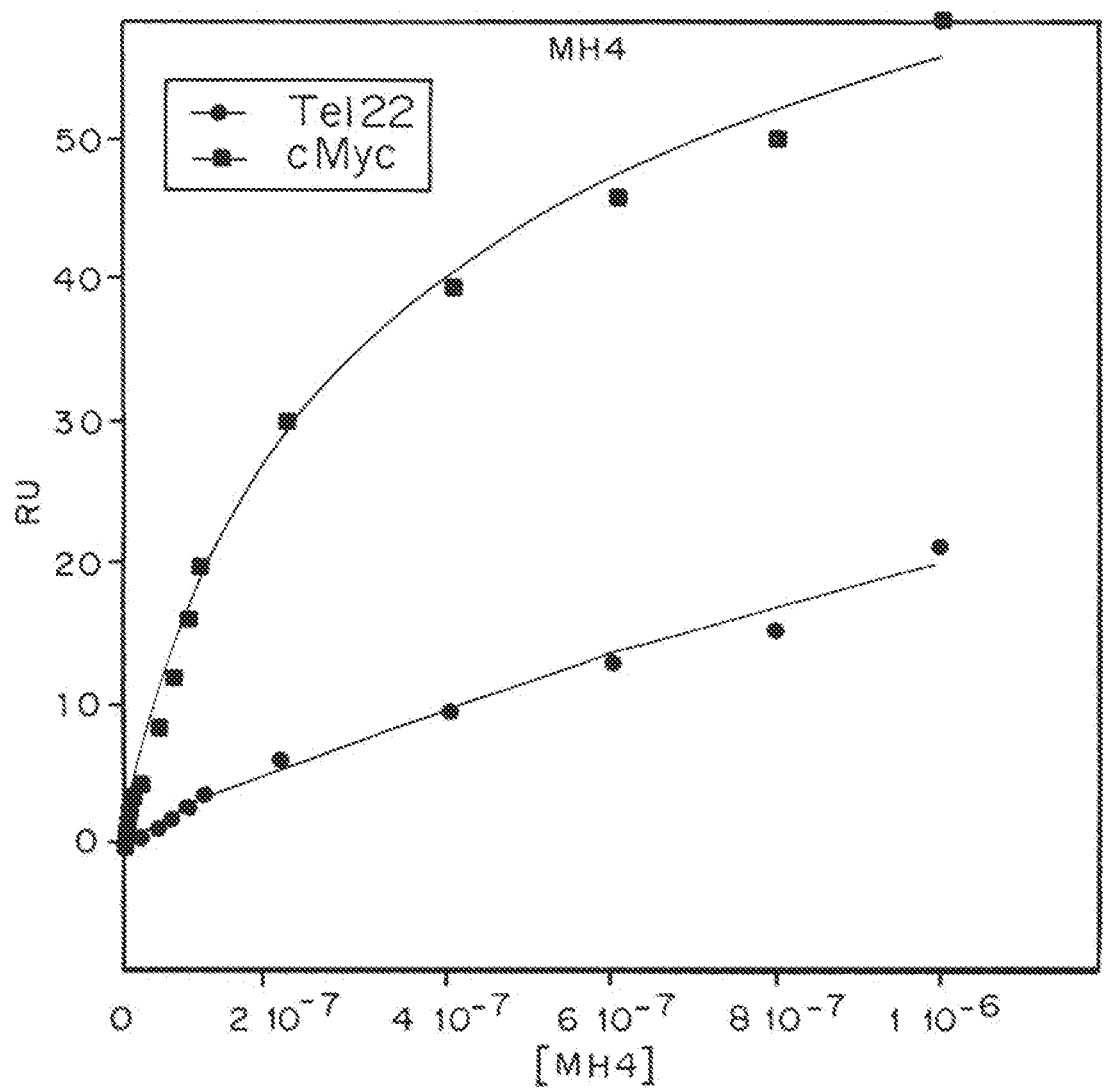
Figure 9D:
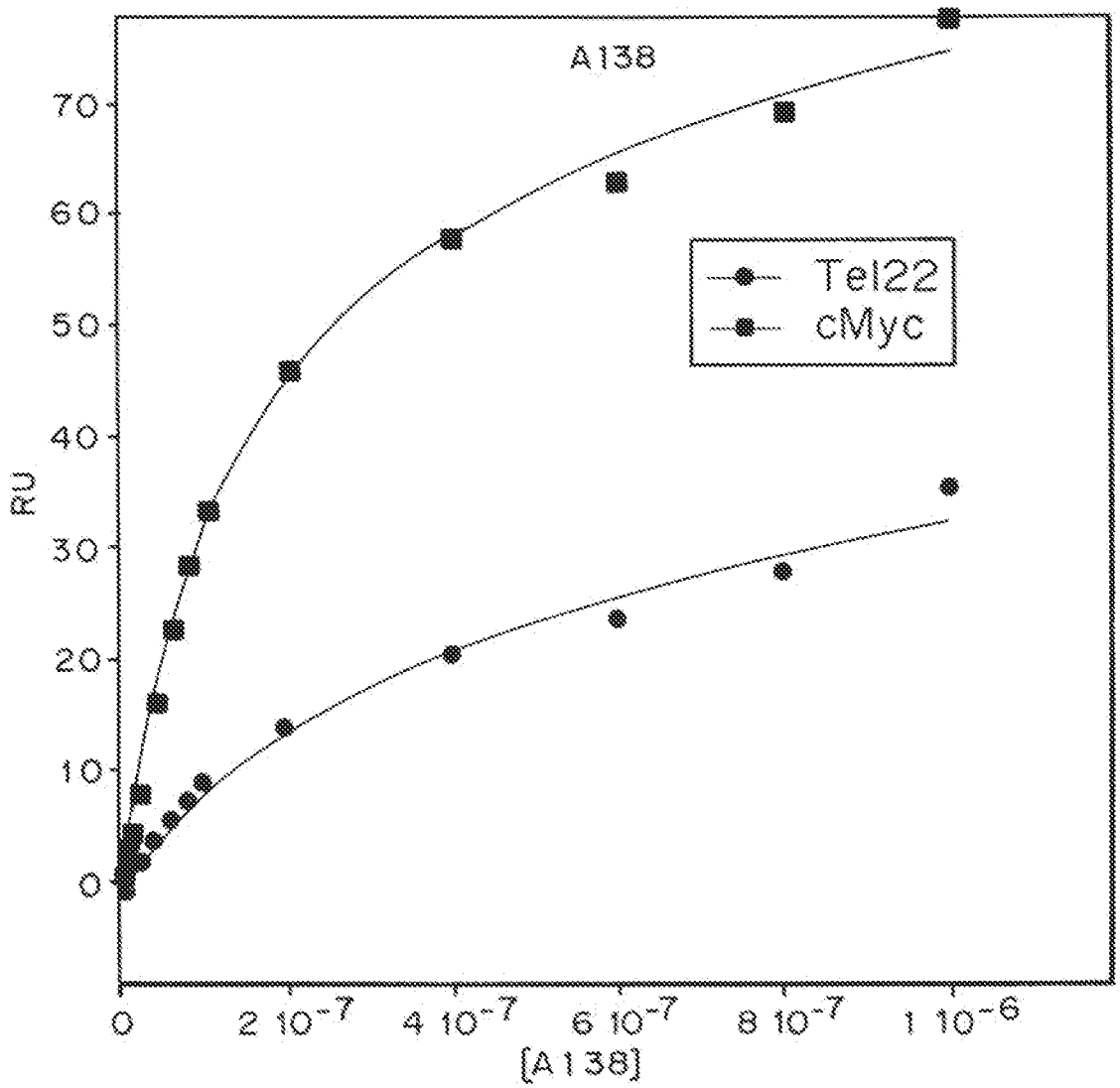
Figure 9E:
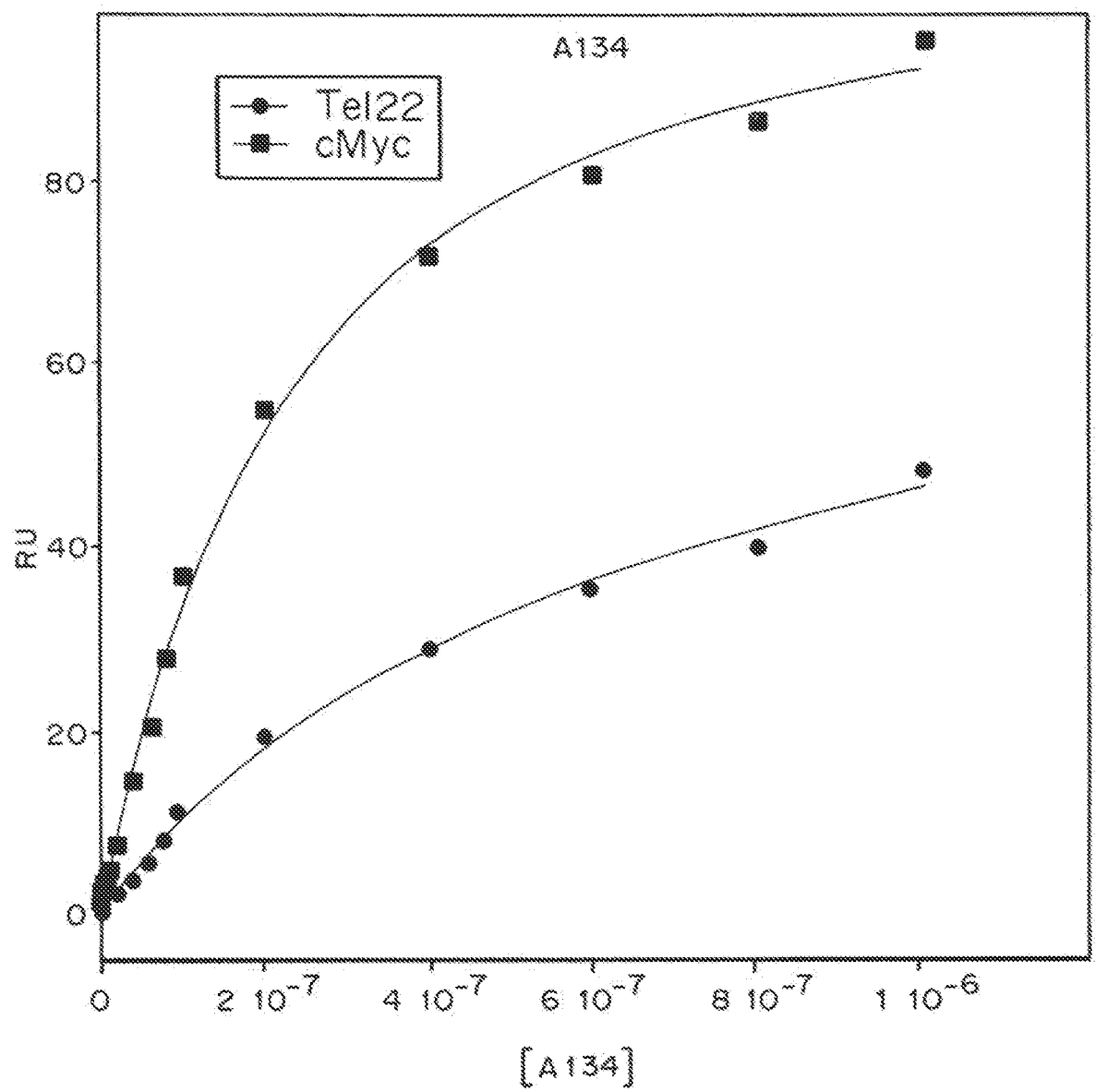
Figure 9F:
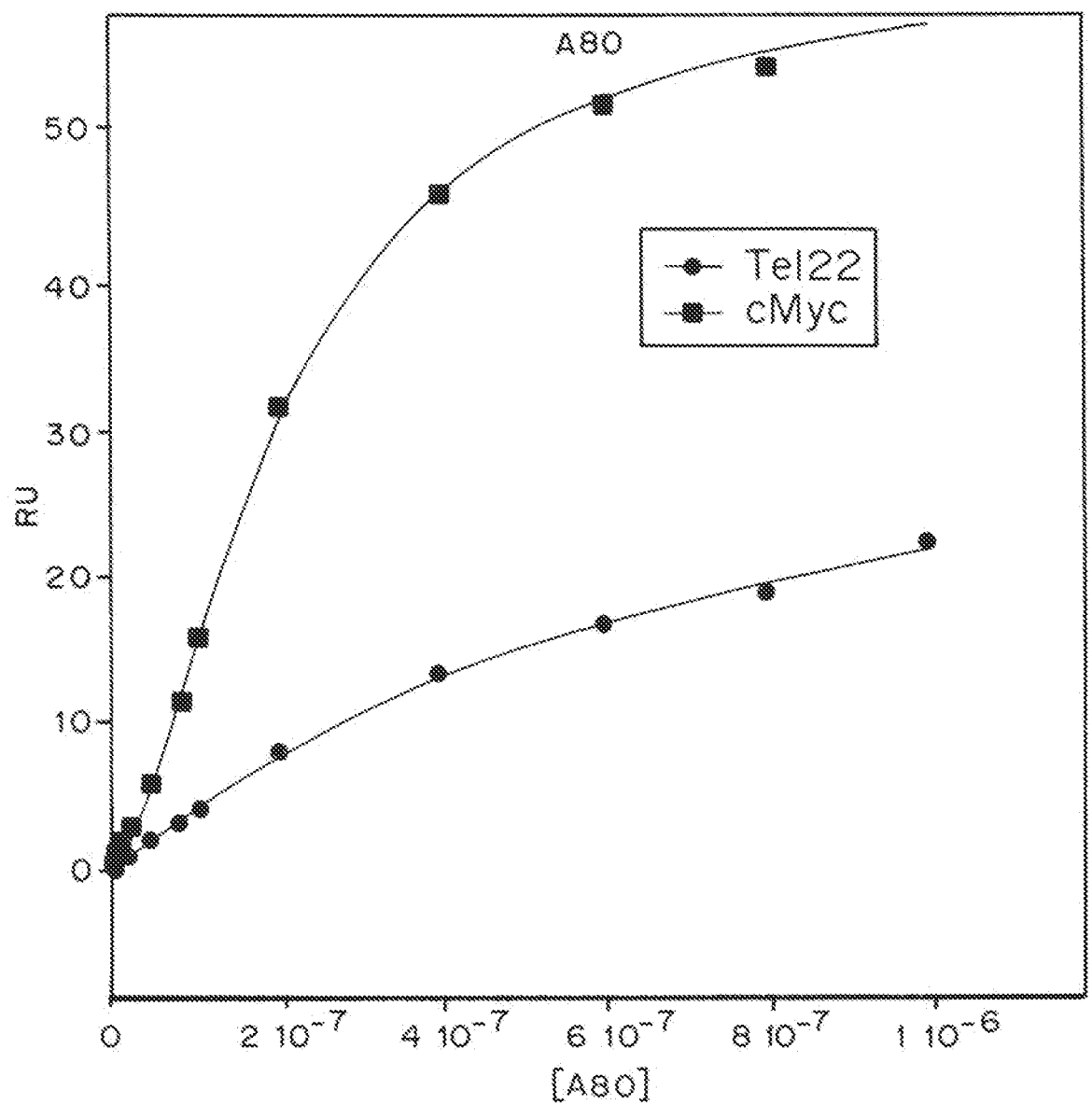

A sample of pre-annealed Human Telomere or c-Myc DNA was scanned with 3 μM DNA in 1 mL of Tris Buffer on a Jasco J-810 Spectropolarimeter. The solution is scanned from 230 nm to 700 nm at room temperature at a scan rate of 50 nm/min and a response time of 1 second. Appropriate volumes of compound were titrated into the solution, and scanned after each addition. The instrumental program averaged two scans for each titration and the buffer curve was subtracted using Kaleidagraph. The results are shown in FIGS. 8A and 8B (MH-5) and 8C and 8D (A-20).

Human telomere circular dichroism (CD) spectra show a positive shift around 290 nm and a positive shoulder at 255 nm indicating a hybrid quadruplex structure in potassium containing buffer. c-Myc spectra show a positive shift around 260 nm and a negative shift around 245 nm indicating a parallel quadruplex structure. Changes in the DNA region as well as induced CD in the compound region are analyzed with the CD titrations. With the exception of MH-5 (28), A-134, and A-138 (the dihalogenated compounds), none of the compounds showed any significant change in CD when titrated with either sequence of DNA. MH-5 (28) showed an enormous change in induced CD when titrated with human telomere, indicating groove binding (FIG. 8A). The DNA region changed somewhat as the DNA shifted toward the antiparallel form (positive shift at 290 nm with a shoulder at 280 nm). When titrated with c-Myc however, no change occurs in the DNA region, and only a slight induced CD appears in the compound region of the spectrum indicating possible end stacking. The compounds do not significantly change the DNA region of the CD spectra, which supports the theory of end stacking, or possibly loop binding as these binding methods do not alter the quadruplex shape significantly. The binding modes between human telomere (HT) and c-Myc appear to be different with respect to the dihalogenated compounds.

Induced CD spectra indicate binding mode in most cases. The cyanines appear to bind differently with each quadruplex structure. This is supported by the differing binding affinities seen in fluorescence titrations, and further supported by SPR data.

Surface Plasmon Resonance

Fifteen solutions of compound ranging from 0.0025 to 1 μM were injected over a chip containing the three immobilized DNAs on a Biacore 2000 (GE Healthcare Life Sciences, Pittsburgh, Pa.). The solutions were made with filtered and degassed HEPES buffer with 0.01% P20 (GE Healthcare Bio-Sciences, Upsalla, Sweden). A 200 s injection time, a 400 s dissociation time, a flow rate of 25 µL/min, and a temperature of 25° C. were used. The regeneration buffer used was Glycine at pH 2.

The cyanines tested with Surface Plasmon Resonance (SPR) proved to be sticky: the tricationic compounds tend to stick to the negatively charged SPR chip. Despite the difficulty in testing them, the sensograms collected all confirmed the strongest binding to c-Myc, strong but less so to human telomere, and nearly no binding to duplex. The fit data is shown in FIGS. 9A-9D.

Of the cyanines tested, A-20 proved to be the least sticky. The data was fit with three binding sites for c-Myc (K1=1.4*108, K2=2.0*107) and one for human telomere (K=3.5*106). Human telomere (K1=1.5*106, K2=1.3*107) sensogram was also fit with two binding sites.

As shown above in the thermal analysis data, in many cases, $\Delta$ Tm values for hTelo continue to increase steadily until a ratio of compound to DNA of 6:1 is reached. This may be indicative of cyanines stacking in solution. SPR confirms that despite aggregation problems, the cyanines bind better to hTelo than to duplex DNA, but still with binding constants less than $10^7$ $M^{-1}$. However, the compounds are found to bind strongly to c-myc when measured using SPR (K>$10^6$ $M^{-1}$).

Thermal melting data can be difficult to collect accurately for c-myc due to its high melting temperature. Compounds often increase the melting temperature beyond measurable values with this DNA. Salt concentrations may be lowered to decrease the c-myc melting temperature, but cellular conditions as well as quadruplex formation require salt. Thus, lowering salt concentrations is not always a desirable comparison. Nonetheless, a strong correlation is observed between thermal melting screening data and SPR proven binding affinities to c-myc.

Pentamethine trisubstituted compounds prove to be sticky, but maintained previously established trends: the two methyl groups prevent duplex binding, and the sulfonate groups on A-21 minimize quadruplex binding. Thermal melting data reveals a possible indication of where on the compound DNA interactions may occur. If the ring halogens remain constant and the methine halogen is varied (in the case of A-150 to A-149, A-148 to A-146, and A-161 to A-160), a methine-linked bromine consistently raises the stabilization of DNA compared to compounds with methine-linked chlorine. When the ring halogens are varied and the methine halogen remains the same (in the case of A-150 to A-148 and A-161, and A-149 to A-146 and A-160), no significant trend emerges. Therefore, based on the saturation at 4:1 $\Delta$Tm values, the methine-linked halogen appears to significantly increase stabilization of quadruplex DNA.

Electrospray Ionization Mass Spectrometry

A sample of concentrated c-myc was desalted in 0.1 M ammonium acetate buffer (Fisher Scientific, Fair Lawn, N.J.) pH 6.8. A dialysis bag was prepared with DNA, and the solution was allowed to sit, and chilled for at least seven days: the buffer solution was changed every other day. Solutions were made in ammonium acetate buffer with 10% methanol (Fisher Scientific, Fair Lawn, N.J.) with varying ratios of compound to DNA: 0:1, 1:1, 2:1, 4:1, and 6:1. The solutions were tested on the Waters Micromass Q-TOF micro in negative mode with a voltage of 2500.

Mass spectrometry was done with the strongest binding monohalogenated cyanine dye—A-C8, as strong binding compounds are required to remain bound in the charged gas state needed for electrospray ionization. The 1:1 peak is favored, as seen with trimethine dyes, but a 2:1 peak forms at lower ratios of compound to DNA. The 2:1 peak of c-myc with A-C8 requires less compound to form than the 2:1 peak with MH-5. This peak can only be seen at the 4:1 ratio with MH-5, but can be seen at the 2:1 ratio with A-C8.

Mass spectrometry for A-148 and A-150 show similar results to those seen with pentamethine monohalogenated compounds: the 1:1 peak is the favored binding ratio, and the 2:1 binding ratio is seen at a 2:1 solution ratio of compound to DNA. The unbound quadruplex peaks seem to be larger at higher compound to DNA ratios than with monohalogenated dyes. This may be due to the compounds' propensity to stack in solution.

Isothermal Calorimetry

Solutions of compound (0.2 mM) were injected 30 times into solutions of DNA (0.02 mM) on a VPC-ITC. All solutions were degasses at 25° C. for 15 minutes. TRIS/$K^+$ buffer was used in the reference cell. The injections were monitored at 25° C. with a reference power of 1 µcal/sec, an initial delay of 300 sec, and a stirring speed of 290. The first injection was 2 µL for 4 sec, with a spacing of 300 sec, and a filter period of 1 sec. The remaining 29 injections were 10 µL volume for a duration of 20 sec, with a spacing of 300 sec, and a filter period of 1 sec. The data was analyzed by VPViewer 2000 software.

Isothermal calorimetry (ITC) experiments were performed to test the SPR and fluorescence preference in binding c-myc over hTelo. ITC is known to under-estimate binding constants for strong binding compounds in comparison with other techniques such as SPR as shown in Tables 4 and 5 for MH-5 and A-C8, respectively.

TABLE 4

Thermodynamic data for MH-5 binding

| Oligomer | Stoichiometry | K ($M^{-1}$) | $\Delta$H (cal/mol) | $\Delta$S cal/ (mol C. °) | $\Delta$G (cal/mol) |
|---|---|---|---|---|---|
| c-myc | 1.11 ± 0.01 | 1.19E+06 | −3190 ± 40 | 17.1 | −8278.85 |
| hTelo | | Weak binding- unable to fit | | | |
| $A_2T_2$ | | No binding | | | |

TABLE 5

Thermodynamic data for A-C8 binding

| Oligomer | Stoichiometry | K ($M^{-1}$) | $\Delta$H (cal/mol) | $\Delta$S (cal/ mol C. °) | $\Delta$G (cal/mol) |
|---|---|---|---|---|---|
| c-myc | 1.22 ± 0.01 | 8.02E+05 | −2100 ± 20 | 20 | −8045.32 |
| hTelo | 1.02 ± 0.02 | 5.57E+04 | −6100 ± 200 | 1.15 | −6466.94 |
| $A_2T_2$ | | No binding | | | |

These tests consistently show a single binding site, which is inconsistent with the equation that best fits the SPR data. ITC measures heat from binding, so a second, or perhaps nonspecific binding site may show no heat change. Mass spectrometry proves this assumption to be correct. The experiments show that one binding site is preferred, but a second binding site can occur in high compound to DNA ratio conditions.

Example 10

Cytotoxicity of Cyanines

Figure 10A:
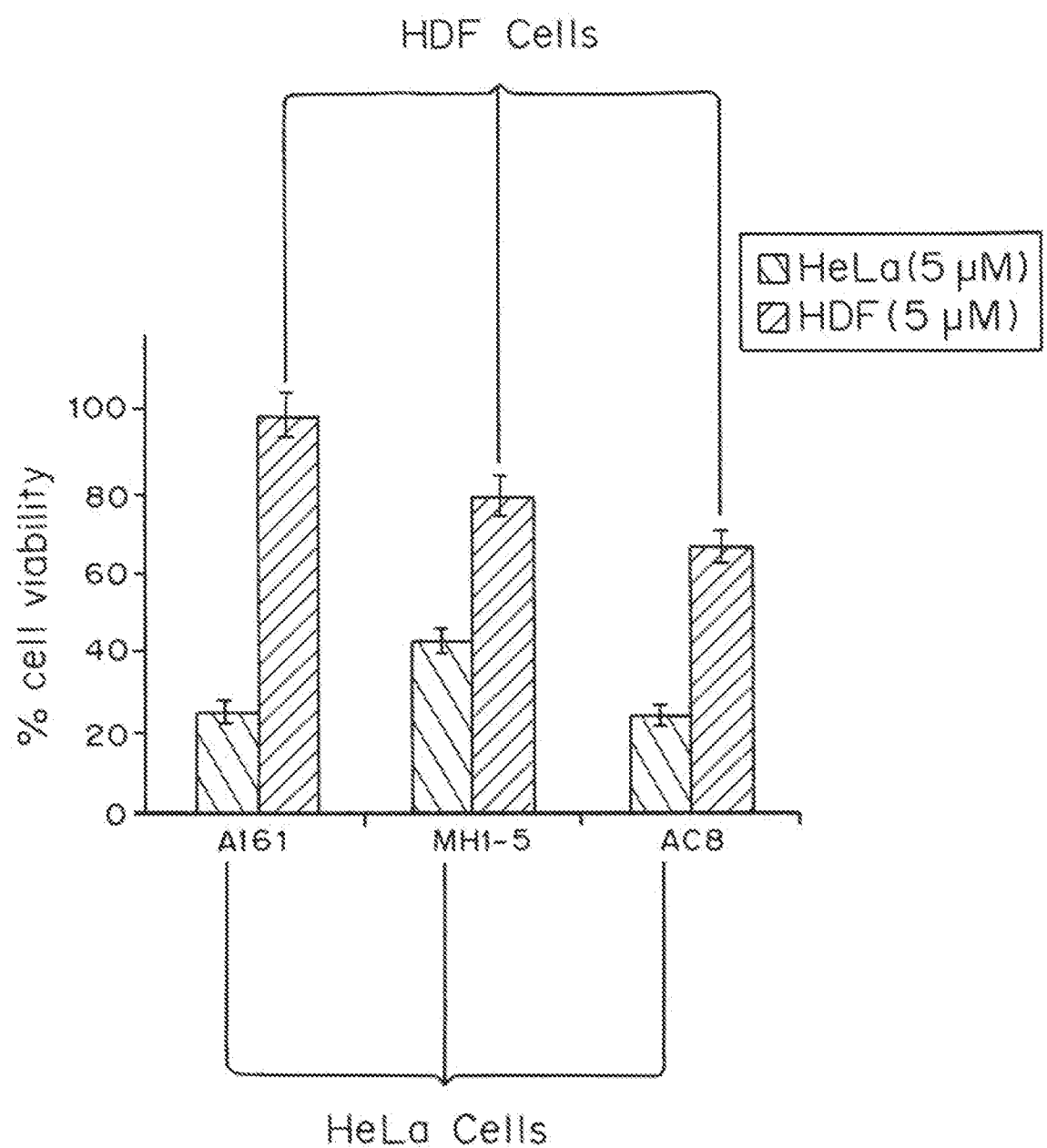
FIGS. 10A and 10B are bar graphs showing percent cell viability as a function of compound at a concentration of 5 micromolar (FIG. 10A) and 20 micromolar (FIG. 10B).
Figure 10B:
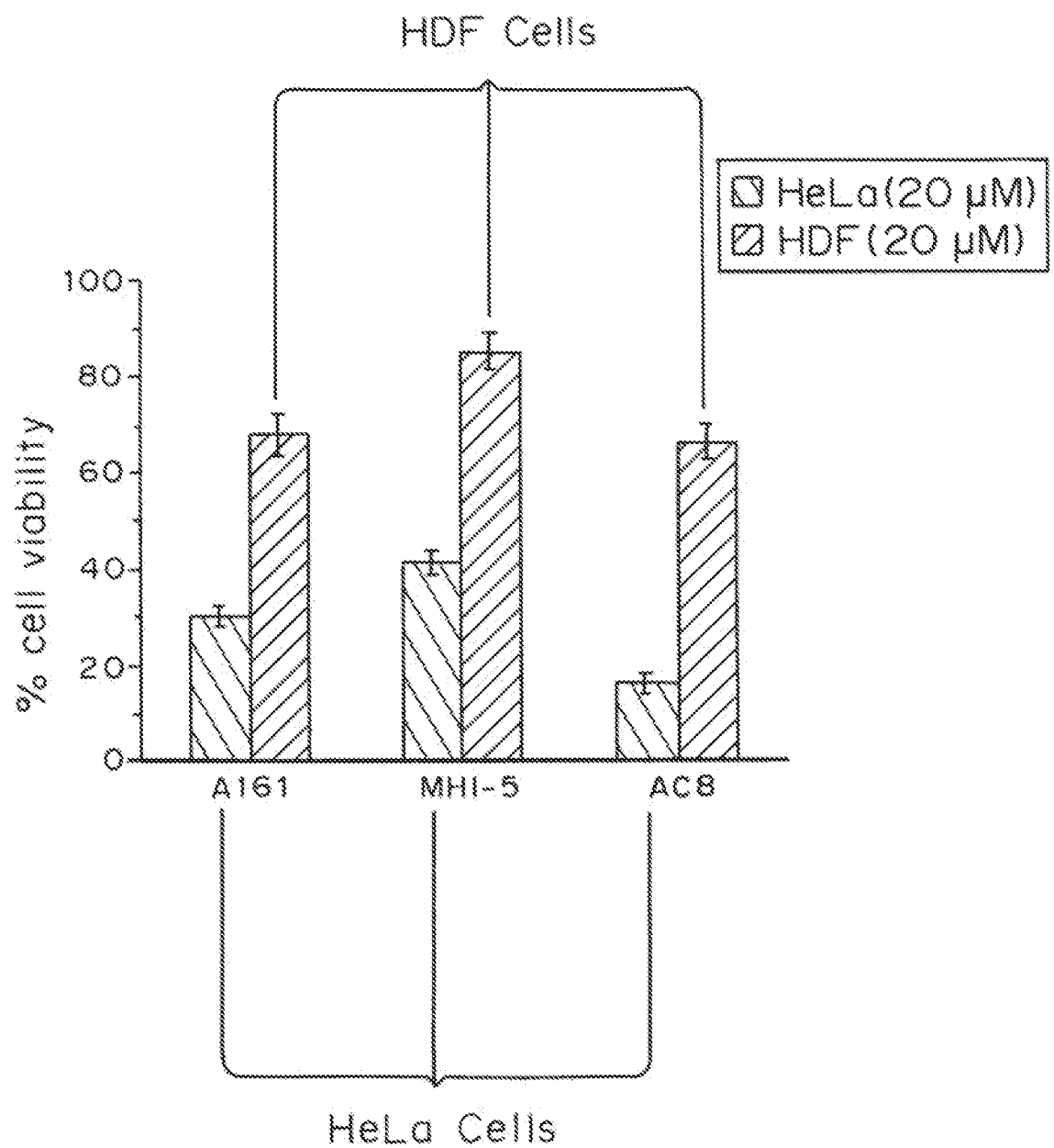

To evaluate the cytotoxic properties of the cyanines described herein, trypan blue exclusion assay for cell viability was performed on 10 compounds at two different concentrations (5 μM and 20 μM). To test the cancer selectivity of the dyes, the results were compared in a cancer cell line, HeLa and a non-cancerous cell line, HDF. The loss of membrane integrity in dead and dying cells allows preferential uptake of labels like trypan blue. At the end of the incubation times with the dyes, HeLa or HDF cells were pelleted and washed with PBS. Well-suspended cells were mixed with equal volume of 0.4% trypan blue in 1×PBS, pH 7.4, followed by incubation at room temperature for 5 min. Cells were examined under the microscope and blue-stained cells were considered non-viable. The results are shown in FIGS. 10A and 10B.

The trypan blue exclusion data demonstrated that three dyes were cytotoxic to cancer cells but spared normal cells as shown below. A-161 at concentrations of 5 μM and 20 μM killed >70% of Hela cells after 24 h whereas HDF cells were unaffected at the lower dose levels. This demonstrated selectivity of A161 for cancer cells while normal cells showed 100% cell viability at the lower dose. On similar lines, MHI-5 was highly cytotoxic to cancer cells, with HeLa cells showing enhanced sensitivity compared to HDF at both concentrations studied. AC8 treatment however compromised cell viability of HDFs to some extent. Lower concentrations (5-10 μM) resulting in ~35% cell death was observed at both concentrations, indicating cytotoxicity even at lower concentrations.

The structures of A161, MHI-5 and AC8 are shown below.

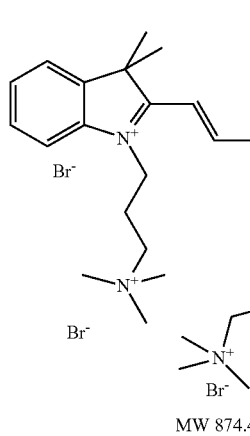

AC8

MW 874.49

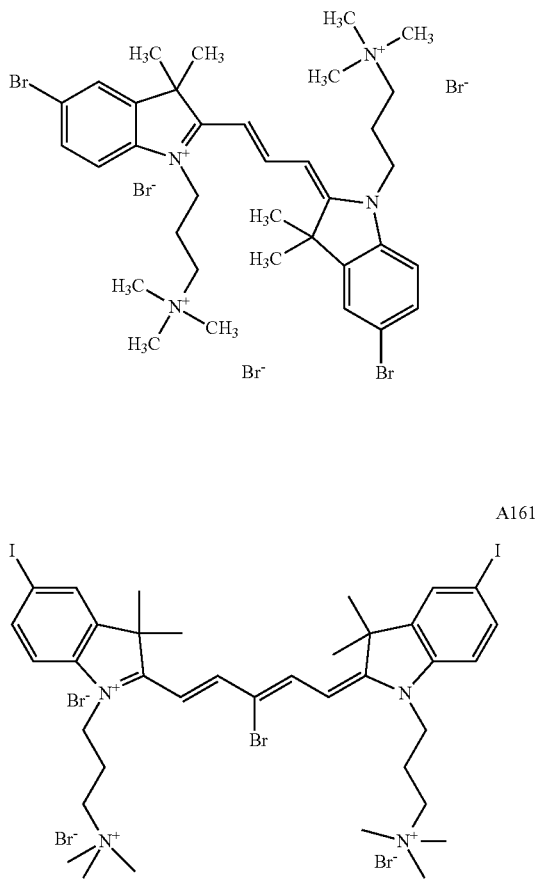

MHI-5

A161

MW 1126.26

The synthesis of these compounds is presented in Schemes 1 and 2 above.

---

We claim:

1. A pharmaceutical composition comprising (i) one or more cyanines, wherein the one or more cyanines are selective for G-quadruplex DNA over duplex DNA and (ii) one or more pharmaceutically acceptable excipients, wherein each of the one or more cyanines has the formula:

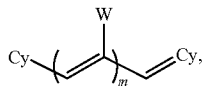

wherein:
m=0, 1, 2, or 3;
each Cy is independently a substituted or unsubstituted heteroaromatic moiety, wherein at least one of the heteroatoms in at least one Cy is nitrogen substituted with a group containing one or more cationic moieties, and wherein each Cy is the same or different;
each occurrence of W is independently hydrogen; halogen; cyano; trifluoromethyl; benzoic acid; substituted or unsubstituted alkyl, alkenyl, alkynyl, cycloalkyl, or cycloalkenyl; or a group containing one or more (a) cationic atoms or moieties or (b) atoms or moieties that are cationic under physiological conditions; and
wherein each Cy is independently:

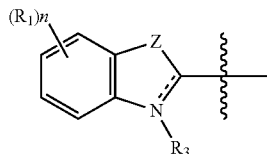

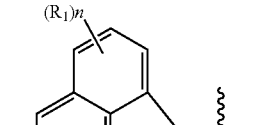

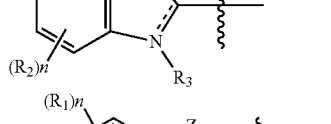 or

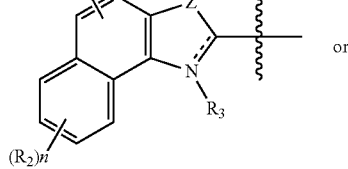

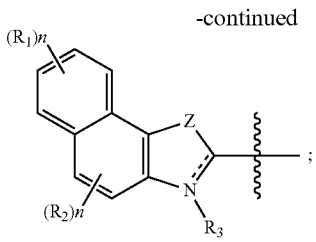

wherein:
n, as valence allows, is an integer from 0 to 4;
each occurrence of $R_1$ and $R_2$ is independently hydrogen; halogen; hydroxyl; —OR'; —SR'; —NR'R"; nitro; cyano; carbonyl; sulfonyl; or substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl; wherein each R' and R" is independently hydrogen, alkyl, cycloalkyl, heterocyclyl, aryl, or arylalkyl;
each of $R_3$ is independently hydrogen, a group having no charge, a positively charged group, or a group that can be made positively charged; and
Z is O, S, $NR_4$ or $CR_5R_6$; wherein each $R_4$, $R_5$, and $R_6$ is independently hydrogen; halogen; hydroxy, —OR'; —SR'; —NR'R"; nitro; cyano; carbonyl; sulfonyl; or substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl; wherein each R' and R" is independently hydrogen, alkyl, cycloalkyl, heterocyclyl, aryl, or arylalkyl;
wherein at least one of $R_1$, $R_2$, and W is a halogen; and
wherein the one or more cyanines are present in an effective amount to interrupt DNA replication and cause cell death in cells that express G-quadruplex DNA.

2. The pharmaceutical composition of claim 1, wherein the cyanine has the structure:

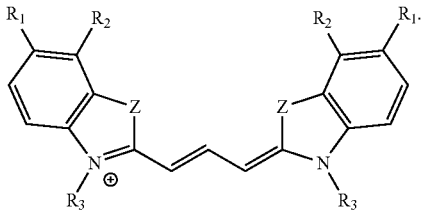

3. The pharmaceutical composition of claim 2, wherein:
(a) $R_1$=Cl, $R_2$=H, $R_3$=CH$_2$CH$_2$CH$_2$N$^+$(CH$_3$)$_3$, and Z=C(CH$_3$)$_2$;
(b) $R_1$=Br, $R_2$=H, $R_3$=CH$_2$CH$_2$CH$_2$N$^+$(CH$_3$)$_3$, and Z=C(CH$_3$)$_2$; or
(c) $R_1$=I, $R_2$=H, $R_3$=CH$_2$CH$_2$CH$_2$N$^+$(CH$_3$)$_3$, and Z=C(CH$_3$)$_2$.

4. The pharmaceutical composition of claim 1, wherein the cyanine has the structure:

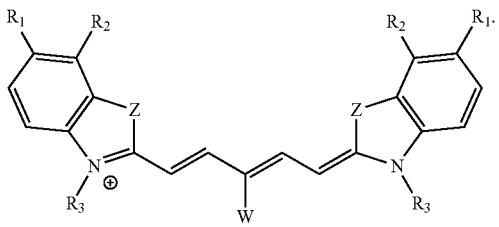

5. The pharmaceutical composition of claim 4, wherein:
(a) $R_1$=H, $R_2$=H, $R_3$=CH$_2$CH$_2$CH$_2$N$^+$(CH$_3$)$_3$, Z=C(CH$_3$)$_2$, and W=Cl;
(b) $R_1$=H, $R_2$=H, $R_3$=CH$_2$CH$_2$CH$_2$N$^+$(CH$_3$)$_3$, Z=C(CH$_3$)$_2$; and W=Br;
(c) $R_1$=Br, $R_2$=H, $R_3$=CH$_2$CH$_2$CH$_2$N$^+$(CH$_3$)$_3$, Z=C(CH$_3$)$_2$; and W=CH$_2$CH$_2$COOH;
(d) $R_1$=Cl, $R_2$=H, $R_3$=CH$_2$CH$_2$CH$_2$N$^+$(CH$_3$)$_3$, Z=C(CH$_3$)$_2$; and W=Cl;
(e) $R_1$=Cl, $R_2$=H, $R_3$=CH$_2$CH$_2$CH$_2$N$^+$(CH$_3$)$_3$, Z=C(CH$_3$)$_2$; and W=Br;
(f) $R_1$=Br, $R_2$=H, $R_3$=CH$_2$CH$_2$CH$_2$N$^+$(CH$_3$)$_3$, Z=C(CH$_3$)$_2$; and W=Cl;
(g) $R_1$=Br, $R_2$=H, $R_3$=CH$_2$CH$_2$CH$_2$N$^+$(CH$_3$)$_3$, Z=C(CH$_3$)$_2$; and W=Br;
(h) $R_1$=I, $R_2$=H, $R_3$=CH$_2$CH$_2$CH$_2$N$^+$(CH$_3$)$_3$, Z=C(CH$_3$)$_2$; and W=Cl;
(i) $R_1$=I, $R_2$=H, $R_3$=CH$_2$CH$_2$CH$_2$N$^+$(CH$_3$)$_3$, Z=C(CH$_3$)$_2$; and W=Br;
(j) $R_1$=H, $R_2$=H, $R_3$=CH$_2$CH$_2$CH$_2$N$^+$(CH$_3$)$_3$, Z=O; and W=Cl;
(k) $R_1$=H, $R_2$=H, $R_3$=CH$_2$CH$_2$CH$_2$N$^+$(CH$_3$)$_3$, Z=O; and W=Br;
(l) $R_1$=H, $R_2$=H, $R_3$=CH$_2$CH$_2$CH$_2$N$^+$(CH$_3$)$_3$, Z=S; and W=Cl;
(m) $R_1$=H, $R_2$=H, $R_3$=CH$_2$CH$_2$CH$_2$N$^+$(CH$_3$)$_3$, Z=S; and W=Br; or
(n) $R_1$=Br, $R_2$=H, $R_3$=CH$_2$CH$_2$CH$_2$N$^+$(CH$_3$)$_3$, Z=C(CH$_3$)$_2$, and W=H.

6. The pharmaceutical composition of claim 1, wherein the one or more cyanines are symmetrical cyanines, asymmetrical cyanines, or combinations thereof.

7. The pharmaceutical composition of claim 1, wherein, if present, the carbonyl is aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", or —NR'C(=O)OR");
wherein, if present, the sulfonyl is sulfate, sulfonamido, sulfamoyl or sulfonate;
wherein, if present, each R' and R" is independently hydrogen, alkyl, cycloalkyl, heterocyclyl, aryl, or arylalkyl, and r is an integer from 1 to 6;
wherein, if present, the group having no charge is a C$_{1-20}$ alkyl; and wherein, if present, the group containing one or more (a) cationic atoms or moieties or (b) atoms or moieties that are cationic under physiological conditions is a nitrogen-containing aromatic group, a cyclic amine, an amidine, a C$_{1-20}$ alkyl amino, or a C$_{1-20}$ quaternized amino.

8. The pharmaceutical composition of claim 1, wherein the cyanine has the structure

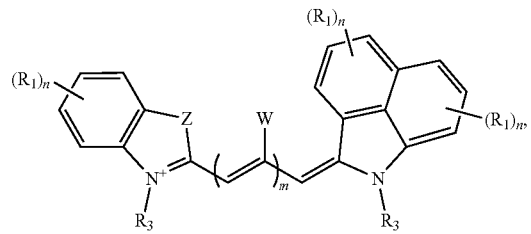

wherein one or more of $R_1$, $R_2$, and W are independently F, Cl, Br, or I;
wherein one of the $R_3$ substituents is a methyl, ethyl, propyl, or butyl; and
wherein Z is C(CH$_3$)$_2$.

9. The pharmaceutical composition of claim 1, wherein the cyanine has the structure

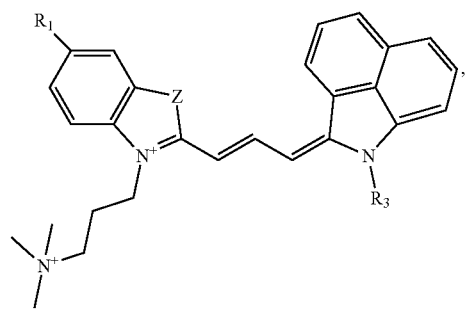

wherein $R_1$ is Br;
wherein $R_3$ is butyl; and
wherein Z is C(CH$_3$)$_2$.

10. The pharmaceutical composition of claim 1, wherein the cyanine has the structure

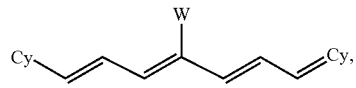

wherein each Cy is independently

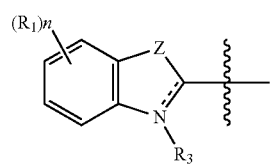

-continued

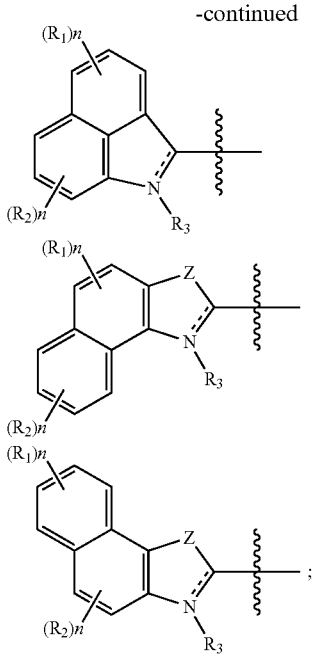

wherein:
- n, as valence allows, is an integer from 0 to 4;
- each occurrence of $R_1$ and $R_2$ is independently hydrogen; halogen; hydroxy, —OR'; —SR'; —NR'R"; nitro; cyano; carbonyl; sulfonyl; phosphoryl; and substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl, wherein each R' and R" is independently hydrogen, alkyl, cycloalkyl, heterocyclyl, aryl, or arylalkyl;
- each of $R_3$ is independently hydrogen, a group having no charge, a positively charged group, or a group that can be made positively charged; and
- Z is O, S, $NR_4$ or $CR_5R_6$; wherein each $R_4$, $R_5$, and $R_6$ is independently hydrogen; halogen; hydroxy; —OR'; —SR'; —NR'R"; nitro; cyano; carbonyl; sulfonyl; phosphoryl; or substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl; wherein each R' and R" is independently hydrogen, alkyl, cycloalkyl, heterocyclyl, aryl, or arylalkyl.

11. The pharmaceutical composition of claim 10, wherein the cyanine has the structure

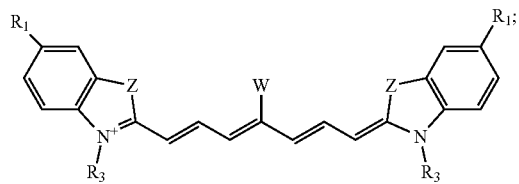

wherein W is H, Cl, or Br;
wherein each $R_1$ is independently H, F, Cl, Br, or I;
wherein each $R_3$ is independently hydrogen, a group having no charge, a positively charged group, or a group that can be made positively charged; and
wherein Z is $C(CH_3)_2$.

12. The pharmaceutical composition of claim 11, wherein the cyanine has the structure

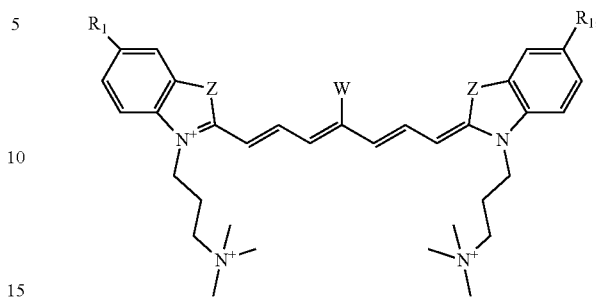

wherein $R_1$ is Br.

13. The pharmaceutical composition of claim 10, wherein, if present, the carbonyl is aldehyde, ketone, carboxylic acid, ester, amide, —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", or —NR'C(=O)OR"), wherein each R' and R" is independently hydrogen, alkyl, cycloalkyl, heterocyclyl, aryl, or arylalkyl, and r is an integer from 1 to 6;
wherein, if present, the sulfonyl is sulfate, sulfonamido, sulfamoyl, or sulfonate;
wherein, if present, the phosphoryl is phosphonate or phosphinate;
wherein, if present, the group having no charge is a $C_{1-20}$ alkyl; and
wherein, if present, the group containing one or more (a) cationic atoms or moieties or (b) atoms or moieties that are cationic under physiological conditions is a nitrogen-containing aromatic group, a cyclic amine, an amidine, a $C_{1-20}$ alkyl amino, or a $C_{1-20}$ quaternized amino.

14. The pharmaceutical composition of claim 1, wherein the cyanine has the structure

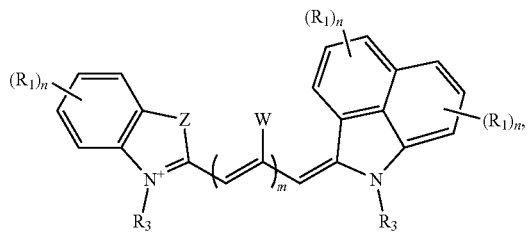

wherein one or more of $R_1$, $R_2$, and W are independently F, Cl, Br, or I;
wherein each $R_3$ group is independently $C_{1-20}$ alkyl, $C_{1-20}$ alkyl amino, or $C_{1-20}$ alkyl quaternized amino; and
wherein Z is $C(CH_3)_2$.

15. The pharmaceutical composition of claim 14, wherein each $R_3$ group is independently $C_{1-6}$ alkyl, $C_{1-6}$ alkyl amino, or $C_{1-20}$ alkyl quaternized amino.

16. The pharmaceutical composition of claim 15, wherein one of the $R_3$ groups is methyl, ethyl, propyl, or butyl.

17. The pharmaceutical composition of claim 1, wherein at least one $R_1$ or $R_2$ is halogen.

18. The pharmaceutical composition of claim 1, wherein at least one $R_1$ or $R_2$ is aryl substituted with halogen.

19. The pharmaceutical composition of claim 1, wherein m is 0, 1, or 2; wherein at least one $R_3$ is a nitrogen-containing aromatic group, a cyclic amine, an amidine, a $C_{1-20}$ alkyl amino, or a $C_{1-20}$ alkyl quaternized amino; wherein Z is $CR_5R_6$, and each $R_5$ and $R_6$ is independently a substituted or unsubstituted alkyl group or a substituted or unsubstituted aryl group; and wherein the total charge of the cyanine is not negative and not less than +3.

20. The pharmaceutical composition of claim 1, wherein m is 1 or 2;
wherein at least one $R_3$ is a $C_{1-20}$ alkyl quaternized amino; wherein Z is $CR_5R_6$, and $R_5$ and $R_6$ are methyl groups; wherein at least one $R_1$ or $R_2$ is a halogen; and wherein the total charge of the cyanine is not negative and not less than +3.

21. A method for selectively binding G-quadruplex DNA comprising contacting the DNA with an effective amount of one or more pharmaceutical composition of claim 1 that are selective for G-quadruplex DNA.

22. The method of claim 21, wherein the one or more cyanines are symmetrical cyanines, asymmetrical cyanines, or combinations thereof.

23. A method for treating a disease or disorder characterized by expression of G-quadruplex DNA, the method comprising administering to a patient in need thereof the pharmaceutical composition of claim 7.

24. The method of claim 23, wherein the composition is administered enterally.

25. The method of claim 23, wherein the composition is administered parenterally.

26. The method of claim 23, wherein the disease or disorder is cancer.

27. A cyanine having the formula:

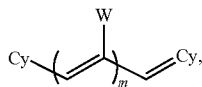

wherein:
m=1 or 2;
each Cy is independently a substituted or unsubstituted heteroaromatic moiety, wherein at least one of the heteroatoms in at least one Cy is nitrogen substituted with a group containing one or more cationic moieties, and wherein each Cy is the same or different;
each occurrence of W is independently hydrogen; halogen; cyano; trifluoromethyl; benzoic acid; substituted or unsubstituted alkyl, alkenyl, alkynyl, cycloalkyl, or cycloalkenyl; or a group containing one or more (a) cationic atoms or moieties or (b) atoms or moieties that are cationic under physiological conditions;
and
wherein each Cy is independently:

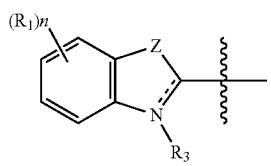

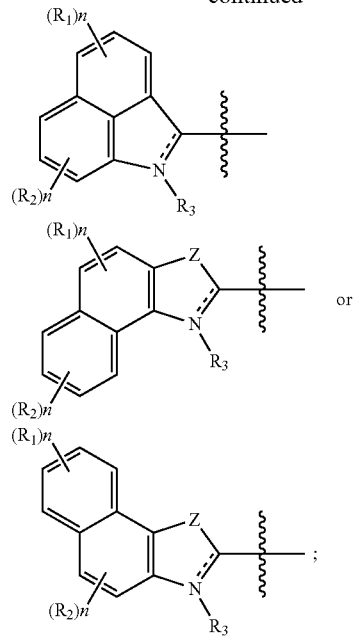

wherein:
n, as valence allows, is an integer from 0 to 4;
each occurrence of $R_1$ and $R_2$ is independently hydrogen; halogen; hydroxyl; —OR'; —SR'; —NR'R"; nitro; cyano; carbonyl; sulfonyl; or substituted or unsubstituted alkyl, alkenyl, alkynyl, cycloalkyl, heterocycloalkyl, cycloalkenyl, heterocycloalkenyl, aryl, heteroaryl, alkylaryl, or arylalkyl; wherein each R' and R" is independently hydrogen, alkyl, cycloalkyl, heterocyclyl, aryl, or arylalkyl;
each $R_3$ is independently $C_1$-$C_{20}$ alkyl amino or $C_1$-$C_{20}$ quaternized amino;
Z is $CR_5R_6$; wherein each $R_5$ and $R_6$ is independently hydrogen; or unsubstituted alkyl or aryl; wherein at least one of $R_5$ and R6 is not hydrogen;
wherein at least one of $R_1$, $R_2$, and W is a halogen; and wherein the total charge of the cyanine is not negative and not less than +3,
with the proviso that:
(a) one or more substituent(s), when present, on the amino group of the alkyl amino or quaternized amino are straight chain alkyl or branched chain alkyl;
(b) when both Cy are

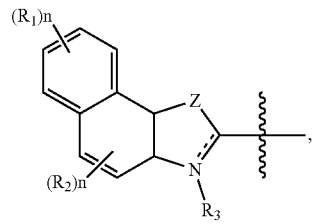

m is 2, one W is Cl or Br, both Z are $CR_5R_6$ and $R_5$ and $R_6$ are methyl, each occurrence of $R_1$ and $R_2$ is H, then one $R_3$ is not —$(CH_2)_3$—$N^+Me_3$.

28. The cyanine of claim 27, wherein at least one $R_3$ is a $C_{1-20}$ alkyl quaternized amino; and wherein Z is $CR_5R_6$, and each $R_5$ and $R_6$ is independently an unsubstituted alkyl group.

29. The cyanine of claim 27, wherein at least one $R_3$ is a $C_{1-10}$ alkyl quaternized amino; wherein Z is $CR_5R_6$, and $R_5$ and $R_6$ are methyl groups; wherein at least one $R_1$ or $R_2$ is a halogen.

30. A pharmaceutical composition comprising (i) one or more cyanines of claim 27, wherein the one or more cyanines are selective for G-quadruplex DNA over duplex DNA and (ii) one or more pharmaceutical acceptable excipients, wherein the one or more cyanines are present in an effective amount to interrupt DNA replication in cells that express G-quadruplex DNA.

31. The pharmaceutical composition of claim 30, wherein the one or more cyanines are present in an amount effective to cause cell death.

32. The pharmaceutical composition of claim 30, wherein the one or more cyanines are symmetrical cyanines, asymmetrical cyanines, or combinations thereof.

* * * * *